(12) United States Patent
Virgos et al.

(10) Patent No.: US 7,312,034 B2
(45) Date of Patent: Dec. 25, 2007

(54) UNIVERSAL E-TAG PRIMER AND PROBE COMPOSITIONS AND METHODS

(75) Inventors: Carmen Virgos, San Jose, CA (US); Maureen Cronin, Los Altos, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 330 days.

(21) Appl. No.: 10/811,248

(22) Filed: Mar. 26, 2004

(65) Prior Publication Data

US 2004/0191823 A1 Sep. 30, 2004

Related U.S. Application Data

(63) Continuation of application No. PCT/US02/32867, filed on Oct. 16, 2002.

(60) Provisional application No. 60/330,021, filed on Oct. 16, 2001.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search .................. 435/6; 536/23.1, 24.3
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,210,015 A | 5/1993 | Gelfand |
| 5,703,222 A | 12/1997 | Grossman et al. |
| 5,876,924 A | 3/1999 | Zhang et al. |
| 5,882,856 A | 3/1999 | Shuber |
| 6,150,516 A | 11/2000 | Brenner et al. |
| 6,287,778 B1 | 9/2001 | Huang et al. |
| 6,322,980 B1 * | 11/2001 | Singh ........................ 435/6 |

FOREIGN PATENT DOCUMENTS

| | | |
|---|---|---|
| EP | 0731 177 A2 | 9/1996 |
| WO | WO 99/05319 | 2/1999 |
| WO | WO 00/66607 A1 | 11/2000 |

OTHER PUBLICATIONS

Virgos et al., Multiplex SNP scoring of cardiovascular candidate genes by a novel labeling strategy and microcapillary electrophoresis. European Journal of Human Genetics (2001) vol. 9, No. Supplement 1, pp. P1146. Meeting Info.: 10th International Congress of Human Genetics. Vienna, Austria. May 15-19, 2001. Abstract Only.*
Grothues et al, "PCR Amplification of Megabase DNA with Tagged Random Primers (T-PCR)"Nucleic Acids Research, 1993, vol. 21, No. 5, pp. 1321-1322.
Chee, "Enzymatic Multiplex DNA Sequencing", Nucleic Acids Research, 1991, vol. 19, No. 12, pp. 3301-3302.
Giese, "Electrophoric Release Tags: Ultrasensitive Molecular Labels Providing Multiplicity" Trends in Analytical Chemistry, vol. 2, No. 7, 1983.

* cited by examiner

*Primary Examiner*—Ethan Whisenant
(74) *Attorney, Agent, or Firm*—Fenwick & West LLP

(57) ABSTRACT

The invention provides universal e-tag primers and methods for their use in the sequence specific detection and multiplexed analysis of known, selected target nucleic acid sequences. The universal e-tag primers have sequence specific and universal components for use in e-tag probe-mediated analysis of target nucleic acids.

21 Claims, 24 Drawing Sheets

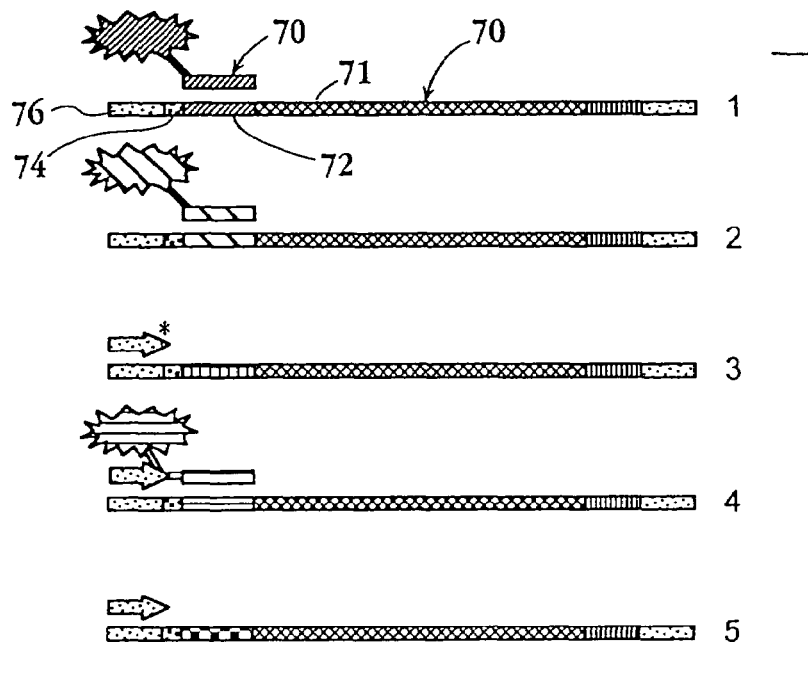
Fig. 2A
Endomeliase treatment
Tag Separation ad detection
Fig. 2B
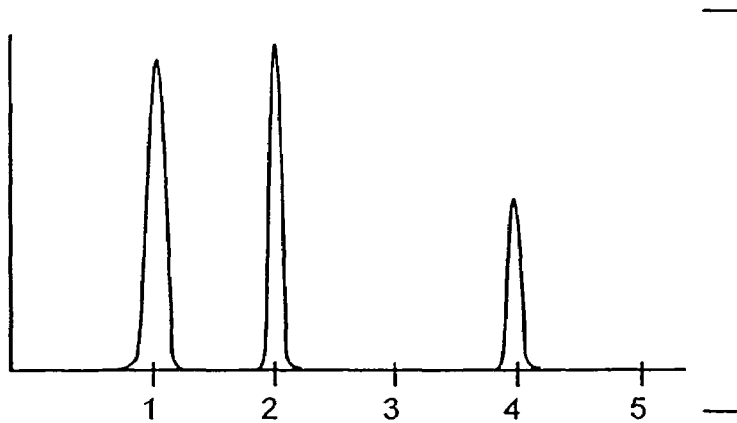
Fig. 2C

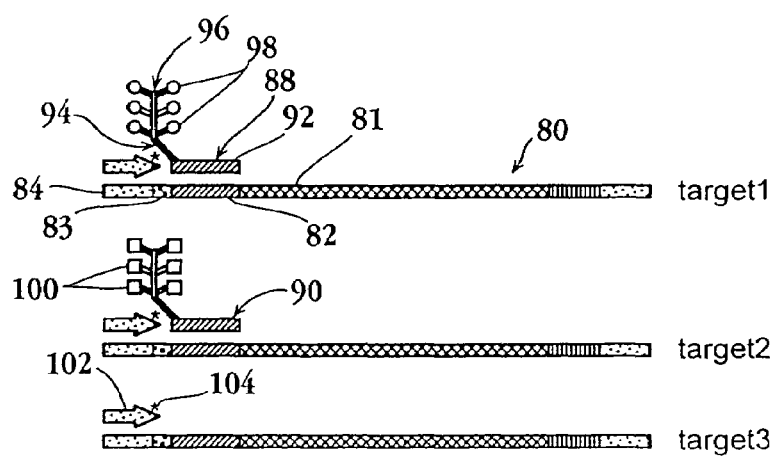
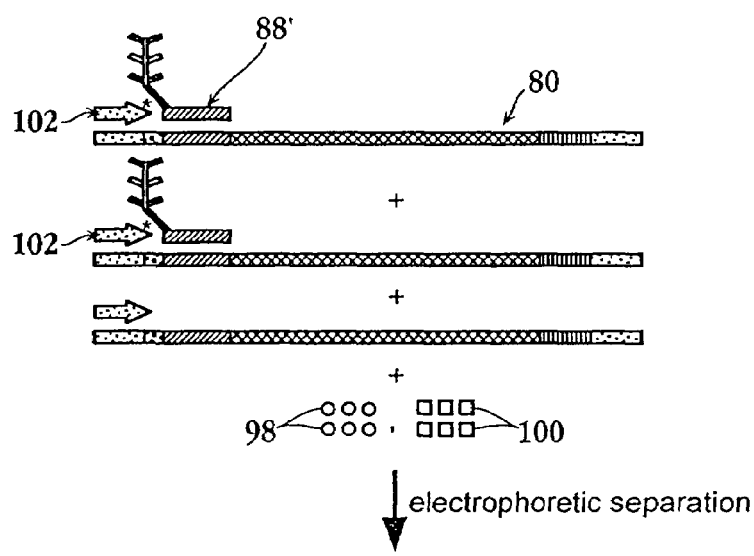

↓ catalytic reaction detection

ACLA037
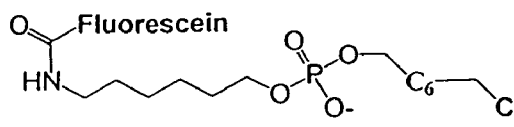
ACLA038
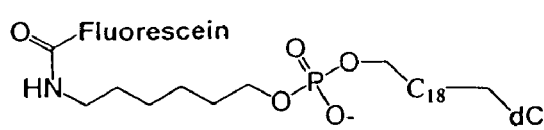
ACLA039
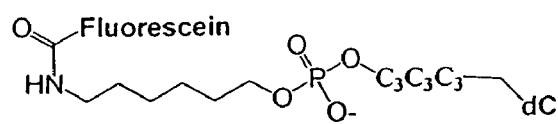
ACLA040
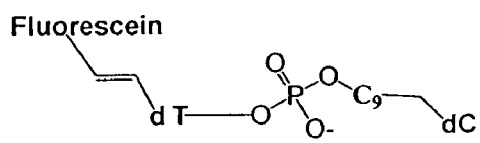
ACLA041
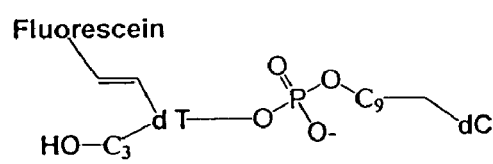
ACLA042
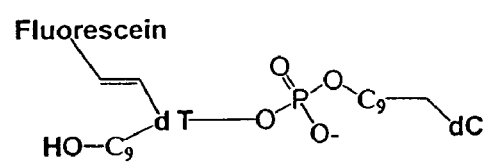
ACLA043
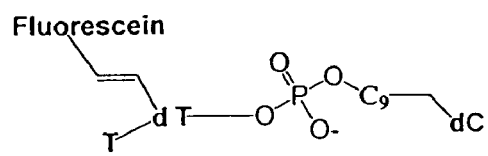
ACLA044
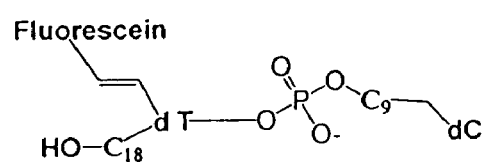
ACLA045
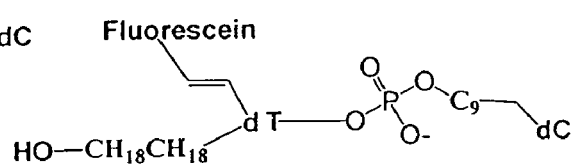
ACLA046
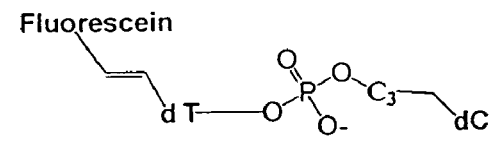
ACLA047
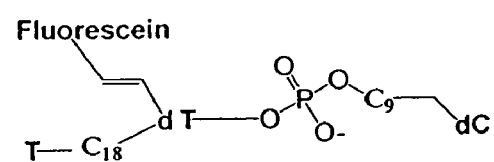
Fig. 9D

| e-tag Reporter | Charge | Elution Time, min |
|---|---|---|
| Fluorescein-HN-(CH₂)₅-O-P(O)(O⁻)-C₃C₃C₃C₃C₃-dC | -8 | 12.1* |
| Fluorescein-HN-(CH₂)₅-O-P(O)(O⁻)-O-C₆C₆C₆C₆C₆C₆-dC | -9 | 12.7 |
| Fluorescein-HN-(CH₂)₅-O-P(O)(O⁻)-O-C₆C₆C₆C₆C₆-dC | -8 | 12.8 |
| Fluorescein-HN-(CH₂)₅-O-P(O)(O⁻)-O-C₆C₆C₆C₆-dC | -7 | 13.1 |
| Fluorescein-HN-(CH₂)₅-O-P(O)(O⁻)-O-C₃C₃C₉-dC | -6 | 13.0 |
| Fluorescein-HN-(CH₂)₅-O-P(O)(O⁻)-O-C₆C₆C₆-dC | -6 | 13.4 |
| Fluorescein-HN-(CH₂)₅-O-P(O)(O⁻)-O-C₃C₃-dC | -5 | 12.8* |
| Fluorescein-HN-(CH₂)₅-O-P(O)(O⁻)-O-C₃C₉-dC | -5 | 13.2* |
| Fluorescein-HN-(CH₂)₅-O-P(O)(O⁻)-O-C₉C₉-dC | -5 | 14.8 |
| Fluorescein-HN-(CH₂)₅-O-P(O)(O⁻)-O-TTTdC | -6 | 17.3 |
| Fluorescein-HN-(CH₂)₅-O-P(O)(O⁻)-O-TTdC | -5 | 17.0 |
| Fluorescein-HN-(CH₂)₅-O-P(O)(O⁻)-O-C₉-dT | -4 | 15.2* |
| Fluorescein-HN-(CH₂)₅-O-P(O)(O⁻)-O-TdC | -4 | 16.5 |

Fig. 10

UNIVERSAL E-TAG PRIMER AND PROBE COMPOSITIONS AND METHODS

CROSS-REFERENCE TO RELATED APPLICATIONS AND PATENTS

This application is a continuation of and claims priority of International application PCT/US02/32867 filed 16 Oct. 2002, which claims priority to U.S. Provisional Application Ser. No. 60/330,021 filed 16 Oct. 2001, which applications are each incorporated herein by reference in their entirety.

FIELD OF THE INVENTION

The present invention relates to primers and probes having sequence-specific and universal components, compositions, methods, and kits for use in e-tag probe-mediated multiplexed assay detection of known, selected target nucleotide sequences.

BACKGROUND OF THE INVENTION

The need to determine multiple nucleic acid sequences in biological samples at the same time in an efficient, reliable and reproducible manner has become increasingly important to numerous disciplines. Most multi-target analyses, such as assays that detect multiple nucleic acid sequences, involve several steps and/or require multiple reactions, have poor sensitivity, a limited dynamic range (typically on the order of 2 to 100-fold differences) and some require sophisticated instrumentation.

At present, there are a large number of application for assays useful to determine the presence of specific sequences, distinguishing between alleles in homozygotes and heterozygotes, determining the presence of mutations, evaluating cellular expressions patterns, etc. In many of these cases one will wish to determine in a single reaction, a number of different characteristics of the same sample. In many assays, there will be an interest in determining the presence of specific sequences, whether genomic, synthetic, or cDNA. Any method should be accurate, have reasonable associated costs and provide for a multiplexed assay, which allows for differentiation and quantitation of multiple genes, and/or SNP determination, and/or gene expression.

At present, when analyzing large and/or undefined genes, multiple individual PCR reactions are often required to identify critical base changes or deletions. The results obtained with multiplex PCR are frequently complicated by artifacts of the amplification procedure including both "false-negatives" and "false-positives". The use of the Amplification Refractory Mutation system (ARMS), also known as Allele Specific PCR (ASPCR) and PCR Amplification of Specific Alleles (PASA) has been described for detection of known single-base substitutions or mocrodeletions/insertions. See, e.g., Sommer et al. Mayo Clinic Proc 64, 1361, 1989 ( PASA); Netwon et al. Nucl Acids Res 17, 2503, 1989 (ARMS); and Wu et al. PNSA 86, 2757, 1989 (ASPCR). The assay typically requires two separate reactions to determine both alleles for a given gene locus.

Thus an assay that can be used to differentiate and quantiate multiple genes, and/or be used to analyze gene expression at the RNA level is desirable. Preferably such an assay has most or all of the following characteristics: (1) a simple format, such as a single assay mixture where most or all of the reagents are added at the same time; (2) high sensitivity; (3) a large dynamic range ($10^3$ to $10^4$-fold differences in target levels); (4) multiplexing capability; (5) reproducibility/reliability; and (6) a reasonable cost per analysis.

BRIEF DESCRIPTION OF THE RELATED ART

Holland (Proc. Natl. Acad. Sci. USA (1991) 88:7276) discloses that the exonuclease activity of the thermostable enzyme *Thermus aquaticus* DNA polymerase in PCR amplification to generate specific detectable signal concomitantly with amplification.

The TaqMan® assay is discussed by Lee in *Nucleic Acid Research* (1993) 21:16 3761)

White (Trends Biotechnology (1996) 14(12): 478-483) discusses the problems of multiplexing in the TaqMan assay.

Marino, *Electrophoresis* (1996) 17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

U.S. Pat. No. 5,807,682 describes probe compositions and methods for their use in detecting a plurality of nucleic acid targets. A plurality of sequence-specific probes having a specific sequence component for binding to one of the target sequences, and a polymer chain having a different ratio of charge/translational frictional drag from that of the sequence-specific probe are described. In carrying out the method, the probes which are bound to the target form modified, labeled probes which are fractionated by electrophoresis in a non-sieving matrix, then detected.

Whitcombe, D et al., *Clinical Chemistry* 44(5): 918-923, 1998, is directed to a homogeneous fluorescence assay for PCR amplicons where a 5'-exonuclease assay of amplicon annealed fluorganic TaqMan® probes is carried out in conjunction with the Amplification Refractory Mutation System (ARMS). The assay is used for the single-tube genotype analysis of human DNA polymorphisms and mutations.

U.S. Pat. No. 5,595,890 and European Patent No. EP 0 332 435 describe the Amplification Refractory Mutation System (ARMS) which employs a primer extension method to detect the presence or absence of suspected variant nucleotides.

U.S. Pat. No. 5,882,856 and WO 96/41012 describe universal primer sequences for multiplex DNA amplification where the 3' sequence of one primer of each pair comprises a target DNA sequence or its complement.

U.S. Pat. No. 5,210,015 (Gelfand) describes a homogeneous assay system using a 5'-exonulcease assay.

U.S. Pat. No. 5,487,972 (Gelfand) describes nucleic acid detection by the 5'-3-exonuclease activity of polymerases acting on adjacently hybridized oligonucleotides.

PCT publication WO 97/42345 describes a method for detecting a SNP at 3' end of primer with universal primer tailing and a TaqMan assay.

European Patent Application No. 0731177 describes primer tailing using primers which selectively prime specific type(s) of internal repeats in a tandemly repeated sequence.

SUMMARY OF THE INVENTION

In one aspect, the invention includes a method of detecting each or any of a plurality of known, selected nucleotide target sequences in a sample. In practicing the method, the target sequences are mixed with (i) a set of forward universal e-tag primers, each containing (ia) a target sequence that is complementary to one of the known selected target sequences, and (ib) an extension sequence which is unique to the target sequence of that member, (ii) one or more reverse universal e-tag primers that are complementary to said target sequences, and (iii) enzyme and nucleotide components of a primer extension reaction, to form a target-sequence reaction mixture.

The mixture is first reacted under primer extension reaction conditions, to form extended, preferably amplified target sequences. The extended target sequences are then reacted under hybridization conditions with a set of electrophoretic tag (e-tag) probes, each having (i) an oligonucleotide target-binding portion or moiety that is complementary to one of the extension sequences, (ii) an electrophoretic probe having separation characteristics, e.g., electrophoretic mobility, that is unique to a given extension sequence, and (iii) a linker joining the oligonucleotide portion and the electrophoretic probe, where the linker is cleavable under selected conditions when the oligonucleotide portion of the probe is bound to a complementary target extension sequence.

The target sequences with bound probes are treated under the selected conditions, to release an e-tag reporter from each e-tag probe bound to a target sequence, the released reporters are separated, e.g., electrophoretically, and the separated reporters are detected, to identify target sequences that hybridized to the probes.

In one embodiment, the cleaving agent is a DNA polymerase having 5'-exonuclease activity, and the linker is a nucleotide linked to the 5' end of the oligonucleotide portion through a nuclease cleavable bond. In another embodiment, the cleaving agent is a restriction enzyme, and the linker includes the specific sequence cleaved by the restriction enzyme. In a third embodiment, the cleaving agent is a sensitizer capable of generating activated oxygen under conditions of light illumination.

In one general embodiment, the tag probes have the form $(D, M_j)$-N-$T_j$, which are cleaved to an electrophoretic tag reporter of the form $(D, M_j)$-N', where (i) D is a detection group comprising a detectable label or a catalytic group capable of catalyzing a detectable reaction;

(ii) $T_j$ is an oligonucleotide target-binding moiety for binding an e-tag probe recognition sequence;

(iii) N is linker joined to the 5'-end nucleotide in $T_j$ through a cleavable bond;

(iv) N' is the residue of N remaining after cleavage;

(v) $M_j$ is a mobility having a charge/mass ratio that imparts to the corresponding electrophoretic tag, an electrophoretic mobility that is unique to a given extension sequence; and (vi) $(D, M_j)$-includes both $D-M_j$- and $M_j$-D-.

In one specific embodiment, N is a nucleotide, and each e-tag probe target binding moiety contains at least one modification which is a nuclease-resistant bond joining at least the two 5'-end nucleotides of the target binding moiety, or a capture ligand, such as biotin, contained on the '5-end nucleotide of the target binding moiety and capable of binding specifically to a capture agent, such as streptavidin. In another embodiment, N is a sequence that contains the recognition sequence for a selected restriction endonculease. In a third site for a linkage cleavable by singlet oxygen.

In another general embodiment, the e-tag probes are multi-tag probes having one of two general forms. In one, the probes have the general form $(D, M_j$-$L)_j$-$B$-$T_j$, cleaved to the form $(D_j Mj)$-$L'_j$ where (i) D is a detection group comprising a detectable label or a catalytic group capable of catalyzing a detectable reaction;

(ii) $T_j$ is an oligonucleotide target-binding moiety for binding an e-tag probe recognition sequence;

(iii) B is a branched polymer or other multisite structure having multiple electrophoretic tags probes attached thereto, each through a linkage L that is cleavage under target-dependent conditions;

(iv) L' is the residue of L remaining after cleavage of the electrophoretic probes from the branched structure;

(v) $M_j$ is a mobility modifier having a charge/mass ratio that imparts to the corresponding electrophoretic tag, an electrophoretic mobility that is unique to a given extension sequence; and (vi) $(D, M_j)$-includes both $D-M_j$- and $M_j$-D-.

In another multi-tag probe embodiment, the probes in the set have the general form $(D, M_j)_n$-$B$-$N$-$T_j$, which are cleaved in the method under the selected cleavage conditions to a branched structure $(D, M_j)_n$-$B$-$N'$, and are further cleaved to a plurality of electrophoretic tags of the form $(D, M_j)$-$B'$, where (i) D is a detection group comprising a detectable label or a catalytic group capable of catalyzing a detectable reaction;

(ii) $T_j$ is an oligonucleotide target-binding moiety for binding an e-tag probe recognition sequence;

(iii) B is a branched polymer having n electrophoretic tags probes attached thereto, each through a linkage that is cleavage under cleavage conditions different from said selected conditions employed in releasing the branched structure from the probe;

(iv) B' is the residue of B remaining after cleavage of the electrophoretic probes from the branched structure;

(v) N' is the residue of N remaining after cleavage of the branched structure from said probe;

(vi) $M_j$ is a mobility modifier having a charge/mass ratio that imparts to the corresponding electrophoretic tag, an electrophoretic mobility that is unique to a given extension sequence; and (vii) $(D, M_j)$-includes both $D-M_j$- and $M_j$-D-. In using these probes in the method of the invention, the probe are treated under selected conditions to release branched structures in probes hybridized with target sequences, and the released branchede structures are further treated, under said different cleavage conditions, to release electrophoretic probes from the branched structures.

In another aspect, the invention includes a kit for detecting each or any of a plurality of known, selected nucleotide target sequences. The kit includes (a) a set of forward oligonucleotide primers, each containing (ia) a target-sequence that is complementary to one of the known selected target sequences, and (ib) an extension sequence which is unique to the target sequence of that member, and (b) one or more reverse universal e-tag primers that are complementary to the target sequences, where the forward and reverse primers are effective, in the presence enzyme and nucleotide components of a primer extension reaction, to form amplified, extended target sequences. Also included is a set of electrophoretic tag (e-tag) probes of the type described above. The kit may further enzymes and nucleotide components of a PCR reaction.

The extension sequence may include, in a 5'-to-3' direction, a universal primer extension sequence and an e-tag-probe extension sequence, where said kit further includes one or more upstream primers capable of hybridizing to the universal primer extension sequence. This kit can be used, for example, with a DNA polymerase having 5'-exonuclease activity to cleave the probe, where the probe linker is a nucleotide linked to the 5' end of the oligonucleotide portion through a nuclease cleavable bond. Alternatively, for use with a linker that is cleaved by singlet oxygen, the one or more upstream primers include a moiety capable of generating singlet oxygen in the presence of light.

Where the probe linker includes or is the specific sequence cleaved by a selected restriction enzyme, the kit further includes the selected restriction enzyme.

These and other objects and features of the invention will become more fully apparent when the following detailed description of the invention is read in conjunction with the accompanying drawings.

BRIEF DESCRIPTION OF THE DRAWINGS

FIGS. 2A-2C illustrate steps in practicing the method of the invention, in another general embodiment of the invention.

FIGS. 3A-3D illustrate steps in practicing the method of the invention, in still another general embodiment of the invention.

FIGS. 9A-9J show the structures of numerous exemplary e-tag reporters;

FIG. 10 provides predicted or experimental (*) elution times of e-tag reporters separated by capillary electrophoresis. $C_3$, $C_6$, $C_9$, and $C_{18}$ are commercially available phosphoramidite spacers.

FIG. 2A); NA17002 DNA which is homozygous for the MTHFR C677T mutant allele (wild type/wild type; FIG. 2B); NA17003 DNA, which is heterozygous for the MTHFR C677T mutant allele (wild type/mutant; FIG. 2C); NA17005 DNA which is homozygous for the MTHFR C677T wild type allele (wild type/wild type; FIG. 2D); NA17008 DNA which is heterozygous for the MTHFR C677T mutant allele (wild type/ mutant; FIG. 2E); NA17010 DNA, which is homozygous for the MTHFR C677T mutant allele (mutant/mutant; FIG. 2F) and a water control (FIG. 2G).

FIGS. 3A-C illustrate the results obtained using a universal e-tag primer and e-tag probe specific for the wild type MTHFR C677T target and FIGS. 3D-F illustrate the results obtained using a universal e-tag primer and e-tag probe specific for the mutant MTHFR C677T target in separate reactions, where the template DNA previously characterized for the MTHFR C677 SNP as mutant/mutant (NA17001 DNA; FIGS. 3B, 3E); wild type/ wild type (NA17002 DNA; FIGS. 3A, 3D); using water as a negative control (FIGS. 3C, 3F).

DETAILED DESCRIPTION OF THE INVENTION

I. Definitions

Figure 1A:
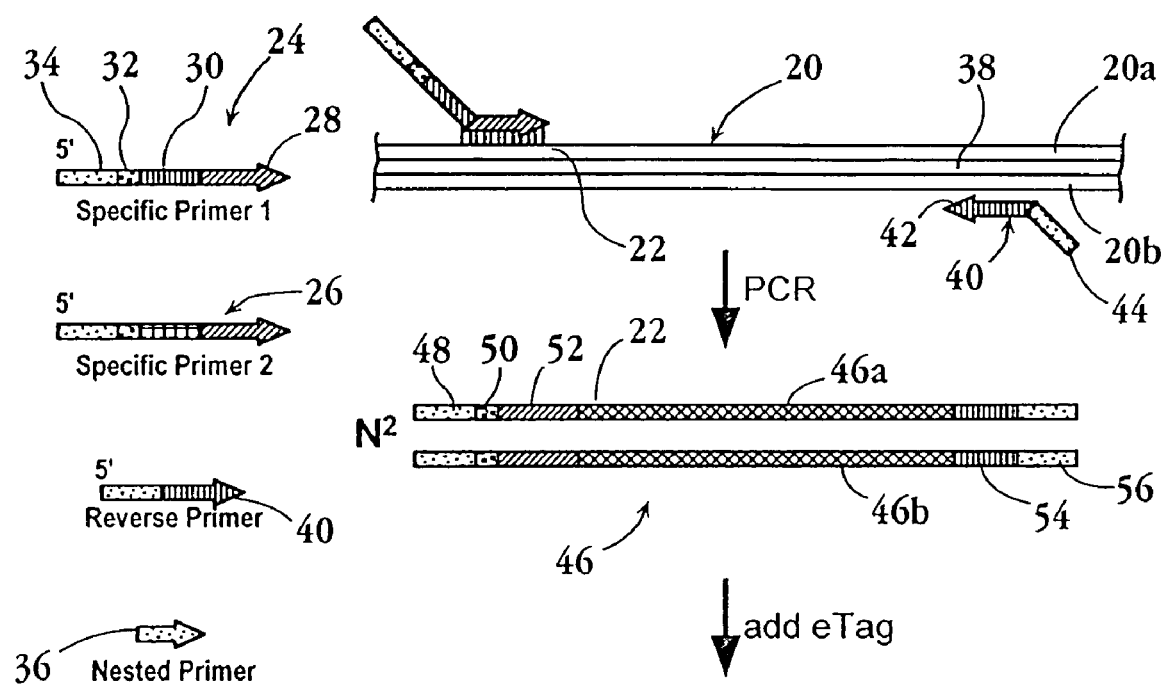
FIGS. 1A-1C illustrate steps in practicing the method of the invention, in one general embodiment.

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

As user herein, the terms "complementary" or "complementarity" refer to an oligonucleotide which, may be aligned with another nucleic acid sequence such that the 5' end of one sequence is paired with the 3' end of the other in an antiparallel orientation. Complementarity need not be perfect and stable duplexes may be obtained using sequences that contain mismatches.

A nucleic acid sequence is considered to "selectively hybridize" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while high stringency conditions are used to identify sequences having about 80% or more sequence identity with the probe.

As used herein the temrs "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences.

Moderate and high stringency hybridization conditions are well known in the art (see, for example, Sambrook, et al, 1989, Chapters 9 and 11, and in Ausubel. F. M., et al., 1993, expressly incorporated by reference herein). An example of high stringency conditions includes hybridization at about 42° C. in 50% formamide, 5X SSC, 5X Denhardt's solution, 0.5% SDS and 100 µg/ml denatured carrier DNA followed by washing two times in 2X SSC and 0.5% SDS at room temperature and two additional times in 0.1X SSC and 0.5% SDS at 42° C.

As used herein, the term "oligonucleotide" refers to a molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

As used herein, the term "sequence identity" means nucleic acid or amino acid sequence identity in two or more aligned sequences, aligned using a sequence alignment program.

As used herein, the term "gene" means the segment of DNA involved in producing a polypeptide, which may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "universal electrophoretic tag primer set" or "universal e-tag primer set" refers to a set of primers for use in detecting each or any of a plurality of known, selected target nucleotide sequences and which includes a set of forward universal e-tag primers and reverse universal e-tag primers, wherein the target specificity is dictated by the forward universal e-tag primer of the set. A set of e-tag primers typically has k members where each member is capable of specific detection of a selected target nucleotide sequence.

As used herein, the term "electrophoretic tag probe set" or "e-tag probe set" refers to a set of probes for use in binding to the e-tag probe recognition site generated by amplification following the specific binding of a universal e-tag primer to a target nucleic acid sequence. A set of e-tag probers typically has j members where each member is capable of specific binding to a particular e-tag probe recognition site.

The term "set" or "group" as used herein relative to universal electrophoretic tag (e-tag) primers or e-tag probes refers to a plurality of e-tag primers or probes, respectively, having typically at least four, and typically 10-100 or more primers and/or probes with different unique target-specific components and detection moieties.

In one application of this embodiment, the e-tag probe is referred to as a SNP detection sequence, a fluorescence SNP detection sequence or an oligonucleotide detection sequence.

As used herein, the term "binding event" generally refers to the binding of the target-binding moiety of an e-tag probe to its target. By way of example, such binding may invovle the interaction between complementary nucleotide sequences.

As used herein, the term "capture ligand", refers to a group that is typically included within the target binding moiety or portion of an e-tag probe and is capable of binding specifically to a "capture agent" or receptor. The interaction between such a capture ligand and the corresponding capture agent may be used to separate uncleaved e-tag probes from released e-tag reporters.

As used herein, the term "cleaving agent" may be used interchangeably with the terms "cleavage moiety" and "cleavage means" all of which refer to an agent capable of cleaving an e-tag probe to release the corresponding e-tag reporter.

As used herein, the term "cleavage products" refers to producs generated by the action of a cleaving agent (i.e., the treatment of a target bound e-tag probe with a cleaving agent).

As used herein, the ther "wild-type", "native" and "normal" when used in reference to a gene or gene product means the gene or gene product has the same characteristics as the same gene or gene product which has is found in a native or naturally occurring source.

As used herein, the term "modified" or "mutant" with reference to a gene or gene product refers to a sequence that differs from the corresponding wild type gene or gene product in terms of sequence and/or functional properties relative to the wild-type gene or gene product.

The term "universal e-tag primer", as used herein refers to a primer used for the which has the form $U_p$-S-$T_p$-$P_k$. The universal e-tag primers of the invention are typically employed in a multiplexed assay format for the detection of each or any of a number of known, selected target nucleotide sequences.

The "$U_p$" sequence of a universal e-tag primer is an oligonucleotide sequence that is common to a given set of universal e-tag primers.

The term "nucleotide spacer squence" or "S" of a universal e-tag primer is a nucleotide sequence that serves to link the universal sequence component of a universal e-tag primer to primer component for generation the e-tag recognition site. "S" is at least 2 nucleotides in length, generally 2-7 nucleotides in length, and typically 4-6 nucleotides in length.

The "e-tag extension sequence" or "primer component for generation of the e-tag recognition site" or "$T_p$", as used herein refers to the sequence component of a universal e-tag primer that is designed to generate the target which will hybridize specifically with the target binding moiety of an e-tag probe.

Accordingly, the "e-tag recognition site" is the sequence generated following specific binding of a universal e-tag primer to a target nucleic acid and amplification, e.g. by PCR. The particular conditions for such amplification are further described below. The "e-tag recognition site" is also referred to herein as an "e-tag recognition sequence", an "e-tag target" site or sequence and an "e-tag probe binding" site or sequence.

II. Method of the Invention

Methods for conducting multiplexed assays to detect each or any of a plurality of known, selected nucleotide target sequences in a sample, using sequence-specific electrophoretic probes to bind to complementary target sequences in the sample, and hybrid-specific cleavage of electrophoretic tags to identify target sequences having bound probe, have been described. See, for example, co-owned U.S. patent application for Sets of Oligonucleotide Binding E-tag Probes, Ser. No. 09/825,246, filed Apr. 2, 2001; "Methods Employing Oligonucleotide Binging E-tag Probes," Ser. No. 09/825,247 filed Apr. 2, 2001; "Kits Employing Okligonucleotide Binding E-tag Probes," Ser. No. 09/824,905, filed Apr. 2, 2001; "Oligonucleotide Binding E-tag Probe Composition," Ser. No. 09/825,245, filed Apr. 2, 2001; "Sets of Generalized Target-Binding E-tag Probes," Ser. No. 09/825,244, filed Apr. 2, 2001; "Methods Employing Generalized Target-Binding E-tag Probes," Ser. No. 09/824,984, filed Apr. 2, 2001; "Kits E,ploying Generalized Target-Binding E-tag Probes, Ser. No. 09/824,851, Apr. 2, 2001; "Generalized Target-Binding E-tag Probe Compositions," Ser. No. 09/824,861, filed Apr. 2, 2001 (attched herto); "Single Nucleotide Detection Using Degradation of a Fluorescent Sequence," Ser. No. 09/303,029, filed Apr. 30, 1999; "Detection Using Degradation of a Tagged Sequence," Ser. No. 09/561,579, filed Apr. 28, 2000; "Electrophoretic Tag Libraries," Ser. No. 09/602,586, filed Jun. 21, 2000; "Tag Library Compounds, Compositions, Kits, and Methods of Use," Ser. No. 09/684,386, filed Oct. 4, 2000; "Tag Library Compounds, Compositions, Kits, and Methods of Use," Ser. No. 698,846, filed Oct. 27, 2000; PCT application for Single Nucletodie Detection Using Degradation of a Fluorescent Sequence," WO00/10501, filed Apr. 19, 2000; PCT application for "Detection Using Degradation of a Tagged Sequence, WO00/11396, filed Apr. 28, 2000; and PCT application for "Tag Library Compounds, Compositions, Kits and Methods of Use," WO00/29724, filed Oct. 27, 2000. all incorporated by reference and referred to collectively herein as "E-tag Patents."

Briefly, the method described in the E-tag Patents employs a set of probes, each having an oligonucleotide moiety designed for base-specific binding one of a plurality of different target sequences, a releasable electrophoretic tag, or e-tag, and a cleavable linker joining the e-tag to the oligonucleotide moiety. The e-tag, in turn, is composed of a detecting moiety by which the tag can be detected, and a mobility modifier which imparts to the tag, a unique separation characteristic, e.g., electrophoretic mobility, by which each different e-tag in the set can be separated and identified with the associated oligonucleotide binding sequence. The cleavage linker is a covalent chemical bond or group of atoms containing a covalent bond which is cleavable by a selected cleaving agent only when the probe is bound to associated target sequence.

In practice, the set of e-tag probes described in the E-tag Patents are mixed with a sample containing one or more target oligonucleotide sequences to be assayed, under conditions allowing probe hybridization to the complementary target sequences. The probe-target hybrids are then treated with the selected cleaving agent, and the released e-tags are combined and separated, e.g., electrophoretically. From the separation results, e.g., electropherogram, the particular e-tags released can be identified, and from this, the associated target sequences in the sample can be identified.

The present invention extends this method to universal format, allowing a single set of e-tag probes to be employed in identifying samples containing any group of different target sequences. The method involves first amplifying the target nucleic acids, e.g., double-stranded DNA fragments, with PCR primers that including (i) a set of forward universal e-tag primers, each containing (ia) a target sequence that is complementary to one of the known selected target sequences, and (ib) an extension sequence which is unique to the target sequence of that member, and (ii) one or more reverse primers that are complementary to the target sequences. The sample nucleic acids are then extended, preferably be PCR thermal cycling in the presence of suitable enzyme and nucleotide components, to form extended, preferably amplified target sequences.

The extended target sequences are then reacted under hybridization conditions with a set of electrophoretic tag (e-tag) probes, each probe having (i) an oligonucleotide portion that is complementary to one of the extension sequences, (ii) an electrophoretic probe having an electrophoretic mobility that is unique to a given extension sequences, and (iii) a linker joining the olignoucleotide portion and the electrophoretic probe. As in the previous methods described in the E-tag Patents, the linker is cleavable under selected conditions when the oligonucleotide portion of the probe is bound to a complementary target extension sequence.

The target sequences with bound probes are treated under the selected condtions, to release an e-tag reporter from each e-tag probe bound to a target sequence, the released reporters are separated electrophoretically, and the separated reporters are detected, to identify and, optionally, quantitate, target sequences that hybridized to the probes.

A. Exonuclease Cleavage

Figure 1B:
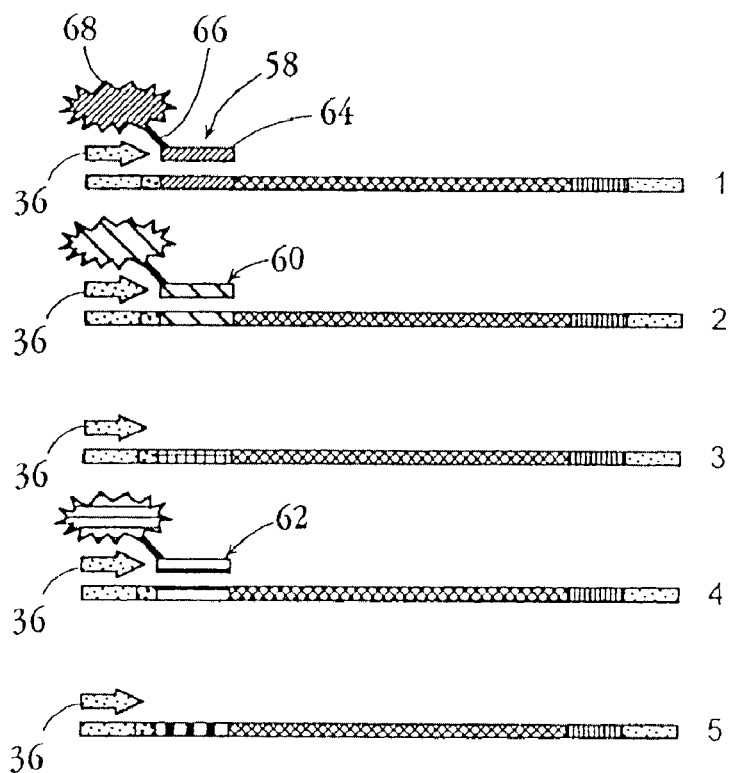
Figure 1C:
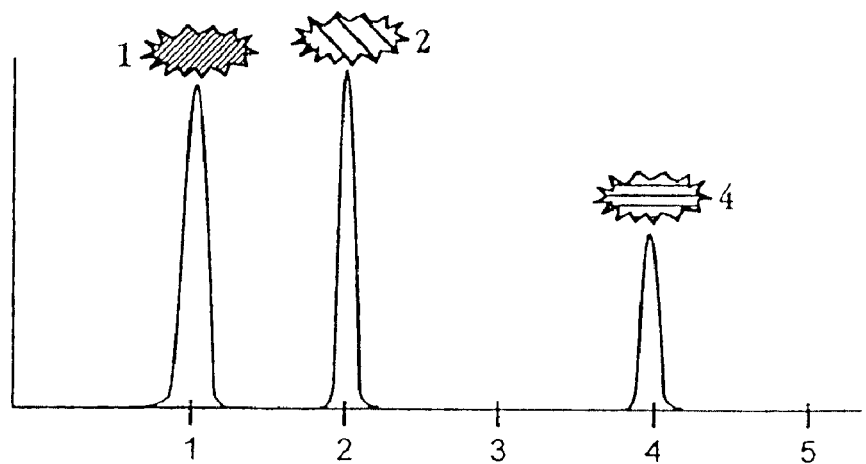

FIGS. 1A-1C illustrate basic steps in practicing the universal-probe method in accordance with one embodiment of the invention. FIG. 1A shows a double-stranded DNA fragment 20 composed of strands 20a, 20b, and containing a target sequence 22 of interest (for purpose of discussion, it is assumed that the target sequence is present on one strand—here, strand 20a—and the complement of the target sequence is present on the opposite strand). The target sequence of interest may be, for example, a particular sequence associated with a gene of interest, a SNP sequence of interest, a known mutation associated with a known genetic condition, and/or a known sequence associated with a known restriction fragment polymorphism. In addition, the sample being interrogated by the method typically contains multiple, e.g., 2-100 or more, different nucleic acids, and/or different regions of the same nucleic acid, each having a potential target sequence to be identified. For example, the sample may contain the DNA from one or more chromosomes, or from a digested portion of the genome, or the entire genome of an organism.

To the sample is added the set of forward universal e-tag primers, such as forward primers 24, 26 in FIG. 1A. Primer 24, which is representative, includes a target sequence 28 that is complementary to one of the known selected target sequences, such as target sequence 22, an extension sequence 30 which is unique to the target sequence of that probe, a spacer sequence 32, and a nested-primer sequence 34 complementary to a common-sequence nested primer 36. In the set of probes, each different probe member has a different target sequence and different associated extension sequence, preferably a common nested-primer sequence, and a spacer sequence that may or may not be common the different probes in the set. The target sequence, extension sequence, and nested-primer sequence are each of a length sufficient to form stable double-stranded duplex structures with complementary smaple nucleic acids, e-tag probes, and nested primers, respectively, and are typically at least 8, usually 12-20 or more bases in length.

Construction of the primers may be, for example, by conventional solid-phase synthesis, where (i) the target sequence of each forward primer is designed for base-sepcific hybridization to a known sample target sequence, (ii) the sequence of each extension sequence is designed for base-specific hybridization with the known oligonucleotide sequence in a set of e-tag probes, to be described below, and (iii) the sequence of the nested-primer sequence is selected for base-specific hybridization to the nested primer.

Also added to the sample is a one or more reverse primers, such as primer 40, that are complementary to a second target region downstream (3' with respect to) of the target region in each sample nucleic acid. In particular, each reverse primer contains a region, such as region 42 in primer 40, complementary to the second target region (which may be the same of different for different nucleic acids in the sample, and is associated with the second nucleic acid strand, such as strand 20b, in the nucleic acid). Also as shown, each reverse primer contains an extension region 44 which is common to all reverse primers, and preferably has the same sequence as the nested primer sequence. Construction of this set of primers is as above.

Addition of the above primer sets to the sample of DNA, followed by heat denaturation, primer annealing, and primer extension in the presence of a suitable DNA polymerase and all four dNTPs, followed by a second round of extension with the same primers form the opposite strand ends, is effective to extend the sample nucleic acids, as shown in FIG. 1A, to produce double-stranded nucleic acids, such as nucleic acid 46 having strands 46a, 46b, containing, at its 5' or 3' ends, all of the sequence regions of forward and reverse primers. These include, with reference to strand 46a, and proceeding in a 5' to 3' direction, sequences 48, 50, 52, and 22 corresponding to nested primer region 34, spacer 32, extension sequence 30, and target sequence 22, of primer 24, and at the 3' end of the amplified DNA strand, sequences 54,56 which are complementary to sequence 42, 44 of reverse primer 40. Optionally, the extended sample nucleic acids may be further amplified by conventional PCR, using either the combination of forward and reverse primers, or the nested primer(s) as the forward and reverse primers for PCR amplification.

Following extension, and optionally, amplification of the sample nucleic acids, the sample is mixed with a set of universal e-tag probes, such as probes 56, 60, 62, shown in FIG. 1B. As will be detailed below, each of the e-tag probes includes an oligonucleotide having a probe-specific sequence, such as sequence 64 in probe 58, that is complementary to a known one of the extension sequences in a forward primer probe, described above. This sequence is linked through a cleavable linker, such as linker 66 in probe 58, to an e-tag, such as tag 66 in probe 58, composed of a detection group, by which the tag can be detected, and a mobility modifier that imparts a unique separation characteristic, e.g., electrophoretic mobility, to that e-tag. The detection group may be either a fluorescent or other directly observable group, as described in several of the E-tag Patents, a ligand which is capable of binding to a reporter-labeled antiligand molecule, or may be a catalytic group which is able to catalyze a detectable reaction, as detailed, for example, in co-owned U.S. patent application for "Methods and Reagents for "Catalytic Multiplexed Assays," Ser. No. 60/294,821, filed May 26, 2001, incorporated herein by reference and attached hereto. As noted above, the linker is susceptible to cleavage by a selected cleaving agent, when the e-tag probe is hybridized to its complementary extended sequence in a sample nucleic acid.

After addition of the e-tag probes to the extended sample nucleic acids, and following denaturation and probe annealing to the sample strands, each sample containing an extended sequence complementary to an e-tag sequence will bind a given e-tag probe by base-specific hybridization, as indicated in FIG. 1B, showing sample nucleic acids 1, 2, and 4 with bound e-tag probes 58, 60, 62, repsectively, and sample nucleic acids 3 and 5 without bound probe. That is, the e-tag probes recognized three out of the five potential target nucleic acids in the sample.

In addition to the e-tag- probes, the sample mixture includes the nested universal primer 36 which hybridizes with the complementary 5'-end nested primer sequence in each of the extended nucleic acids as shown. The nested primer provides a substrate for a primer-dependent polymerase/exonuclease enzyme also contained in the mixture. Such enzymes are well known to those skilled in the art. In the presence of dNTPs, the enzyme functions to extend the nested primer until it reaches the 5'-end nucleotide of the target-hybridized oligonucleotide of the e-tag probe. The enzyme then functions as an exonuclease, cleaving the probe at the (typically, phosphodiester) intersubunit linkage between the 5'-end nucleotide (which is the linker in the probe) and the 5'-penultimate nucleotide (which is the 5'-end of the target-binding oligonucleotide moiety in the probe), releasing the e-tag containing a single linker nucleotide.

The released e-tag probes from the reaction are then separated, e.g., by electrophoresis. An electropherogram, shown in FIG. 1C, shows peaks corresponding, in electrophoretic mobility to e-tags 1, 2, and 4, indicating that the sample mixture contained sequences corresponding to 1, 2, and 4 in the original forward primer set, but not sequences corresponding to sequences 3 and 5. In addition, the amount of probe, determined for example, from area under the curve or peak height, may be used to quantiate the amount of a particular nucleic acid in the sample tested. It is understood that e-tag standards with known migration rates and amounts may be included in the e-tag mixtures for purposes of calibrating migration rates and amounts.

In summary, a set of specific primers are used to convert sample nucleic acid sequences of interest to a set of sequences corresponding to the oligonucleotide moieties of a universal e-tag probe set. The universal e-tag probe set, in turn, is used in primer-dependent exonuclease cleavage reactions to release, in a target-dependent manner, e-tags whose electrophoretic mobility can be used to determine the presence of absence of an associated original target sequences of interest. The invention thus allows any diverse group of target sequences to be interrogated and identified by a standard, universal set of e-tag probes, in a multiplexed reaction.

B. Restriction Endonuclease Cutting

FIGS. 2A-2C illustrate a second general embodiment of the method, in which cleavage of target-bound e-tag probes, to release associated e-tags, is by endonculease cutting. The forward primers employed in the method above in that the extension sequence includes, adjacent its 5'-end (i.e., just downstream of the spacer sequence) a selected restriction endonuclease cutting sequence. Similarly, the e-tag probes include, as the linker between the oligonucleotide binding moiety and the releasable e-tag, a small number of nucleotides whose sequence is complementary to the above restriction site sequence. Selection of suitable restriction site cutting sequences is given in Example 2 below. The forward and reverse primers, and oligonucleotide portion of the e-tag probe, can be constructed as indicated above.

Restriction enzymes are employed in a variety of techniques employing nucleic acids, and are typically used to cleave a nucleic acid target at a particular location. such restriction enzymes recognize and cleave within a specific sequence in a target nucleic acid. Table 1* provides a listing of common restriction enzymes and their recognition sites. Such restriction enzymes and conditions for their use are generally known to those skill in the art and are commercially available, for example from Promega Corp. (Madison, Wis.). Table A below gives the restriction-site sequences for several restriction endonculeases.

TABLE A

Restriction Enzyme Recognition Sites

| Restriction Enzyme | Recognition Site | Restriction Enzyme | Recognition Site |
|---|---|---|---|
| Aat II | GACGT/C | Hsp92I | GR/YCGC0 |
| Acc I | GT/MKAC | Hsp92II | CATG/813 |
| Acc III | T/CCGGA | I-PpoI | CTCTCTTAA/GG-TAGC |
| Acc65 I | G/GTACC | KpnI | GGTAC/C |
| AccB7 I | CCANNNN/NTGG | MboI | /GATC |
| Age I | A/CCGGT | MluI | M/CGCGT |
| AIu I | AG/CT | MspI | C/CGG28 |
| AIw26 I | GTCTG(1/5) | MspAI | CMG/CKG5 |
| AIw44 I | G/TGCAC | NaeI | GCC/GGC |
| Apa I | GGGCC/C | NarI | GG/CGCC |
| Ava I | C/YCGRG | NciI | CC/SGG14 |
| Ava II | G/GWCC | NcoI | C/CATGG |
| BamH I | G/GATCC | NdeI | CA/TATG |
| Ban I | G/GYRCC | NdeII | /GATC |
| Ban II | GRGCY/C | NgoMIV | G/CCGGC |
| Bbu I | GCATG/C | NheI | G/E-TAGC |
| BcI I | T/GATCA | NotI | GC/GGCCGC |
| BgI I | GCCNNNN/NGGC | NruI | TCG/CGA |
| BgI II | A/GATCT | NsiI | ATGCA/T4 |
| BsaM I | GATTGCN/ | PstI | CTGCA/G8 |
| BsaO I | CGRY/CG | PvuI | CGAT/CG |
| Bsp1286 | GDGCH/C | PvuII | CAG/CTG5 |
| BsrBR I | GATNN/NNATC | RsaI | GT/AC13 |
| BsrS I | ACTGGN/ | SacI | GAGCT/C |

TABLE A-continued

Restriction Enzyme Recognition Sites

| Restriction Enzyme | Recognition Site | Restriction Enzyme | Recognition Site |
|---|---|---|---|
| BssH II | G/CGCGC | SacII | CCGC/GG |
| Bst71 I | GCAGC(8/12) | SaII | G/TCGAC |
| Bst98 I | C/TTAAG | Sau3AI | G/ATC16 |
| BstE II | G/GTNACC | Sau96I | G/GNCC4 |
| BstO I | CC/WGG | ScaI | AGT/ACT |
| BstX I | CCANNNNN/NTGG | SfiI | GGCCNNNN/NGGCC |
| BstZ I | C/GGCCG | SgfI(a) | GCGAT/CGC |
| Bsu36 I | CC/TNAGG | SinI | G/GWCC5 |
| Cfo I | GCG/C | SmaI | CCC/GGG |
| Cla I | AT/CGAT | SnaBI | TAC/GTA |
| Csp I | CG/GWCCG | SpeI | A/E-TAGT |
| Csp45 I | TT/CGAA | SphI | GCATG/C |
| Dde I | C/TNAG | SspI | AAT/ATT0 |
| Dpn I | GmeA/TC | StuI | AGG/CCT |
| Dra I | TTT/AAA | StyI | C/CWWGG0 |
| EcIHK I | GACNNN/NNGTC | TaqI | T/CGA21 |
| Eco47 III | ACG/GCT | Tru9I | T/TAA |
| Eco52 I | C/GGCCG | VspI | AT/TAAT7 |
| EcoICR I | GAG/CTC | XbaI | T/E-TAGA |
| EcoR I | G/AATTC | XhoI | C/TCGAG |
| EcoR V | GAT/ATC | XhoII | R/GATCY1 |
| Fok I | GGATG | XmaI | C/CCGGG |
| Hae II | RGCGC/Y | XmnI | GAANN/NNTTC |
| Hae III | GG/CC | | |
| Hha I | GCG/C | | |
| Hinc II | GTY/RAC | | |
| Hind III | A/AGCTT | | |
| Hinf I | G/ANTC | | |
| Hpa I | GTT/AAC | | |
| Hpa II | C/CGG | | |

FIG. 2A shows a sample with five single-strand nucleic acics having target sequences of potential interest. The nucleic acid strands have, at this stage, been extended and amplified with forward and reverse primers, as described above, and with the forward-primer modification just described. Thus, for example, the first nucleic acid strand, indicated at 70, includes (i) a target sequence 71 of potential interest, (ii) an unique extended sequence 72 associated with and unique to the target sequence, and having a selected restriction cutting site adjacent its 5' (upstream) end, a spacer sequence 74 and a universal nested primer sequence 76.

To the amplified, extended sample nucleic acids is added a set of e-tag probes like those described above, having a target-binding oligonucleotide moiety capable of hybridizing to a complementary extension sequence in one of the extended sample nucleic acids, a releasable e-tag whose separation characteristics can be associated with a given sequence, and a linker joining the two and containing the selected restriction site cutting sequence. The nucleotide linker in this method, which includes the restriction-site sequence, also hybridizes, along with at least a portion of the probe's oligonucleotide moiety, to the extended target sequence.

The e-tag probes are, as above, added to the sample reaction mixture and hybridized by heat-denaturation and probe annealing, yielding a mixture of sample nucleic acids, such as nucleic acid strands 1, 2, and 4 in FIG. 2B, that have bound e-tag probes, and sample nucleic acids, such as strands 3 and 5, that do not have a probe-recognized sequence. Since restriction endonculease cutting requies double-stranded fragments, only those probes that are hybridized to a target-specific sequence will yield released e-tag when exposed to the selected endonuclease.

If only a single round of probe hybridization and e-tag release is desired, the extended, amplified nucleic acids in the sample may be formed from non-methylated forward primers, yielding strands with non-methylated extended sequences. Where it is desired to use the sample strands for repeated e-tag probe binding and e-tag release, the nucleotides in the cutting site of the extended sequence must be methylated, thus limiting endonculease cutting to the single probe strand at the cutting site. This can be accomplished readily by synthesizing the forward primer probes used in fragment extension and amplification, to contain methylated bases at the nucleotides defining the restriction cutting site.

Following treatment with the selected restriction endonculease to release e-tags from target-bound primers, the released e-tags are separated, e.g., electrophoretically. An electropherogram, shown in FIG. 2C, like the one in FIG. 1C, shows peaks corresponding in electrophoretic mobility to e-tags 1, 2, and 4, indicating that the sample mixture contained sequences corresponding to 1, 2, and 4 in the original forward primer set, but not sequences contained in nucleic, acids 3 and 5. As above, the relative or absolute amount of separated e-tags, reflecting the amount of associated target sequences, can be also determined from peak characteristics.

As in the first-described embodiment, this embodiment of the invention allows any diverse group of target sequences to be interrogated and identified by a standard, universal set of e-tag probes, in a multiplexed. In addition, the forward primers and e-tag probes can be readily designed to include a selected restriction endonculease site in the sequence of the e-tag probe linker, allowing e-tag probe cleavage by any of a number of different endonculeases.

C. Cleavage by Proximity Sensitizer

In a third general embodiment of the method, illustrated in FIGS. 3A-3D, release of e-tags from target-bound e-tag probes is effected by a short-lived chemically active species, such as singlet oxygen, which is generated and present only in the neighborhood of a target-bound probe, and is therefore capable of acting only on such bound probes.

The forward, reverse and universal nested primers employed in the method are substantially identical to those described with respect to the first embodiment (FIGS. 1A-1C), except that the nested primer contains at its 3' end, a sensitizer group capable of generating the desired active species, e.g., singlet oxygen, when exposed to an activating stimulus, e.g., light.

The e-tag probes used in the method differ in at least one respect from the e-tag probes described above: the linker joining the oligonucleotide moiety and e-tag is a chemical group, such as an olefin linkage, which is susceptible to cleavage by the chemically active species. For purposes of illustrating e-tag probes of a type that are particularly suited for this embodiment of the invention, but is also adaptable to the other embodiments described above, this section will also consider e-tag probes (i) containing multiple e-tags linked to a branched structure, and (ii) having a catalytic detection group. By the same token, other the e-tag probes are also suitable for this embodiment of the invention, the basic requirement being that the probe have (i) an oligonucleotide moiety for binding to an extended target sequence, (ii) a releasable e-tag, or e-tag,s and a linker or linkers which are susceptible to cleavage by the chemically active species.

FIG. 3A shows a sample with three single-strand nucleic acids having target sequences of potential interest. The nucleic acid strands havve, at this stage, been extended and amplified with forward and reverse primers, as described above. Thus, for example, the nucleic acid strand designated "target 1" and indicated at 80, includes (i) a target sequence 81 of potential interest, (ii) a unique extended sequence 82 associated with and unique to the target sequence, a spacer sequence 84 and a universal nested primer sequence 86.

To the amplified, extended sample nucleic acids is added a set of e-tag probes, such as probes 88, 90 having an oligonucleotide moiety capable of hybridizing to a complementary extension sequence in one of the extended sample nucleic acids. As shown, the added e-tag probes recognize targets 1 and 2 in the sample, but not target 3. Also added to the reaction mixture is a nested universal primer 102 having a sensitizer group 104 carried at the 3'-end of the primer. As can be appreciated, the spacer sequence in the target is such as to place the senitizer group proximate the linker(s) in the e-tag probes. Typically, the spacer sequence is 0-4 nucleotides—that is, the spacer sequence may be absent or contain only a few bases.

Agents capable of cleaving the linking group of an e-tag probe in order to release a detectable e-tag reporter include, but are not limited to, short-lived chemical species and/or species produced by photoactivation. Exemplary species include singlet oxygen, hydrogen peroxide, NADHG, and hydroxyl radicals, phenoxyradical, superoxide, and the like.

Photoexcitation of chromophores in the presence of oxygen often leads to the product of single oxygen by a bimolecular energy-transfer process involving the excited chromophore and ground-state triplet oxygen. This process is referred to as photosensitization and the excited chromophore is designated a sensitizer.

In general, the generation of singlet oxygen may be described as a multi-step process including the absorption of light by a sensitizer, formation of a triplet state, triplet trapping of oxygen and energy transfer from the triplet sensitizer to oxygen.

Construction, structures, and propeties of such photosensitizers, and systems for development of detectable reaction with separated electrophoretic tag reporters, are described in co-owned U.S. Patent Application for "Determination of Target Analytes Employing Cleavabale Electrophoretically Tag Reagents," Ser. No. 60/292,548, filed May 21, 2001, incorporated by reference and attached hereto.

E-tag probe 88, which is representative includes oligonucleotide 92 complementary to the extended target sequence and a branched structure, e.g., polymer 94, covalently attached to the oligomer. The branched polymer includes multiple branches, distal ends of which are each linked by a cleavable linker to a releasable e-tag, such as e-tag 98, as described in co-owned U.S. patent application for "Determination of Target Analytes Employing Cleavable, Electrophoretic Tagged Reagents," reference above. As noted above, the linkers are susceptible to cleavage by the active chemical agent generated by the sensitizer. e.g., singlet oxygen. The releasable e-tags may have detectable groups, or in the present embodiment, are groups capable of catalyzing a detectable reaction, as detailed in above-cited U.S. patent application Ser. No. 60/293,821.

After hybridizing the e-tag probes to the single-stranded target strands, the mixture is treated, e.g., by exposure to light, to produce active cleaving agent. As can be appreciated from FIG. 3B, this treatment is effective to release tags only from probes that are proximate to sensitizer groups, that is, probes that are hybridized to target sequences. Following this treatment, the reaction mixtures thus contains released e-tags, such as e-tags 98, 100, corresponding to target-bound probes, and intact probes (with unreleased e-tags) where no probe-target binding occurred.

Figure 3C:
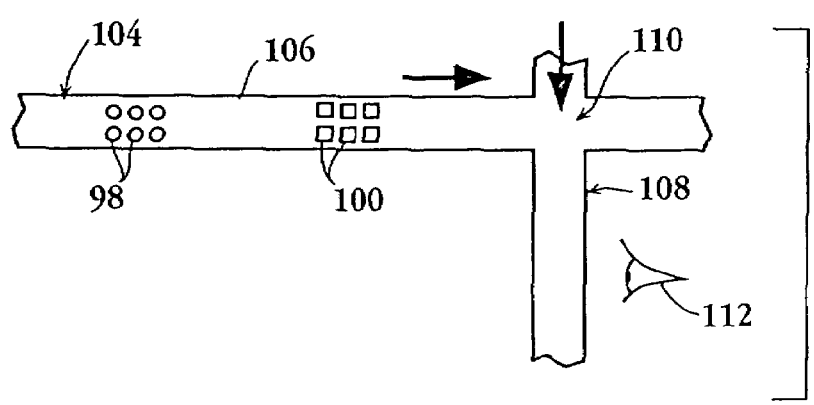
Figure 3D:
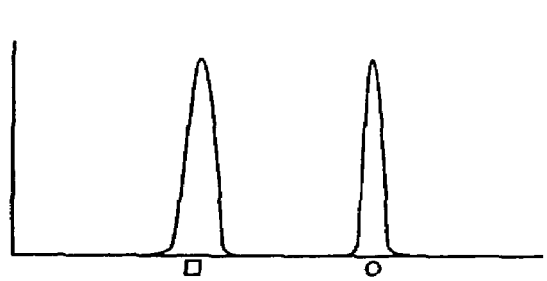

FIG. 3C illustrates portions of a capillary electrophoresis device 104 suitable for electrophoretic separation and catalytic detection of e-tags. The device includes a capillary electrophoresis tube 106 which is intersected, near its downstream end, with a reagent-supply channel 108, forming an intersection 110 at which separated e-tags are mixed and react with the reagents, to produce a detectable color reaction. The color components of the reaction, in turn, are drawn electrokinetically or by fluid pressure within channel 108 toward a detector 112, where detection of the reaction components occurs. The detector output is the electrophorogram shown in FIG. 3C. From the known elapsed time to detection, the identity of the corresponding catalytic e-tag is determined, and from this, the identity of the target sequence in the sample material confirmed. Assuming the amount of e-tag is rate limiting in the catalytic reaction, the amount of e-tag can also be determined.

The advantages of this embodiment are the same as those noted above. In addition, the branched e-tag probe described provides signal amplification by virtue of the multiple e-tags released from each target-bound probe. The catalytic e-tag provides additional amplification, since each released e-tag is capable of catalyzing a large number of color-generating reaction events.

D. Probe and Primer Sequence Considerations

Target specific amplification serves to generate an e-tag probe recongnition site, which allows for specific binding of an e-tag probe and release of a detectable e-tag reporter. The selection of the nucleic acid target and the universal e-tag primer sequence will affect the stringency employed during the primer extension, particularly at the stage of hybridization. In a substantial number of samples, the DNA will be heterozygous for target nucleic acid sequence rather than homozygous. In such cases, it is important to avoid false positives which may be detected when the universal e-tag primer amplifies the target followed by secondary amplification using the universal component of the primer and binding of an e-tag probe to the e-tag recognition sequence. The reliability of the results may be increased by simultaneous analysis of both alleles for a given gene locus, e.g., the wild type and mutant alleles of a SNP, as exemplified in FIGS. 12A-12G. Where the target nucleic acid is homozygous for the prevalent sequence, it is also important that the universal e-tag primer does not bind to give a false positive. Therefore, the different in $T_m$ between the specific primer and universal primer components of a universal e-tag primer, will usually be from about 4 to 8° C., more usually at least about 4 to 6° C., under the conditions of primer extension. The reliability of the methods of the invention may be further increased by the use of the allele specific primers contains a deliberate mismatch in one of the 3 bases at the 3' terminal end. For example, a primer for the MTHFR C677T SNP may be designed with an additional mismatch 4 nucleotides from the 3' end, e.g.

| | | |
|---|---|---|
| Wild type primer | GAAGGAGAAGGTGTCTGCGGTAGC | (SEQ ID NO:1) |
| Mutant primer | GAAGGAGAAGGTGTCTGCGGAAGT | (SEQ ID NO:2) |
| Template DNA | GAAGGAGAAGGTGTCTGCGGGAGN | (SEQ ID NO:3) |

E. Exemplary Reaction Conditions

E1. First Round Amplification

A first round amplification reaction, e.g. PCR, may be carried out using genomic DNA, mRNA, cDNA or another similar template target source in which a sequence is to be detected. Amplification begins with the 3' portion of a universal e-tag primer hybridizing with the target DNA and amplifying the intervening DNA sequence. On subsequent rounds of amplification, the tailed portion of a universal e-tag primer is complemented and the outer nested primer sequences begin to amplify the products of the first round amplification. This amplification reaction results in the generation of a sequence specific e-tag probe binding site immediately 3' of the extending outer PRC primers.

The primer extension reaction is typically accomplished using a primer driven amplification technique such as PCR. PRC is described in U.S. Pat. Nos. 4,683,195 and 4,683,202 to Mullis and Mullis et al. and Saiki, et al., Science 239: 487-491, 1988 and is carried out by introducing a molar excess of two universal e-tag primers complementary (one of which is target specific) to respective strands of a double-stranded target sequence into a sample, denaturing the sample and allowing complementary sequence to hybridize. Following hybridization, the primers are extended with a polymerase to form complementary strands. The steps of denaturation, hydridization, and primer extension are repeated until appropriate amplification of the target sequence is achieved. The primer extension reaction is furhter described below in section.

E2. Second Round Amplification And Reaction With An e-tag Probe

The first round of amplification reaction results in the generation of a sequence specific e-tag probe binding site immediately 3' to the extending outer PCR primers. Upon specific binding of an e-tag probe to this site, cleavage occurs and serves to displace a 5' e-tag reporter, which is detectable. Following electrophoretic separation, the signal from each e-tag reporter may be correlated with the nucleic acid target sequence that was amplified. This reaction process can be repeated or run in parallel for any number of desired targets, limited only by the number of available unique detectable labels and e-tag probe binding sequences.

In general, a pool of cleaved e-tag reporter molecules is collected for analysis, e.g., by capillary electrophoresis.

Given that each e-tag reporter has a unique electrophoretic mobility, the pattern of peaks generated provides a code for the sequences present in the original sample which typically contains a target mixture.

In one exemplary representation of the invention, a universal e-tag primer and a universal nested primer specifically bind to a nucleic acid target, followed by amplification to yield a template which includes a recognition site for an e-tag probe. The e-tag probe specifically binds to the corresponding recognition site (also called the e-tag recognition sequence or target) and acts together with a universal nested primer to amplify the target resulting in cleavage to yield a detectable e-tag reporter (FIG. 10)

Figure 11:
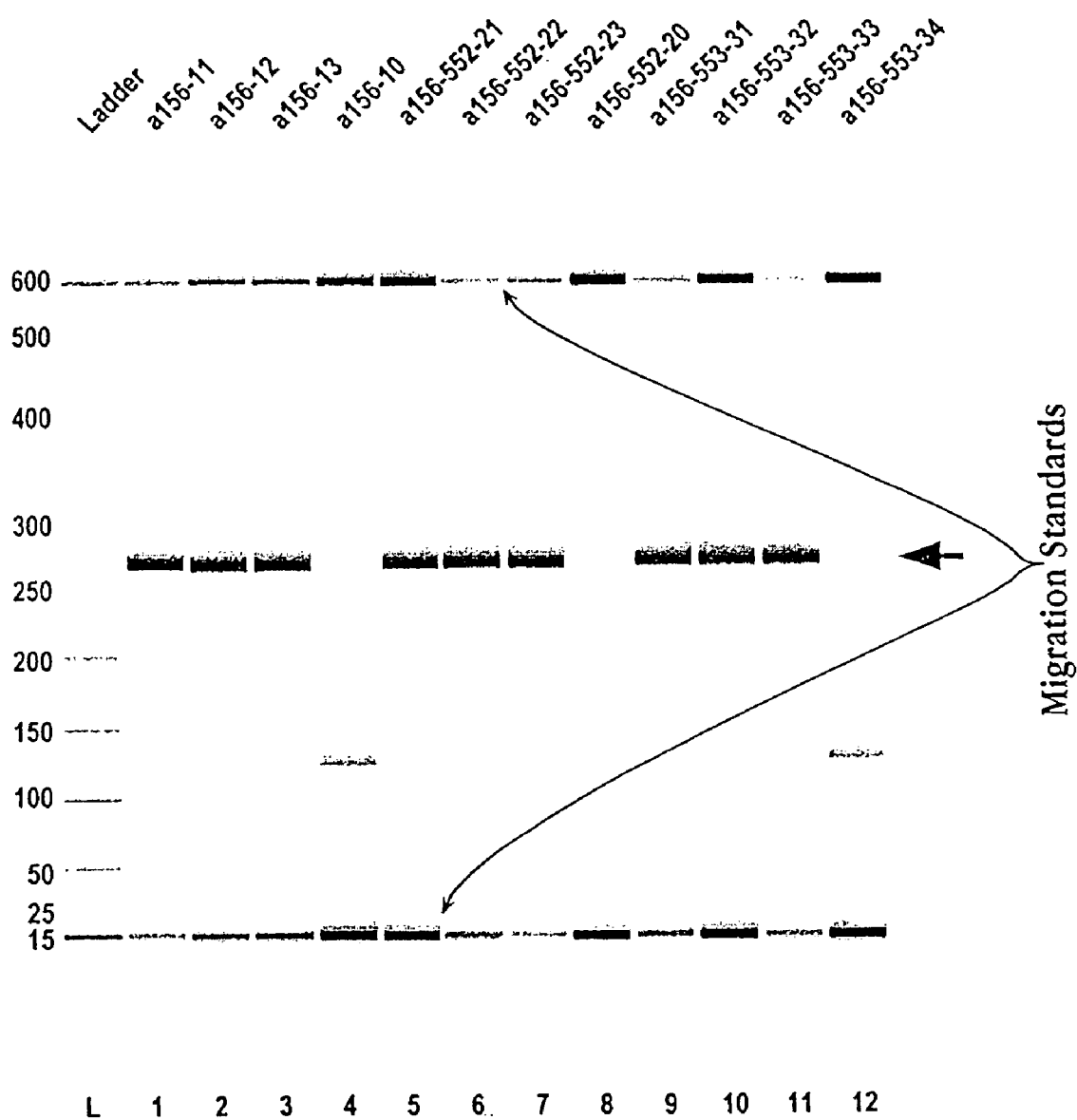
FIG. 11 provides an image from an Agilent 2100 Bio-Analyzer showing the PCR products obtaine dusing universal e-tag primers and e-tag probes specific for wild type and mutant targets in a competitive assay format (lanes 1-4); a non-competitive assay format including only the a156CT-eR10 TET labeled e-tag probe specific for the wild type amplification product (lanes 5-8); or non-competitive assay format including only the a 156CT-eR20 TET labeled e-tag probe specific for the mutant amplification product (lanes 9-12). Template DNA previously characterized as NA17001 (mutant/mutant; lanes 1, 5 and 9); NA17002 ( wild type/wild type; lanes 2, 6 and 10); NA17003 (wild type/mutant; lanes 3, 7 and 11) and water (lanes 4, 8 and 12) as a negative control was evaluated under each set of conditions. The MTHRF PCR product is approximately 270 bp as indicated by an arrow in the figure.
Figure 12A:
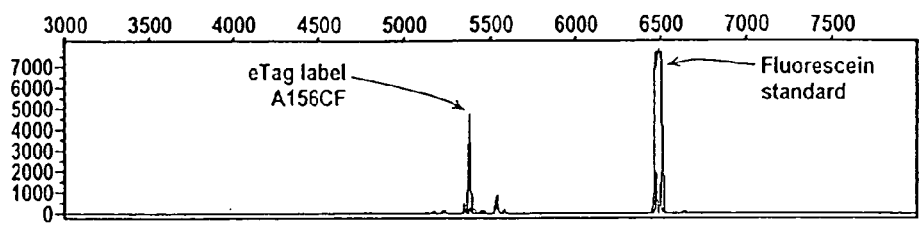
FIGS. 12A-12G are electropherograms which illustrate e-tag-reporter detection by capillary electrophoresis (CE) using an ABI Prism® 3100 genetic analyzer for a single SNP (MTHFR C677T) using a universal e-tag primer and e-tag probe specific for wild type and mutant targets in a single reaction mix at the same time. The figures present electropherograms which illustrate the results of analysis of NA17001 DNA which is homozygous for the MTHRF C677T mutant allele (mutant/mutant.
Figure 12B:
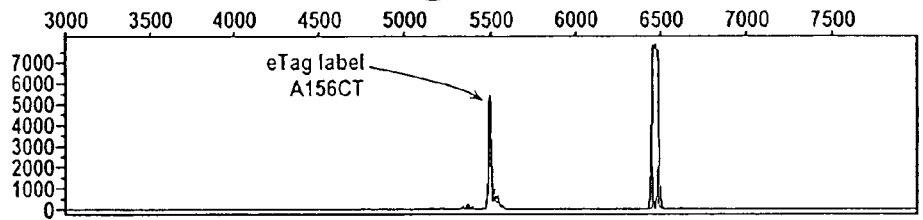
Figure 12C:
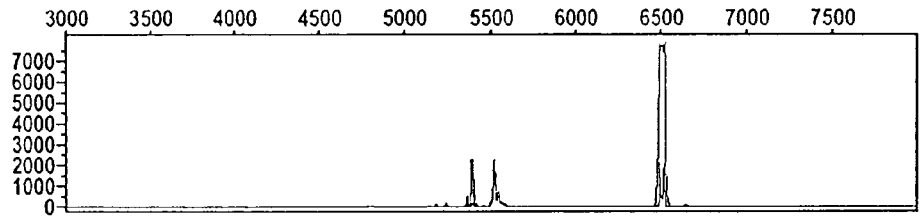
Figure 12D:
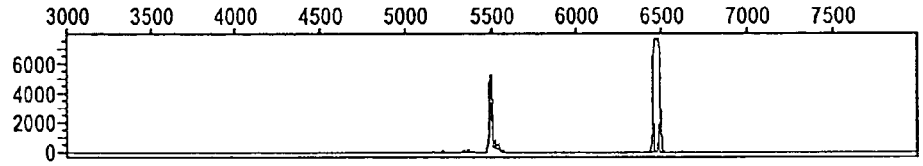
Figure 12E:
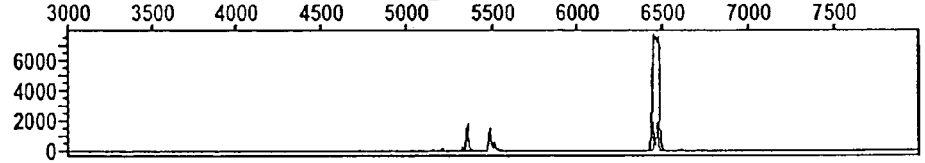
Figure 12F:
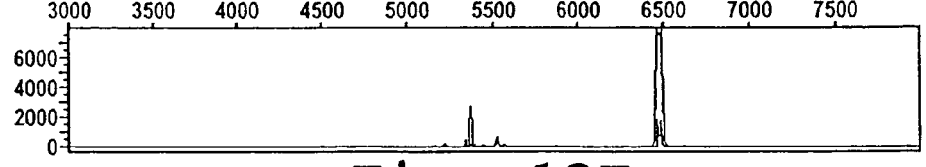
Figure 12G:
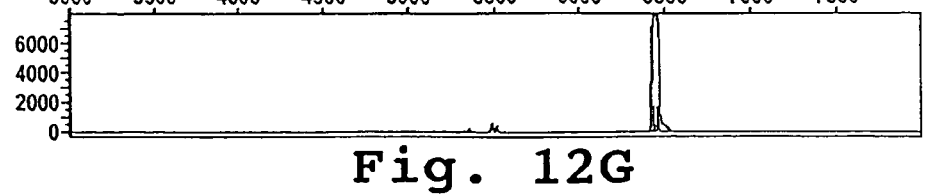
Figure 13A:
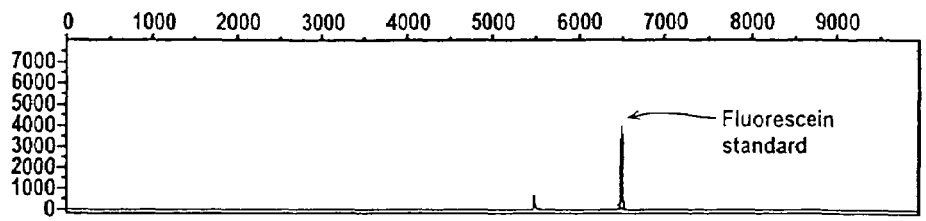
FIGS. 13A-13F are electropherograms illustrating the results of a test for the specificity of e-tag primers by CE using an ABI Prism® 3100 Genetic Analyzer for a single SNP (MTHFR C677T) using a non-competitive universal e-tag assay format, where
Figure 13B:
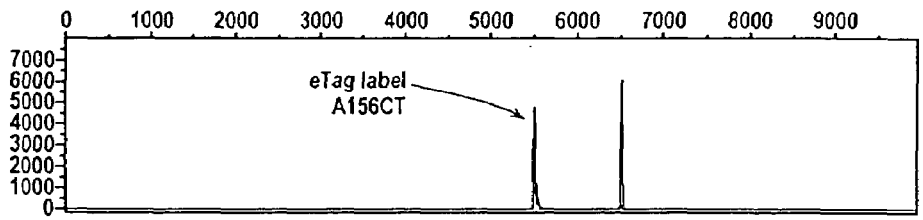
Figure 13C:
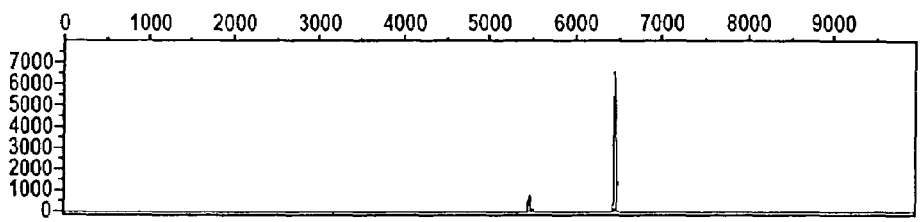
Figure 13D:
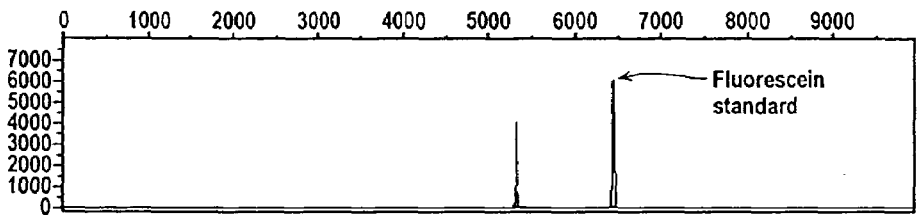
Figure 13E:
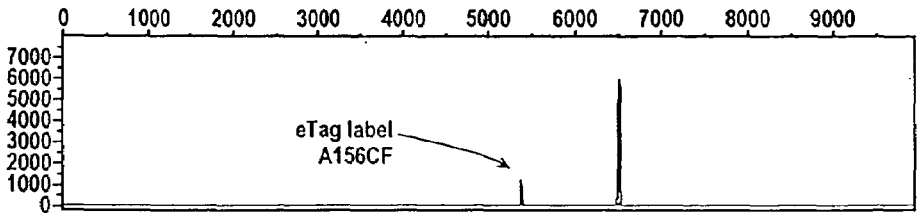
Figure 13F:
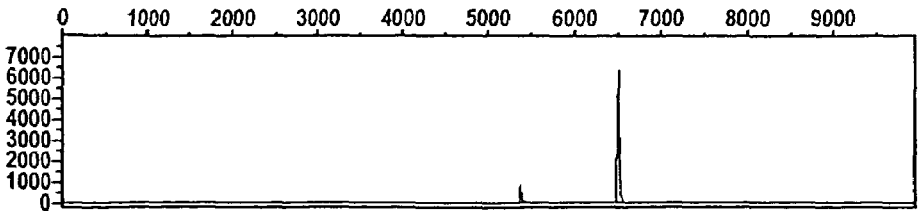

In another exemplary representation of the invention, a forward universal e-tag primer and a reverse primer specifically bind to a nucleic acid target, followed by amplification to yield template nucleic acid, which includes a recognition site for a nested universal primer that has an e-tag moiety attached at the 5' end. In this case, cleavage to release an e-tag reporter will take place only if the e-tag labeled primer becomes incorporated in the amplification product. (FIG. 11).

E3. Cleavage of e-tag Probes to Generate e-tag Reporters.

Cleavage typically occurs as the result of binding of the e-tag probe to the e-tag recognition site generated by amplification of a target nucleic acid sequence using a universal e-tag primer of the invention. The cleavage is facilitated by a cleaving agent or cleavage means such as a 5' exonuclease; a restriction enzyme; an RNase; a short-lived chemical speicies such as singlet oxygen; hydrogen peroxide, NADH, and hydroxyl radicals, phenoxyradical, superoxide, and the like; a peptidase; an esterase; a reducing agent; or an oligosaccharide hydrolase.

There are a number of genetic analyses that involve cleavage of the phosphodiester bond of a nucleic acid sequence following hybridization to a complementary sequence. For the most part, the initial step takes place in solution, although one may have one or more reagents bound to a solid support in the first and succeeding stages of the determination. One technique is described in U.S. Pat. Nos. 5,876,930 and 5,723,591, wher a primer and a probe are bound to a target sequence and by extending the primer with a DNA polymerase having 5'-3' nuclease activity, the terminal nucleotides are cleaved as the polymerase processes along the target DNA. By having an e-tag probe bound to the terminal and/or internal nucleotide(s), the e-tag reporter will be released when the target nucleic acid is present.

F. Exemplary microfluidics Devices for Practicing the Method

Figure 4:
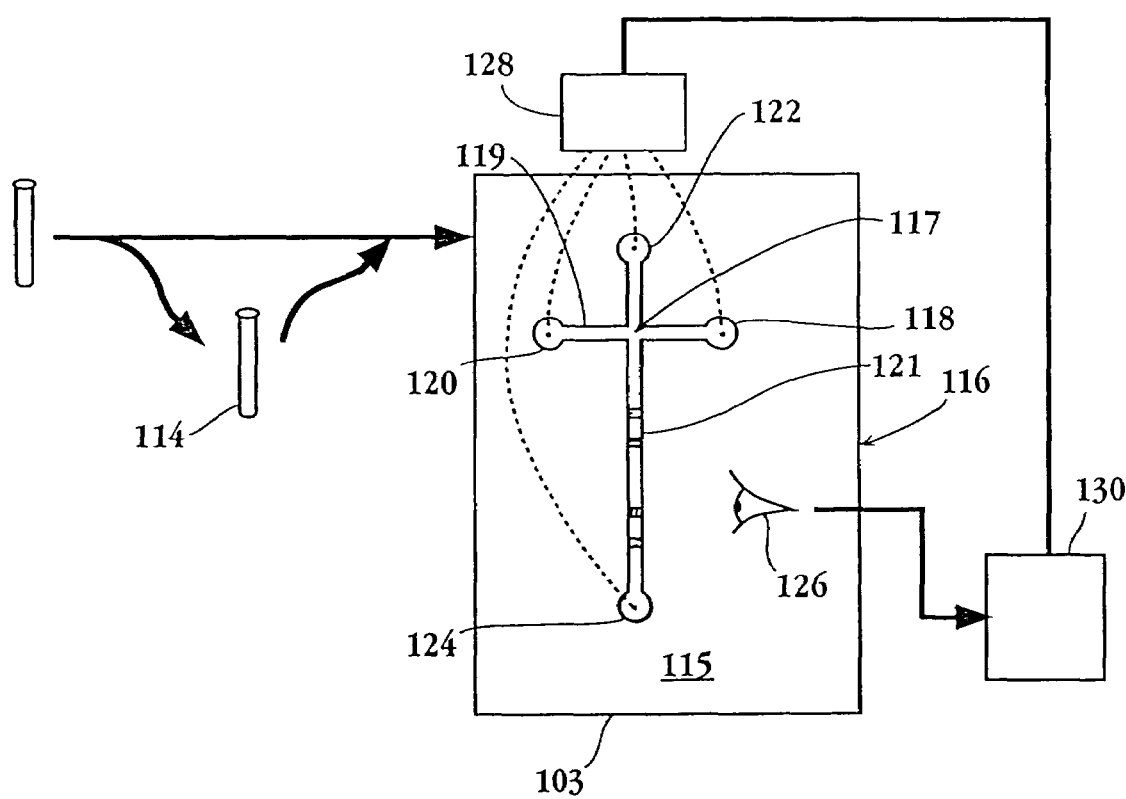
FIG. 4 illustrates apparatus used in practicing method of the invention.

The methods of the present invention involve an initial sample-treatment step in which released e-tags are generated, and a subsequent electrophoretic separation step. In the assay device shown in FIG. 4, the initial assay, which may invovle sample extension/amplification, e-tag probe binding to sample nucleic acids, and e-tag release, is carried in a separate sample volume or well, such as indicated at 109. The electrophoretic separation is then carried out in a microfluidics device 116 of the type known in the art. The device generally includes a substrate or card 115 117 having formed therein, a microstructure having an enclosed side channel 119 terminating at reservoirs 118, 120, and an enclosed separation channel 121 terminating at reservoirs 122, 124. The two channels intersect to form a channel loading region 117.

In operation, sample (typically containing released e-tags) is loaded in reservoir 118, and from here moved electrokinetically into sample-loading region 117 by applying a voltage potential across reservoirs 118, 120. After loading, a voltage potential is applied across reservoirs 122, 124, to electrophoretically separate released e-tags contained in the sample-loading region inthe device. The separated e-tags are detected by a detector 126, which inputs a control unit 130, for generating suitable output, e.g., an electropherogram and/or for automated peak analysis based on migration times. The control unit alos control a voltage source 128 operatively connected to the four device reservoirs.

Figure 5A:
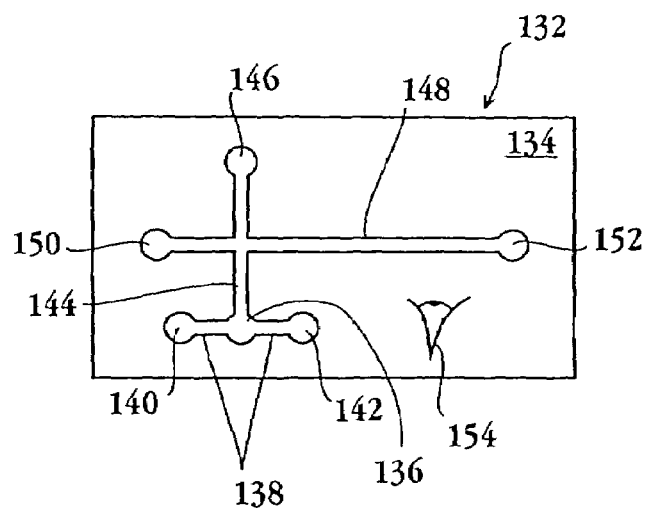
FIGS. 5A-5C illustrate a microfluidics sample-handling device for carrying out small-volume assays in accordance with the invention, with exemplary reservoir voltages applied during sample loading and sample separation indicated in FIGS. 5B and 5C, respectively.
Figure 5B:
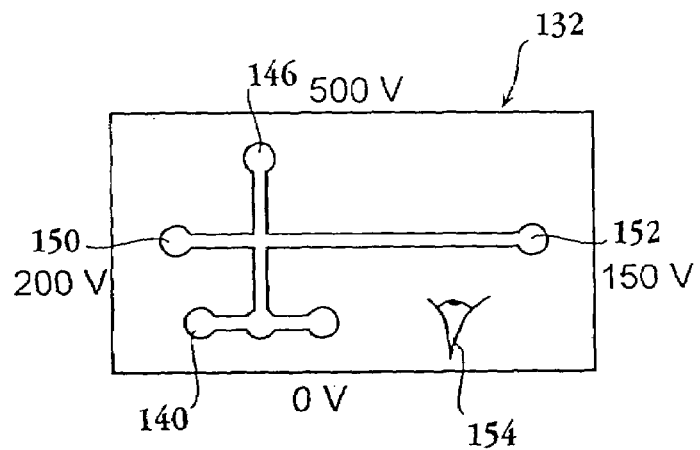
Figure 5C:
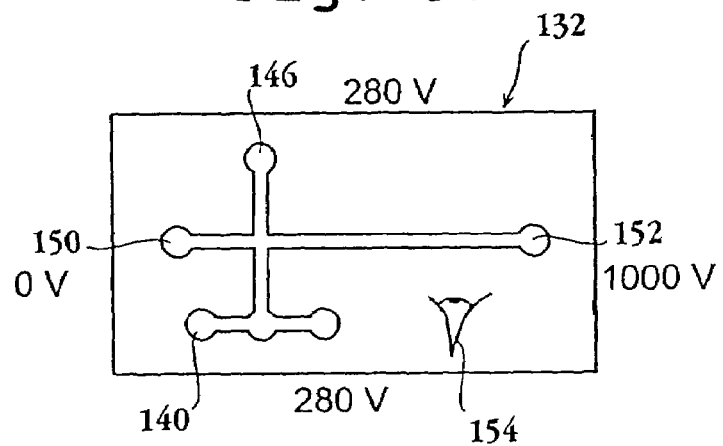

FIGS. 5A-5C illustrate another microfluidics device 132 for carrying out the method of the invention, and in particular, for carrying out both the sample-treatment and separation steps in a single device. The device generally includes a card 134 having formed therein, a microstructure containing an open sample well 136 connected by enclosed channels 138 to open reservoirs 140, 142, as detailed, for example, in PCT application WO 00/67907, published 16 Nov. 2000, and incorporated herein by reference. The device includes a channel microstructure having an open sample well 136 which is in fluid communication with a pair of open reservoirs 140, 142, via enclosed channels 138. One of these reservoirs, e.g., reservoir 140, serves as an electrode reservoir, and is referred to herein as a first reservoir.

The sample well, in turn, communicates with one terminus of a side channel 144 which terminates at its other end in a second reservoir 146. The side channel intersects a separation channel 148 at an intersection 146 which forms a sample loading region in the separation channel.

In operation, sample treatment steps are carried out in a microvolume in sample well 136. The sample treatment steps may include (i) nucleic acid amplification by PCR, using the forward and reverse probes described above, (ii) addition of the set of etag probes to the nucleic acid sample, and (iii) release of e-tags from the e-tag probes by a binding-dependent cleavage reaction as described above, or only reactions (ii) and (iii) or only reaction (iii). During the reaction step(s), evaporative loss from the sample is replenished by liquid flow from reservoirs 140, 142 into the well through channels 138, to maintain the sample volume substantially constant.

Following sample treatment to produce one or more released e-tags corresponding to one of more selected nucleic acid target sequences, the sample solution, or charged e-tag components in the sample, are moved from the sample well into the sample-loading region in the separation channel. The e-tag movement may be accomplished by placing a pressure differential across reservoirs 140, 146, or by applying a potential difference across the reservoirs, to move the sample or charged sample components electrokinetically, e.g., by electro-osmotic flow or electrophoretic migration. The potential difference is applied by a voltage source operatively connected to electrodes placed in the electrodes. FIG. 5B illustrates typical voltages applied to the four electrodes during sample loading. The relatively lower voltage potentials across reservoirs 150, 146 and 152, 146 is effective to prevent sample diffusion at the sample-loading zone by a fluid pinching effect.

With released e-tag components loaded in the loading zone, the voltages applied to the four reservoirs are adjusted, as indicated in FIG. 5C, to move charged e-tag components in a downstrream direction (to the right in the figure), along the separation channel, where the individual e-tags are separated electrophoretically. E-tag detection is by a suitable detector, such as detector 154, positioned adjacent the downstream end of the separation channel. The detector is connected to a suitable recording device for generating electropherograms, such as discussed below with respect to FIGS. 12-14, used in assay analysis.

III. Universal-Primer e-tag Probe Kit

In accordance with another aspect, the invention includes a kit for detecting each or any of a plurality of known, selected nucleotide target sequences. The kit generally a set of forward universal e-tag primers, one or more reverse primers, and a set of e-tag probes. The kit may additionally include cleaving reagents for effecting target-dependent and, optionally, target-independent e-tag release, as described above.

A. Forward and Reverse Primers

The construction and synthesis of the forward and reverse primers for various embodiments of the invention will be appreciated from the discussion in Section II above, and from the example 2 below, which provides exemplary sequences from A above, of primer will z construction. Briefly, two priming sequences are included when carrying out the universal e-tag methodology of the invention such that, each one complements the consensus sequence throughout its length until the 3' end of the oligonucleotide. It is preferred that the ultimate 3' position of the sequence specific portion of each primer be made complementary to one form of a sequence variant. A second "downstream" generic extension sequence is designed for the proposed cycling (PCR) conditions. The sequences specific set of oligonucleotide probes each have a unique sequence (unrelated to the target sequence) of approximately 30 bases 5' of the target specific primer component that is an e-tag probe extension sequence, 5' to this sequence is a short nucleotide "spacer" sequence (that is at least 2, typically 2-8, and preferably 6 nucleotides in length) linked to an approximately 20 base pair nested or universal primer sequence. The nested PCR primer sequence is also used to tail the generic 'downstream' target specific PCR primer.

Following design, universal e-tag primer sequences and the target binding component of an e-tag probe may be synthesized by any convenient means, using an automated synthesizer, as further described in the Examples.

See, e.g., Matthews, et al., Anal. Biochem. (1988) 169: 1-25; Keller, et al., "DNA Probes," $2^{nd}$ edition (1993) Stockton Press, New York, N.Y.; and Wetmur, CRITICAL REVIEWS IN BIOCHEMISTRY AND MOLECULAR BIOLOGY (1991) 26:227-259.

B. e-tag Probe Set

As indicated above, an electrophoretic (e-tag) probe for use in practicing the invention has four basic components: (i) a detection group or moiety, (ii) a charged mobility group, (iii) a target-binding moiety, and (iv) a linking group that links the mobility modifier and detection group to the target-binding moiety.

Figure 6:
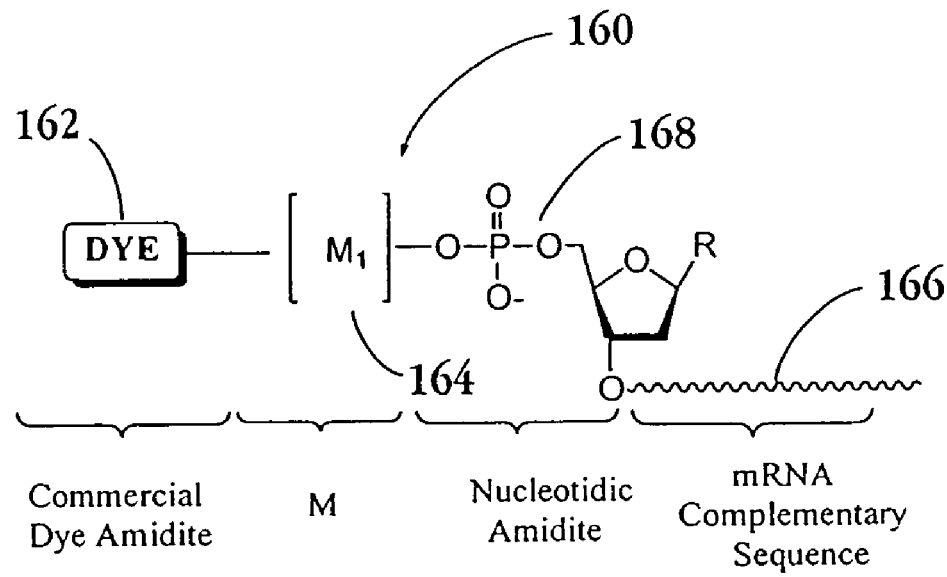
FIGS. 6 and 7 illustrate the basic structure of two embodiments of single-tag electrophoretic tag (e-tag) probes constructed in accordance with the invention.
Figure 7:
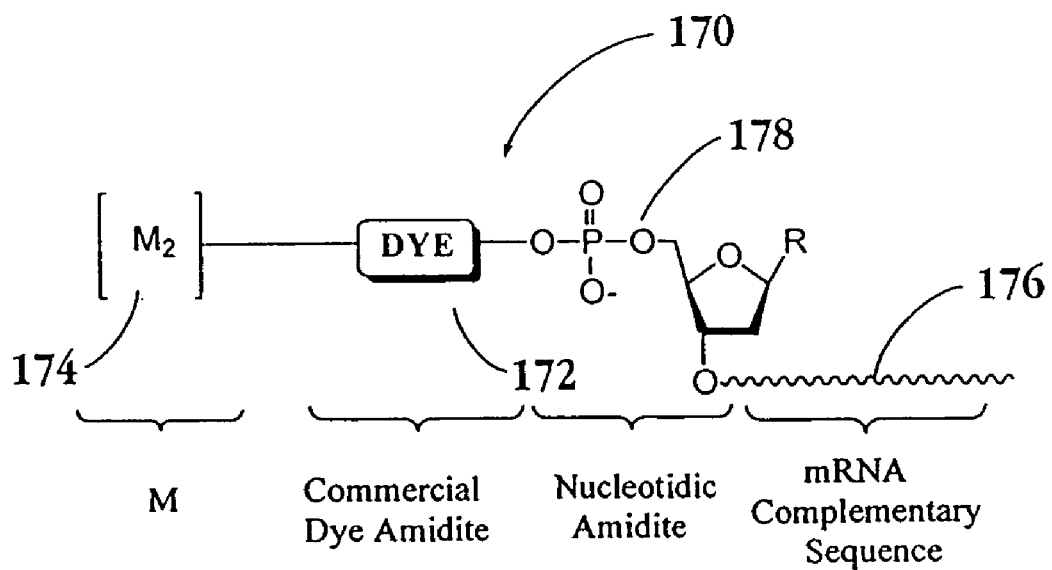

FIGS. 6-8 illustrate three general types of e-tag probes constructed in accordance with the invention. In the e-tag probes illustrated in FIGS. 6 and 7, each probe has a single releasable e-tag. In the e-tag probe illustrated in FIG. 8, each probe includes a plurality of releasable e-tags. A set of e-tag probes, in accordance with the invention, includes a plurality of probes with different target-binding agents or moieties, preferably one for each potential target to be assayed, and a different e-tag associated with each different binding agent. Each different e-tag, when released form a probe, has unique and identifiable separation characteristics, e.g., electrophoretic mobility, which allows that e-tag to be uniquely identified with a given probe target-binding moiety. Below are considered the general features of both a single-tag probe set and a multiple-tag probe set.

B1. Single-tag Probe Set

FIGS. 6 and 7 illustrate two different embodiments of probes in a single-tag probe set. In the probe shown in FIG. 6, and indicated at 160, a detection group 162 (dye) is attached to a mobility modifier 164 ($M_1$) which in turn is attached to the target binding moiety 166 through a linker 168. In the e-tag probe illustrated in FIG. 7, and indicated at 170, the releasable e-tag, which includes detection group 172 (dye) and mobility modifier 174 ($M_1$), is attached to the target binding moiety 176 through a linker 178 linking the detection group to the binding moiety. More generally, in representing the e-tag as (D, $M_j$)-, the structure may be either (D, $M_j$)- or ($M_j$,D)-.

More generally, the probes in a single-tag probe set will have the form: (D, $M_j$)-L-$T_j$, or (D, $M_j$)-N-$T_j$, where D is a detection moiety, $M_j$ is the jth mobility modifier, Tj is the jth target binding agent, and the linking group is represented by L (or by N when the linking group is the 5'-terminal nucleotide of an oligonucleotide target-binding moiety). In this and related structural designations, and as noted above, (D, $M_j$)- indicates that either the detection group or the mobility modifier is joined to the linking group, i.e., either (D, $M_j$) or ($M_j$,D)-.

An e-tag probe as defined herein has the form: (D, $M_j$)-N-$T_j$, or (D, $M_j$)-L-$T_j$, where (D, Mj)- includes both D-$M_j$- and $M_j$-D-.

As noted above, the "detection group" or "D" component of the e-tag probe is a chemical group or moiety that is capable of being detected by a suitable detection system, particular in the context of detecting molecules containing the detection group after or during electrophoretic separation. One preferred detection group is a fluorescent group that can be readily detected during or after electrophoretic separation of molecules by illuminating the molecules with a light source in the excitation wavelength and detecting fluorescence emission from the irraidated molecules. Exemplary fluorescent moieties are further described below. The detection group may contribute to the unique electrophoretic mobilities of a released e-tag reporter.

The "charged mobility group" or "mobility modifier" "M" component of the e-tag probe is a chemical group or moiety that is designed to have a particular charge to mass ratio, and thus a particular electrophoretic mobility in a defined electrophoretic system. Exemplary types of mobility modifiers are discussed below. In a set of n e-tag probes, each unique mobility modifier is designated $M_j$, where j=1 to n, as above. The mobility modifier may be considered to include a mass-modifying region and/or a charge-modifying region or a single region that acts as both a mass- and charge-modifying region. The "linking group" or "L" component of the e-tag probe is a sequence that is connected to $T_j$ by a bond that is cleavable by a selected cleaving agent when the probe is bound to, or interacting with, a target nucleic acid sequence.

The target-binding moiety "$T_j$" refers to the component of an e-tag probe that participates in recognition and specific binding to the e-tag probe recognition site generated by amplificatio of a target nucleic acid with a universal e-tag primer. Where the probe is designed to be cleaved by an exonuclease, as described above, the linker L (or N) is the 5' nucleotide of the oligonucleotide containing the target-binding moiety.

Further in this embodiment, and as detailed in the E-tag Patents, the probe binding moieties may each be modified either to prvent nuclease cleavage beyond the initial 5' nucleotide intersubunit linkage (linking the 5' nucleotide N to the target-binding oligonucleotide) or to allow capture of e-tags released by nuclease cleavage downstream of the 5' intersubunit linkage. In the former case, intersubunit linkages downstream of the 5' linkage may be nuclease resistant linkages, e.g., carbamate, phosphonate or phosphoramidate linkages. In the latter embodiment, the penultimate nucleotide (the nucleotide just downstream of N) may carry a caputure moirty, such as biotin, that allows released e-tags carrying this nucleotide to be captures.

FIGS. 9A-9J illustrate exemplary e-tags suitable for use in the invention. The syntheses of these and other e-tag and e-tags probes is described in the E-gat Patents. FIG. 10 provides information about charge and electrophoretic mobility, given in elution time, for several representative e-tags, illustrating how difference in charge and size in different e-tags contribute to different electrophoretic mobilities. It will be appreciated that different detection groups, e.g., dyes with different charges, may also be employed to vary the separation characteristics of released e-tags. Thus, for example, the e-tags in a probe set may have different subclasses of e-tags, each subclass having a given dye with the same charge and mass, and different mobility modifiers associated with the dye.

B2. Multiple-tag Probe Set

Figure 8A:
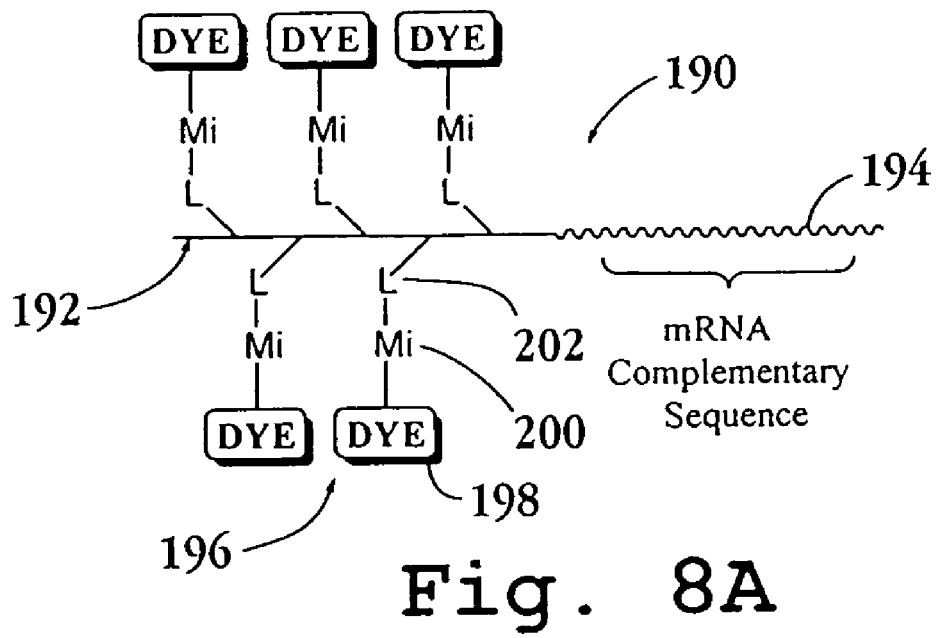
FIGS. 8A and 8B illustrate the basic structure of two embodiments of multiple-tag e-tag probes constructed in accordance with other embodiments of the invention.
Figure 8B:
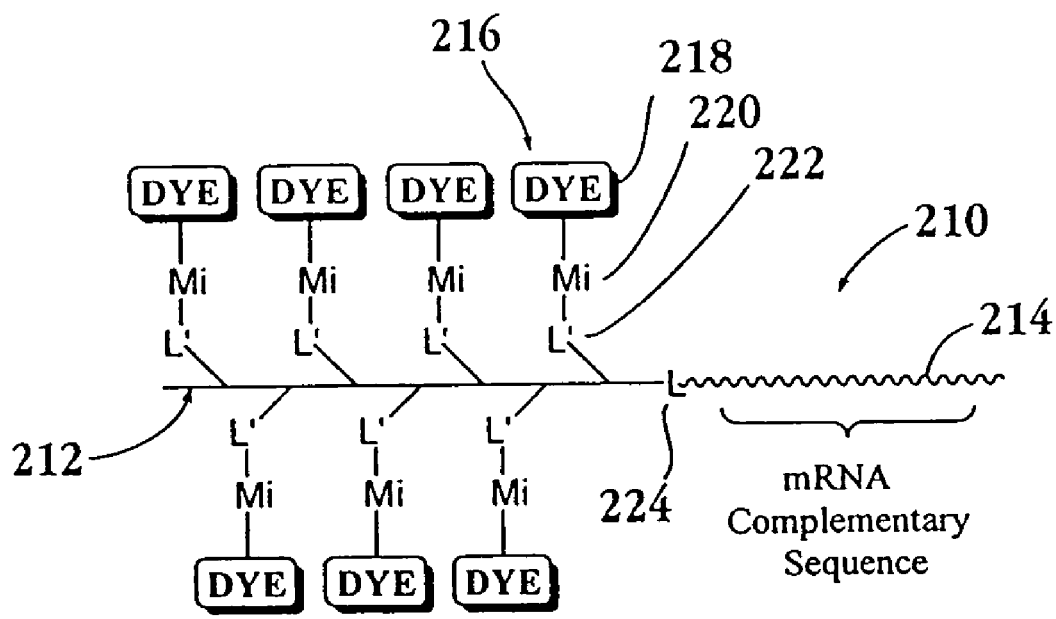
Figure 9A:
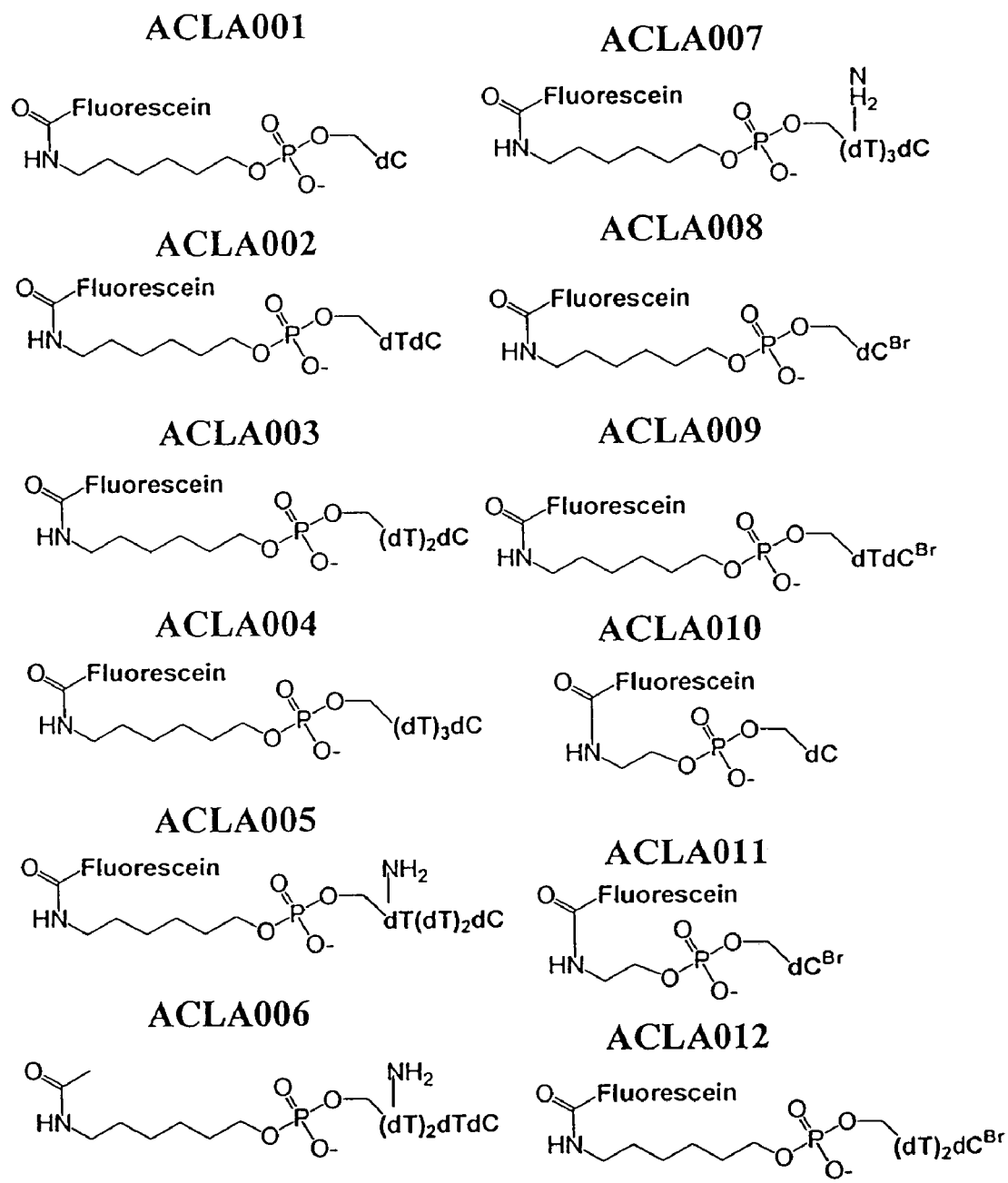
Figure 9B:
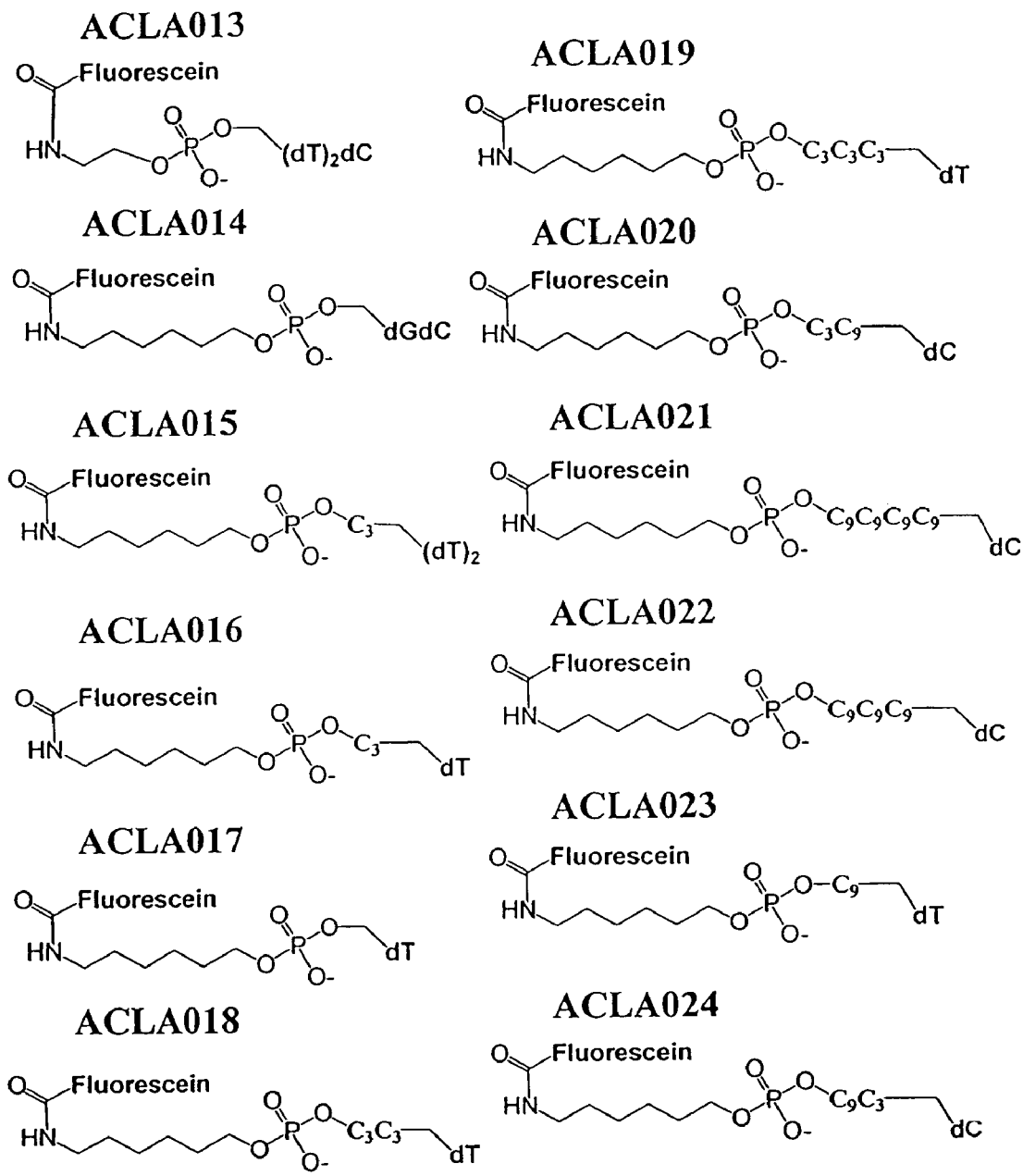
Figure 9C:
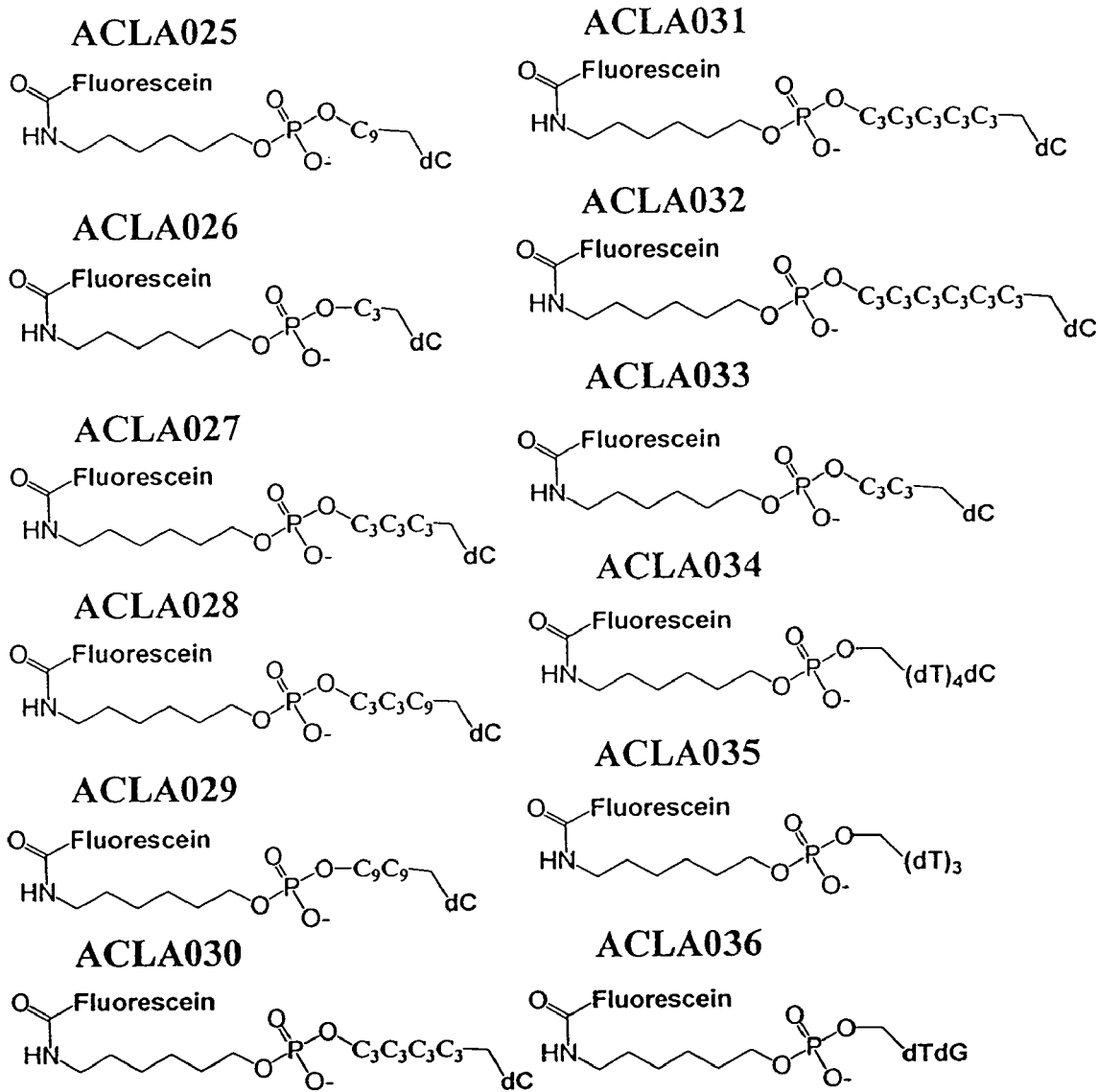
Figure 9E:
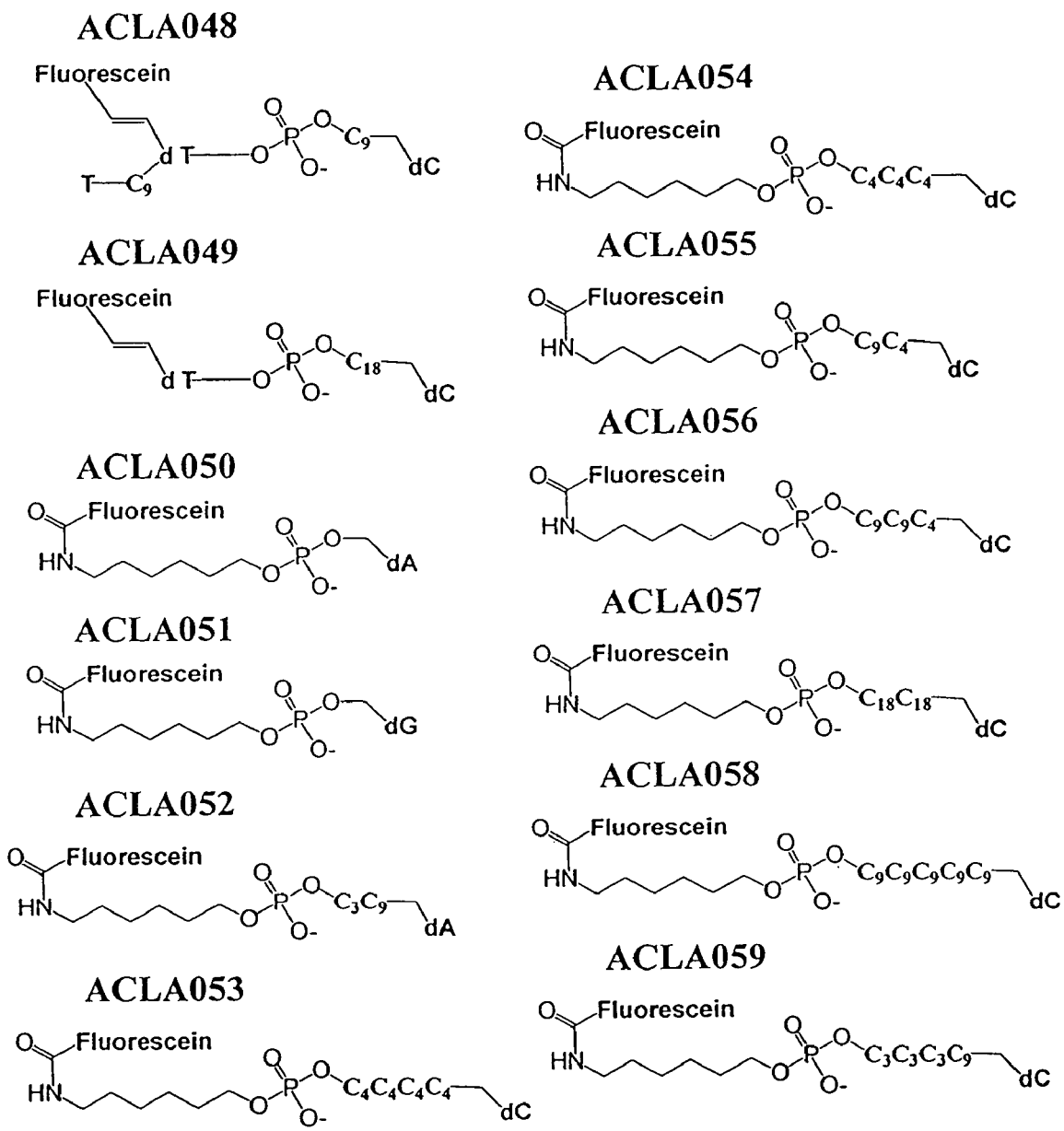
Figure 9F:
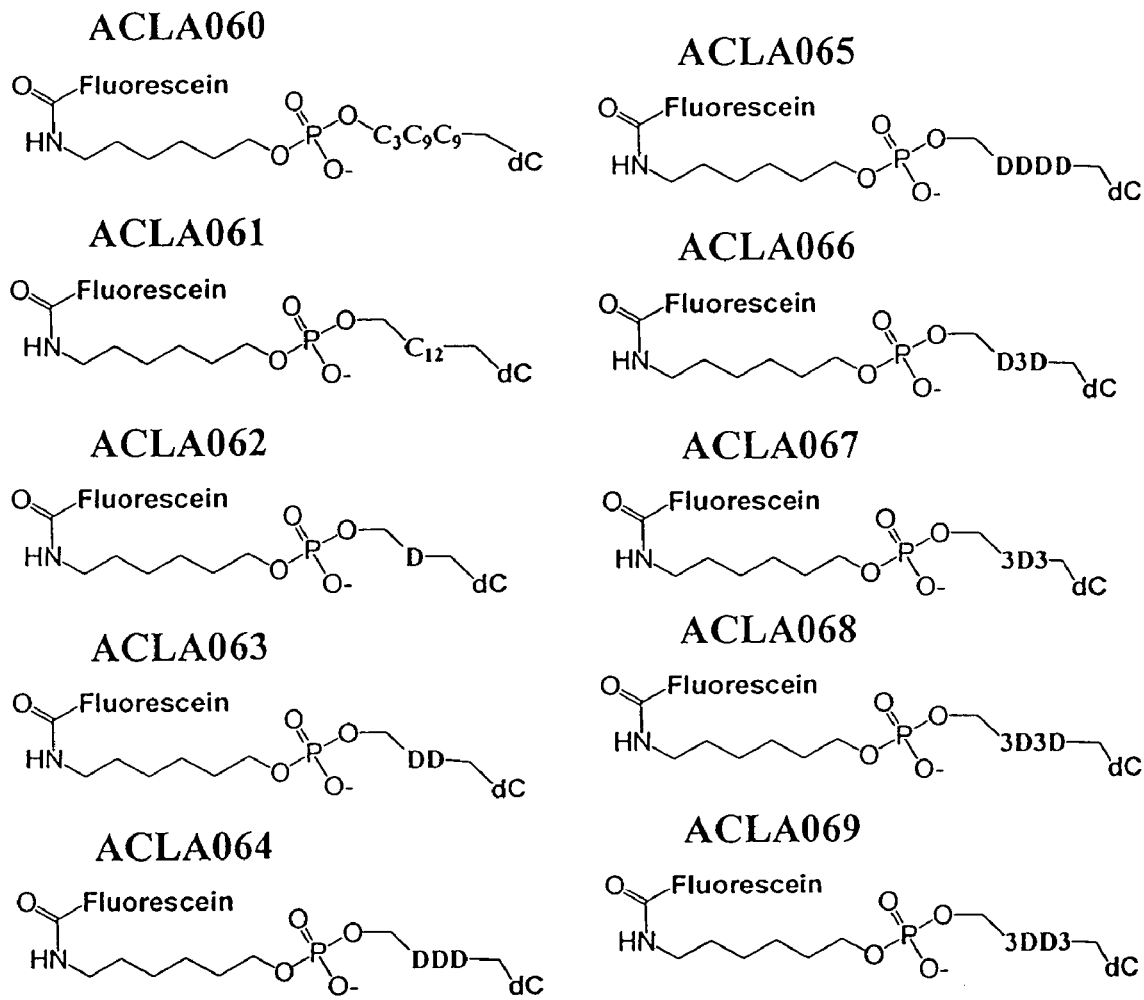
Figure 9G:
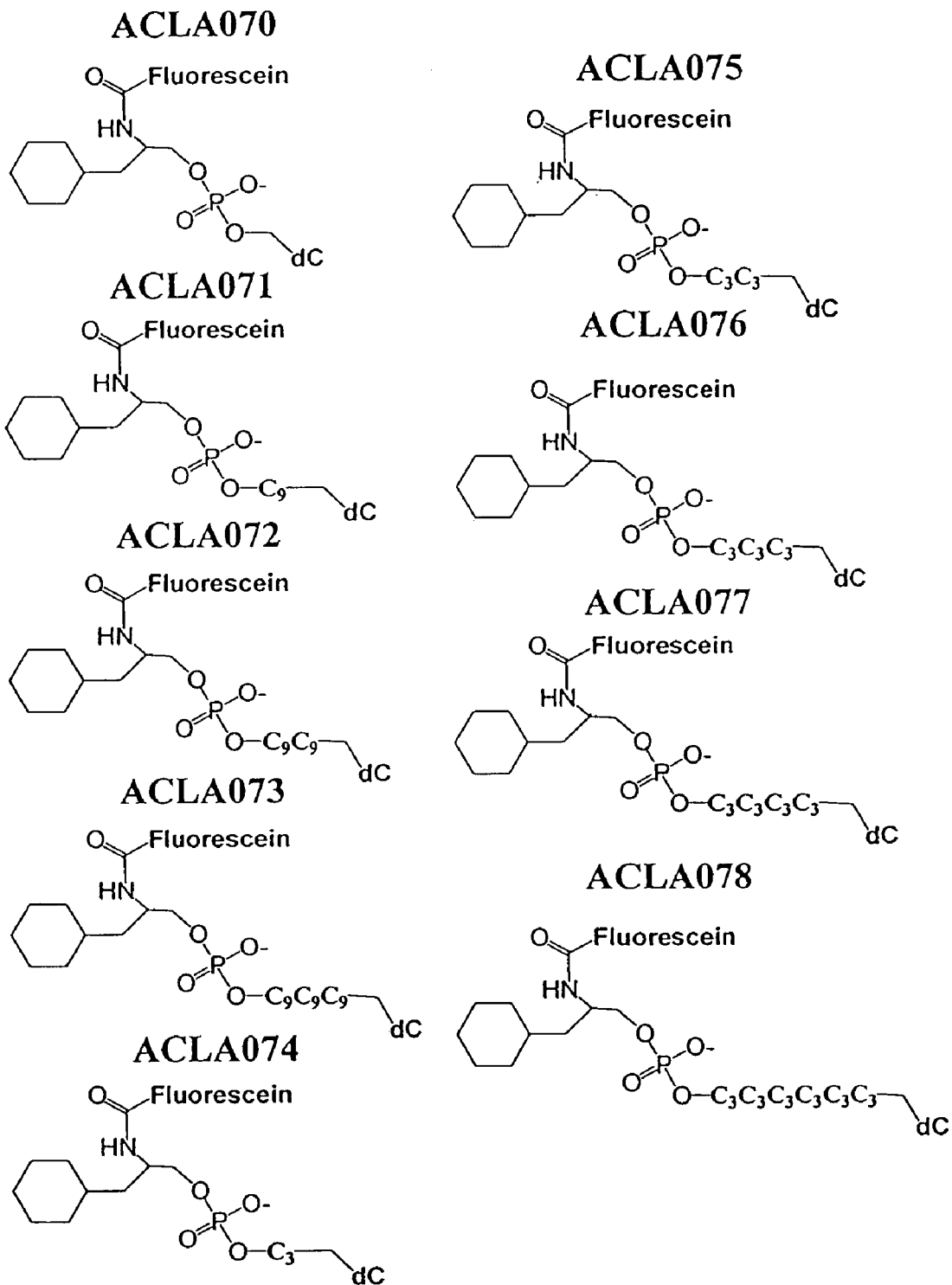
Figure 9H:
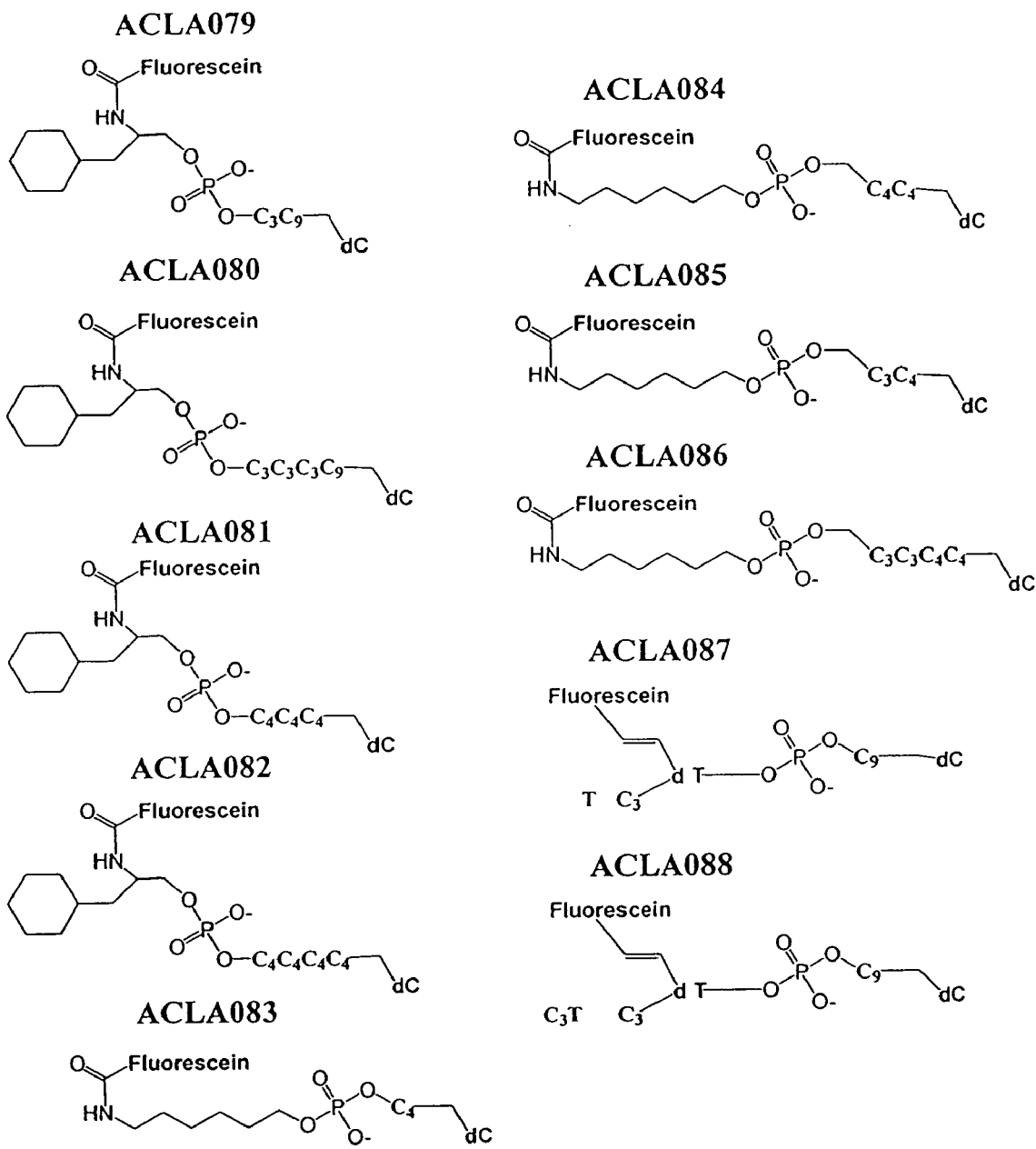
Figure 9I:
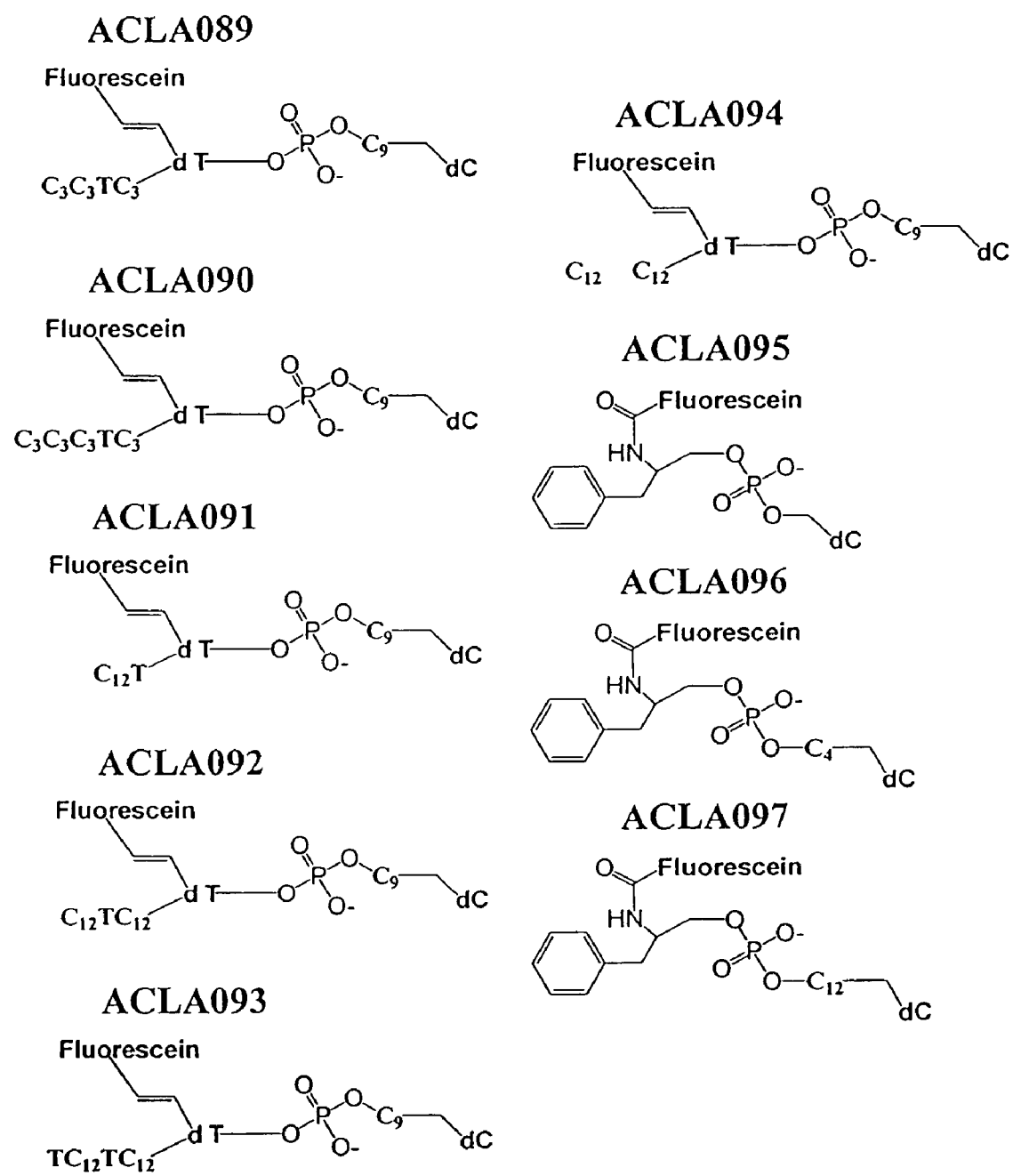
Figure 9J:
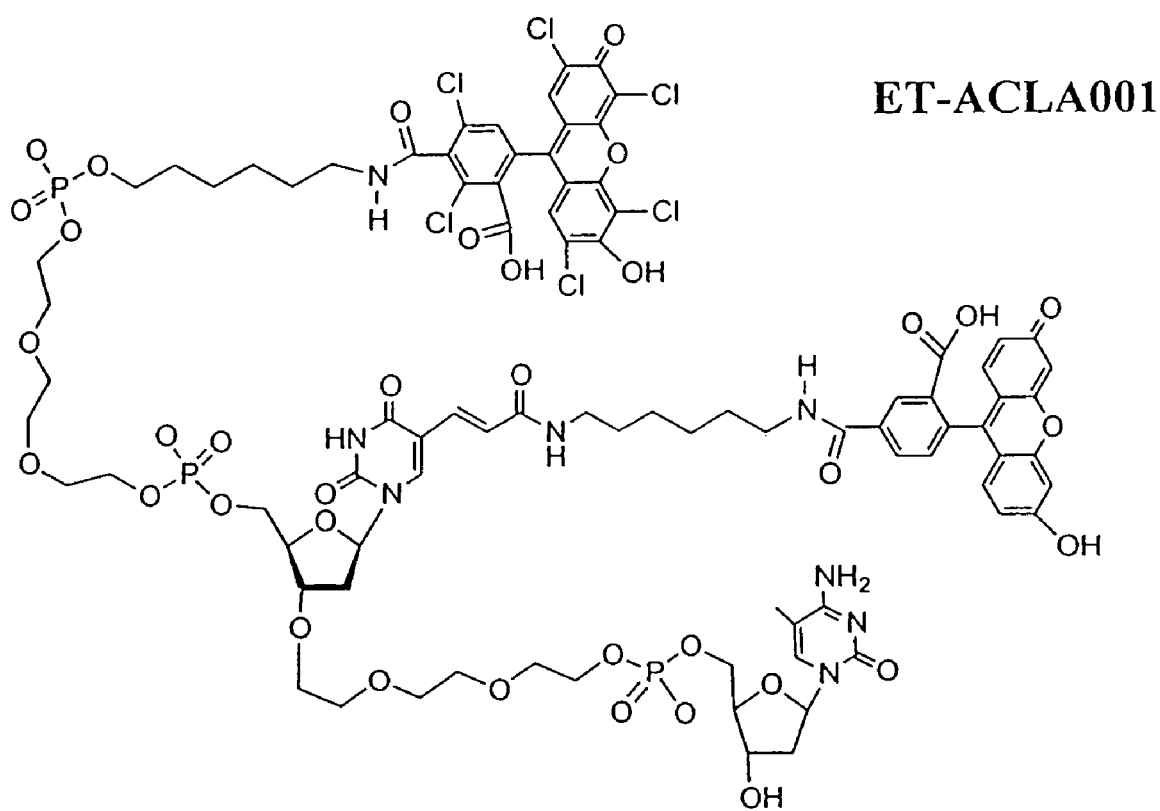

FIGS. 8A and 8B illustrate two different types of multi-tag probes in probe sets constructed according to a second general embodiment of the invention. The probe illustrated in FIG. 8A is illustrative of the multi-tag probes described with respect to FIGS. 3A and 3B, where probe cleavage and e-tag release occur at the target site, and require binding of a universal probe and an e-tag probe at proximate locations at the target region. The probe illustrated in FIG. 8B illustrates a second type of multi-tag probe in which initial cleavage, under one set of cleavage conditions, is effective to release a branched structure holding multiple tags, and subsequent target-independent cleavage, under different cleavage conditions, is effective to release individual e-tags from the released branch structure.

Considering first the embodiment illustrated in FIG. 8A, the probe, indicated at 190, includes a target-binding moiety 194, and a branched polymer 192 or other dendritic or multisite structure capable of supporting multiple releasable e-tags thereon. As shown here, each of several identical e-tags composed of a detection group, such as dye 98, and a mobility modifier $M_j$, such as indicated at 200, is linked to a branch in the structure through a cleavable linker L. As indicated above, the cleavable linker employed in this embodiment is typically one that is cleavable by an activated chemical species, such as single oxygen, allowing cleavage or most or all of the e-tags, when the probe is proximate a source of the activated species. Probes of this type are described, for example, in co-owned U.S. patent application of "Determination of Target Analytes Employing Cleavable, Electrophoretically Tagged Reagents, cited above.

More generally, the probes in the probe set in this embodiment have the general form $(D, M_j\text{-L})_j\text{-B-T}_j$, where (i) D is a detection group comprising a detectable label or a catlytic group capable of catalyzing a detectable reaction;

(ii) $T_j$ is an oligonucleotide target-binding moiety for binding an e-tag probe recognition sequence;

(iii) B is a branched polymer or other multisite structure having multiple electrophoretic tags probes attached thereto, each through a linkage L that is cleavage under target-dependent conditions;

(iv) L' is the residue of L remaining after cleavage of the electrophoretic probes from the branched structure;

(v) $M_j$ is a mobility modifier having a charge/mass ratio that imparts to the corresponding electrophoretic tag, an electrophoretic mobility that is unique to a given extension sequence; and (vi) $(D, M_j)$- includes both $D\text{-}M_j\text{-}$ and $M_j\text{-}D\text{-}$.

D, $M_j$, and are as discussed above, except that $T_j$ does not need to be modified to include nuclease-resistant linkages or ligands for affinity binding, since the e-tags are not released by exonuclease cutting.

Considering now the probe embodiment illustrated in FIG. 8B, representative probe 210 includes a target-binding moiety 214, and a branched polymer 212 or other dendritic or multisite structure capable of supporting multiple releasable e-tags thereon. Moiety 214 is linked to structure 212 through a linkage 224 that is cleavabale under target-dependent conditions, e.g., by a primer-dependent exonuclease reaction, a restrictio endonuclease, or cleavage involving an activated chemical cleaving agent.

Each of several identical e-tags composed of a detectio group, such as dye 218, and a mobility modifier $M_j$, such as indicated at 220, is linked to a branch in the structure through a cleavable linker L'. Liner L' is cleavable under target-independent conditions to release individual e-tags from the branched structure, after release of the branched structure from the probe. Thus, linker L' must be one that is not cleaved under the target-dependent conditions used in cleaving the branched structure from the probe, but can be cleaved under target-independent conditions, such as by photolysis. Probes of this type are described in co-owned U.S. patent application for "Determination of Target Analytes, Employing Cleavable, Electrophoretically Tagged Reagents, cited above.

More generally, the probes in the probe set in this embodiment have the general form:$(D, M_j\text{-L'})_j\text{-B-N-T}_j$, where (i) D is a detection group comprising a detectable label or a catalytic group capable of catalyzing a detectable reaction;

(ii) $T_j$ is a oligonucleotide target-binding moiety for binding an e-tag probe recognition sequence;

(iii) B is a branched polymer having multiple electrophoretic tags probes attached thereto, each through a linkage L' that is cleavage under cleavage conditions different from said selected conditions employed in step (d);

(iv) B' is the residue of B remaining after cleavage of the electrophoretic probes from the branched structure;

(vi) $M_j$ is a mobility modifier having a charge/mass ratio that imparts to the corresponding electrophoretic tag, an electrophoretic mobility that is unique to a given extension sequence, and (vii) $(D, M_j)$-includes both $D\text{-}M_j\text{-}$ and $M_j\text{-}D$.

As with the probes illustrated in FIGS. 6 and 7, Tj may be modified modified to include nuclease-resistant linkages or ligands for affinity binding, where the probes are cleaved initially, to release the branched structures, by a primer-dependent exonuclease.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

Example 1

Construction of Universal e-tag Primers

In order to design target specific universal e-tag primers, each variant sequence to be detected is selected and the variant position along with its sequence context is identified.

Following identification of candidate sequences, the sequences are characterized as to probe sequence lengths, GC content (% GC), probe base composition (for all 4 nucleotides) and Tm as provided below in Table 1.

A universal secondary amplification primer is designed or selected and its complementary sequence added to the universal e-tag primer design. Prior to use in an assay, the component sequences are checked by BLAST (Basic Local Alignment Search Tool) analysis, such that sequences with high similarity to human genomic sequences can be discarded. Tm of the similar sequences was checked using the nearest neighbor method. Examples of e-tag reporter sequences are provided in Tables 2 and 3.

TABLE 1

Characterization Of Universal e-tag Primer Target Specific Components

| SNP FactorV-leiden | Sequence | Length | % GC | Tm (° C.) |
|---|---|---|---|---|
| gs_primerFVwt | TACTTCAAGGACAAAATACCTGTATTCCGC (SEQ ID NO:4) | 30 | 40.0 | 75.4 |
| gs_primerFVmt | TACTTCAAGGACAAAATACCTGTATTCCAT (SEQ ID NO:5) | 30 | 33.3 | 72.7 |
| com_primerV | CAGGGGAAACCTATACTTATAAGTGGAACATC (SEQ ID NO:6) | 32 | 40.6 | 77.1 |
| ApoE112 | | | | |
| gs_primer112_T | CGCGGACATGGAGGACGTTT (SEQ ID NO:7) | 20 | 60.0 | 72.4 |
| gs_primer112_C | CGCGGACATGGAGGACGTTC (SEQ ID NO:8) | 20 | 65.0 | 74.4 |
| com_p112 (cv) | GAGCATGGCCTGCACCTC (SEQ ID NO:9) | 18 | 66.7 | 71.3 |
| MTHFR | | | | |
| gs_pMTHFRwt | GAAGGAGAAGGTGTCTGCGGTAGC | 24 | 58.3 | 77.3 |
| gs_pMTHFRmt | GAAGGAGAAGGTGTCTGCGGAAGT | 24 | 54.2 | 75.6 |
| com_pMTHFR | AGGACGGTGCGGTGAGAGTG (SEQ ID NO:10) | 22 | 65.0 | 74.4 |

Typically, in designing a universal e-tag primer, 20 random sequences are generated which have a length of 30 nucleotides, a 5' bases that is C, and a Tm of from 65-70° C. and which serve as e-tag probe extension sequences. Each pair of e-tag probe extension sequences in a selected set are filtered through a selection algorithm (developed at ACLARA BioSciences Inc.) to verify dissimilarity and to avoid non-specific cross-hybridization.

In general, each sequence in the selected set will has more than three consecutive C, G, A, T or consecutive (CA) repeats and 2-4 positions 3' to the 5' terminal C base are alternative linkages such as chimeric phosphorothioate linkages rather than standard phosphoramidite with biotin added to the 3' end of the e-tag probe to provide a "handle" to remove uncleaved probe prior to electrophoretic analysis.

A second set of sequences may also be designed using the criteria that the 5' base is C and the next base is biotin-T to provide a "handle" to remove uncleaved probe and alternatively cleaved probe prior to CE or microfluidic analysis.

TABLE 2

Exemplary e-tag Reporter Sequences (5' base is C)

| e-tag reporter | Sequence | Tm | % GC | Tm2 |
|---|---|---|---|---|
| eR1 | CGCGATTGGCGTCGTCTGAGCGCCTTT AAA (SEQ ID NO:11) | 68.8 | 56.7 | 82.2 |
| eR2 | CCATGCCAACTACE-TAGCTGCCGTGA ACAA (SEQ ID NO:12) | 65.1 | 53.3 | 80.9 |
| eR3 | CAGCCACACAGAGCGCE-TAGTTCCAA TGAC (SEQ ID NO:13) | 66.0 | 56.7 | 82.2 |
| eR4 | CGGCGTAGCCCTCTCCGTCGTCCTGTG TCC (SEQ ID NO:14) | 69.2 | 70.0 | 87.7 |
| eR5 | CGACGCTTTGCAGATGATATACTTGCG CGG (SEQ ID NO:15) | 67.4 | 53.3 | 80.9 |
| eR6 | CCGTGGATCAGCCTGCCCGATTCCGTC ACA (SEQ ID NO:16) | 68.0 | 63.3 | 85.0 |

TABLE 2-continued

Exemplary e-tag Reporter Sequences (5' base is C)

| e-tag reporter | Sequence | Tm | % GC | Tm2 |
|---|---|---|---|---|
| eR7 | CGGCCTTCATAGCGAAGTTACCCGGCT TTA (SEQ ID NO:17) | 65.5 | 53.3 | 80.9 |
| eR8 | CATCCGCAGGTAGAATGACGGGAAGCC GAT (SEQ ID NO:18) | 66.3 | 56.7 | 82.2 |
| eR9 | CCTGTTGCGCCCTGAAGACAAGAGATT TCG (SEQ ID NO:19) | 65.6 | 53.3 | 80.9 |
| eR10 | CGAGCAACCGGTCCGTCTCTACCCTAA ACG (SEQ ID NO:20) | 66.0 | 60.0 | 83.6 |
| eR11 | CGAAGCGTAGGTCAACCCTGAGCGTGC GAT (SEQ ID NO:21) | 68.5 | 60.0 | 83.6 |
| eR12 | CGCGAGCGE-TAGTGAACGTACE-TAG ATTTC (SEQ ID NO:22) | 65.9 | 53.3 | 80.8 |
| eR13 | CTGAGATGTGTGGTE-TAGGCGGCAGG CGAA (SEQ ID NO:23) | 68.0 | 60.0 | 83.6 |
| eR14 | CAACTGTCGGGACATTAACGGTGGGCA GCA (SEQ ID NO:24) | 65.4 | 56.7 | 82.2 |
| eR15 | E-TAGTCGAACAAGGCGGTAAACGCCA AGC (SEQ ID NO:25) | 65.2 | 53.3 | 80.9 |
| eR16 | CCCAGTGCTATAGCACCGGCTCGCATG GAT (SEQ ID NO:26) | 68.3 | 60.0 | 83.6 |
| eR17 | CCCACCCGTTGTTGTTTCGAGACTCGC ACA (SEQ ID NO:27) | 65.4 | 56.7 | 82.2 |
| eR18 | CATCATTCTATCGCGACAACGCGGGCC GAA (SEQ ID NO:28) | 67.8 | 56.7 | 82.2 |
| eR19 | CCTCGAGTACCTTTGCACGAACCTCCT ACG (SEQ ID NO:29) | 65.1 | 56.7 | 82.2 |
| eR20 | CCGTTCGCGTAGTGCCGAGGGCATCAA TTA (SEQ ID NO:30) | 67.0 | 56.7 | 82.2 |
| eR21 | CCACGCCTCCTATTTGTCTTCAGCCGC GTC (SEQ ID NO:31) | 67.4 | 60.0 | 83.6 |
| eR22 | CAGGTTCGCACTCAGTCTTTCCAAGGC GCG (SEQ ID NO:32) | 68.4 | 60.0 | 83.6 |

TABLE 3

Exemplary e-tag Reporter Sequences (5' base is C and 2nd 5' base is T)

| e-tag reporter | Sequence | L | Tm | % GC | Tm2 |
|---|---|---|---|---|---|
| eR31 | E-TAGTACCAAGGTGGCGAACGAG ACCAGGC (SEQ ID NO:33) | 30 | 65.8 | 60.0 | 83.6 |
| eR32 | CTTTGGCCTTGAGAATGAGCAGAT GACGGG (SEQ ID NO:34) | 30 | 65.2 | 53.3 | 80.9 |
| eR33 | CTCAGGCTCAGCCAATGGTAAGAC TGCGGG (SEQ ID NO:35) | 30 | 67.4 | 60.0 | 83.6 |
| eR34 | CTCGGCACGGTTCTACGGAGTGCA TAGCGA (SEQ ID NO:36) | 30 | 68.3 | 60.0 | 83.6 |
| eR35 | CTGTATCATCATTCACGGCTGCAG GGCCCT (SEQ ID NO:37) | 30 | 66.5 | 56.7 | 82.2 |
| eR36 | CTACTTGCCTTCGCGTAGTGGAGG AGAGTT (SEQ ID NO:38) | 30 | 65.3 | 53.3 | 80.9 |
| eR37 | CTCGGTCGGGCTACACTTCCTGTT AAGGCA (SEQ ID NO:39) | 30 | 65.6 | 56.7 | 82.2 |
| eR38 | CTCGACCGCCAATCCGCAATATGA GCCATG (SEQ ID NO:40) | 30 | 67.0 | 56.7 | 82.2 |
| eR39 | CTCCCGGAGCGTGCAGACTATCCA GGTGTA (SEQ ID NO:41) | 30 | 66.7 | 60.0 | 83.6 |
| eR40 | CTGCATTGTGGCAGCTTACCATGC AGGTTG (SEQ ID NO:42) | 30 | 65.8 | 53.3 | 80.9 |
| eR41 | CTCGCTGGAGTCTGAAAGGCCAGA GATACA (SEQ ID NO:43) | 30 | 65.6 | 53.3 | 80.9 |
| eR42 | CTGAACAATGCCGCGACAATGGAG CTGAAG (SEQ ID NO:44) | 30 | 66.4 | 53.3 | 80.9 |
| eR43 | CTCAGATCCACGTAAATGGGCAGC TTGCGT (SEQ ID NO:45) | 30 | 66.1 | 53.3 | 80.9 |
| eR44 | CTACCAGATAGGCTTCCTGCGTCA ATCCGG (SEQ ID NO:46) | 30 | 65.7 | 56.7 | 82.2 |
| eR45 | CTGAGACGATAGGGCCGCTTATTG CACCCT (SEQ ID NO:47) | 30 | 66.6 | 56.7 | 82.2 |
| eR46 | CTTTGGGTGAGAGCCAACAGTGGA CTGGCA (SEQ ID NO:48) | 30 | 65.5 | 56.7 | 82.2 |
| eR47 | CTACGCACCTATGACGCGCCTAAC CTTTGG (SEQ ID NO:49) | 30 | 66.2 | 56.7 | 82.2 |
| eR48 | CTGAGCTGGCTACAGCCACCGGGT TAGAGT (SEQ ID NO:50) | 30 | 67.2 | 60.0 | 83.6 |
| eR49 | E-TAGATCTTACAGAATCCGCCGC GCAATTG (SEQ ID NO:51) | 30 | 65.4 | 50.0 | 79.5 |
| eR50 | CTCAGGAAGGGCGAAGCGTTCCCT GCCAAT (SEQ ID NO:52) | 30 | 68.0 | 60.0 | 83.6 |

Exemplary Universal Primer sequences for use in universal e-tag primers of the invention are provided in Table 4.

TABLE 4

Universal Primer (Up) and Spacer (S) Sequences For Use In Primer Design

| Name | Uprimer/UprimerSpacer | L | Tm | % GC | Tm2 |
|---|---|---|---|---|---|
| Up_M1 | AGGTCCACTGCGTCCGATGT (SEQ ID NO:53) | 20 | | 60.0 | 72.4 |
| Up_M1+S | AGGTCCACTGCGTCCGATGTTCGACT (SEQ ID NO:54) | 26 | | 57.7 | 79.2 |
| Up_M2 | TTGGCAGCTCTCGGCATCAG (SEQ ID NO:55) | 20 | | 60.0 | 72.4 |

TABLE 4-continued

Universal Primer (Up) and Spacer (S) Sequences For Use In Primer Design

| Name | Uprimer/UprimerSpacer | L | Tm | % GC | Tm2 |
|---|---|---|---|---|---|
| Up_M2+S | TTGGCAGCTCTCGGCATCAGTCGACT (SEQ ID NO:56) | 26 | 57.7 | | 79.2 |
| Up_M3 | TGAAGACCGTCGTCGCGTAC (SEQ ID NO:57) | 20 | 60.0 | | 72.4 |
| Up_M3+S | TGAAGACCGTCGTCGCGTACTCGACT (SEQ ID NO:58) | 26 | 57.7 | | 79.2 |

Following primer design, the primer components are combined (5' universal primer sequence+spacer+e-tag probe binding site+allele specific primer into a final sequence (designated a universal e-tag primer) which is further screened to avoid self-annealing and hairpin structures.

Standard PCR primers and protocols for the MTHFR C677T and ApoE genotypes were obtained as described elsewhere in order to genotype human genomic DNA by PCR-RFLP (Hixson JE, Vernier DT, J Lipid Res 1990. 31:545*548; Frosst P, et al. Nat Genet 1995. 10:111-113). New primers were designed for Factor V Leiden PCR. The PCR products were cleaved with Mnl 1, separated by electrophoresis in 10% polyacrylamide gels and developed by silver staining.

Allele PCR primers for the MTHFR C677T, Factor V Leiden and ApoE were obtained as described elsewhere (Clin Chem, 1998, 44:264-269; Clin Chem, 1998, 44:918-923; Clin Chem, 1999, 45:143-146).

Exemplary universal e-tag primers for use in practicing the invention are presented in Table 5.

TABLE 5

Allele specific forward and reverse primers

| Name | Universal e-tag Primer |
|---|---|
| 4FVw (forward) | AGGTCCACTGCGTCCGATGTTCGACTCGGCGTAGCCCTCTC CGTCGTCCTGTGTCCTACTTCAAGGACAAAATACCTGTATTCCGC (SEQ ID NO:59) |
| 18FVm (forward) | AGGTCCACTGCGTCCGATGTTCGACTCATCATTCTATCGCGACA ACGCGGGCCGAATACTTCAAGGACAAAATACCTGTATTCCAT (SEQ ID NO:60) |
| CFVr (reverse) | AGGTCCACTGCGTCCGATGTCAGGGGAAACCTATACTTATAAGTGGAACATC (SEQ ID NO:61) |
| 10MTHFRw (forward) | AGGTCCACTGCGTCCGATGTTCGACTCGAGCAACCGGTCCGT CTCTACCCTAAACGGAAGGAGAAGGTGTCTGCGGTAGC (SEQ ID NO:62) |
| 20MTHFRm (forward) | AGGTCCACTGCGTCCGATGTTCGACTCCGTTCGCGTAGTGCCG AGGGCATCAATTAGAAGGAGAAGGTGTCTGCGGAAGT (SEQ ID NO:63) |
| CMTHFRr (reverse) | AGGTCCACTGCGTCCGATGTAGGACGGTGCGGTGAGAGTG (SEQ ID NO:64) |
| 50E112T (forward) | AGGTCCACTGCGTCCGATGTTCGACTCTCAGGAAGGGCGAAGC GTTCCCTGCCAATCGCGGACATGGAGGACGTTT (SEQ ID NO:65) |
| 47E112C (forward) | AGGTCCACTGCGTCCGATGTTCGACTCTACGCACCTATGACG CGCCTAACCTTTGGCGCGGACATGGAGGACGTTC (SEQ ID NO:66) |
| cE112r (reverse) | AGGTCCACTGCGTCCGATGTGAGCATGGCCTGCACCTC (SEQ ID NO:67) |

In Table 5, with regard the forward primers, from the 5' to 3' direction the first 20 nucleotides are the Up_M1 common universal primer sequence, the next 6 nucleotides are the spacer sequence; the next 30 nucleotides are the e-tag probe binding or recognition sequence; and the last 30 nucleotides are the forward allele specific primers.

The length of the amplicons for the exemplary MTHFR C677T, FV-Leiden and APOE T112C SNPs are approximately 270 bp, 277 bp and 139 bp, respectively.

Exemplary e-tag probes for binding to the e-tag recognition sequences generated by the specific amplification of a target nucleic acid with a universal e-tag primer of the inventions are provided in Table 6 (ACLARA BioSciences).

In Tables 6 and 7, "*" refers to a chimeric phosphorothioate and biotin refers to 3' biotin-TEG. Biotin-TEG contains a 15-carbon mixed polarity spacer arm based on a TriEthylene Glycol.

TABLE 6

Exemplary e-tag Probe Oligos (ACLARA BioSciences)

| e-tag Reporter | Sequence and Modifications |
|---|---|
| a126CT-eR4 | TET-CG*G*C*GTAGCCCTCTCCGTCGTCCTGTGTCC-biotin^ (SEQ ID NO:68) |
| a126CF-eR18 | 6-FAM-CA*T*C*ATTCTATCGCGACAACGCGGGCCGAA-biotin^ (SEQ ID NO:69) |
| a156CT-eR10 | TET-CG*A*G*CAACCGGTCCGTCTCTACCCTAAACG-biotin^ (SEQ ID NO:70) |
| a156CF-eR20 | 6-FAM-CC*G*T*TCGCGTAGTGCCGAGGGCATCAATTA-biotin^ (SEQ ID NO:71) |
| a125CT-eR36 | TET-CT*A*C*TTGCCTTCGCGTAGTGGAGGAGAGTT-biotin^ (SEQ ID NO:72) |
| a125CF-eR34 | 6-FAM-CT*C*G*GCACGGTTCTACGGAGTGCATAGCGA-biotin^ (SEQ ID NO:73) |
| a1CT-eR50 | TET-CT*C*A*GGAAGGGCGAAGCGTTCCCTGCCAAT-biotin^ (SEQ ID NO:74) |
| a1CF-eR47 | 6-FAM-CT*A*C*GCACCTATGACGCGCCTAACCTTTGG-biotin^ (SEQ ID NO:75) |

Example 2

Detection Of Single Base Differences In A Single Reaction Mixture

The universal e-tag primer methodology of the invention was used to determine single base differences, exemplified by an analysis of the mutant and wild type MTHFR C677T SNP in a single reaction.

TABLE 7

Exemplary e-tag Probe Oligos (Integrated DNA Technologies)

| e-tag Reporter | Sequence and Modifications |
|---|---|
| a126CT-eR4 | TET-(M5)2-CG*G*C*GTAGCCCTCTCCGTCGTCCTGTGTCC-biotin^ (SEQ ID NO:76) |
| a126CF-eR18 | 6-FAM-(M5)2-CA*T*C*ATTCTATCGCGACAACGCGGGCCGAA-biotin^ (SEQ ID NO:77) |

TABLE 7-continued

Exemplary e-tag Probe Oligos (Integrated DNA Technologies)

| e-tag Reporter | Sequence and Modifications |
|---|---|
| a156CT-eR10 | TET-(M2)2-CG*A*G*CAACCGGTCCGTCTCTACCCTAAACG-biotin^<br>(SEQ ID NO:78) |
| a156CF-eR20 | 6-FAM-(M2)2-CC*G*T*TCGCGTAGTGCCGAGGGCATCAATTA-biotin^<br>(SEQ ID NO:79) |
| a125CT-eR36 | TET-(M5)-CT*A*C*TTGCCTTCGCGTAGTGGAGGAGAGTT-biotin^<br>(SEQ ID NO:80) |
| a125CF-eR34 | 6-FAM-(M5)-CT*C*G*GCACGGTTCTACGGAGTGCATAGCGA-biotin^ |
| a1CT-eR50 | TET-CT*C*A*GGAAGGGCGAAGCGTTCCCTGCCAAT-biotin^ |
| a1CF-eR47 | 6-FAM-CT*A*C*GCACCTATGACGCGCCTAACCTTTGG-biotin^ |

The primers and e-tag probes (ACLARA BioSciences) used in carrying out the reaction included the 10MTHRFw specific primer; 20MTHFRm specific primer; cMTHFRr Common reverse primer; the Universal Primer component Up_M1; the A156CT-eR10 e-tag probe for C677 wild type allele; and the A156CF-eR20 e-tag probe for T677 mutant allele.

The following reagents were combined and amplification carried out using the ARMS11 cycling conditions set forth below.

3.5 mM Cl$_2$Mg, 0.05 µM 10MTHFRw primer, 0.05 µM 20MTHFRm primer, 0.4 µM a156CT-eR10, 0.4 µM a156CF-eR20, 0.5 µM Universal Primer Up_M1, 0.5 U TaqGold DNA polymerase, 1× TaqGold Buffer, 100 µM dNTPs, 20 ng DNA in a final volume of 12.5 µL.

The cycling conditions used in the amplification were from the ARMS11 programs, as follows:

12 min at 95° C., 40 seconds, at 94° C., 80 seconds at 60° C. for 3 cycles; 40 seconds at 72° C., 40 seconds at 94° C., 80 seconds at 66° C. for 40 cycles, then 20 min at 4° C. and held at 15° C.

The samples were diluted 1/10 in 50% HiDi Formamide—0-0.8 ng/µL avidin -~500 pM Fluorescein Na$^+$ and loaded into a 3100 Genetic Analyzer (Applied Biosystems). Fluorescein was added as an internal reference peak.

The reactions were run and analyzed in the ABI Prism® 3100 Genetic Analyzer using the polymer POP4 and Genetic Analyzer 1× Buffer (following the manufacturer's instructions). The run module was GS_36_POP4e-tag_v02_30C_1400s (Pre-Run: 15 KV, 180 s; Injection: 3 KV, 10 s; Run: 15 KV, 1400 s; T=30 C).

The results presented in FIGS. 12A-12G are electropherograms illustrating e-tag-reporter detection by CE using an ABI Prism® 3100 Genetic Analyzer for the MTHFR C677T snp.

B. Specificity of Single Base Detection in Separate Reaction Mixtures

In order to evaluate the specificity of the assay, the universal e-tag primer methodology of the invention was used to determine single base differences, for the mutant and wild type MTHFR C677T SNP, in independent reactions.

Reagents were combined in two reaction mixtures and amplification was carried out using the ARMS11 cycling conditions set forth below.

Reaction Mix A: 3.5 mM Cl$_2$Mg, 0.05 µM 10MTHFRw primer, 0.4 µM a156CT-eR10, 0.5 µM Universal Primer Up_M1, 0.5 U TaqGold DNA polymerase, 1× TaqGold Buffer, 100 µM dNTPs, 20 ng DNA in a final volume of 12.5 µL.

Reaction Mix B: 3.5 mM Cl$_2$Mg, 0.05 µM 20MTHFRw primer, 0.4 µM a156CF-eR20, 0.5 µM Universal Primer Up_M1, 0.5 U TaqGold DNA polymerase, 1× TaqGold Buffer, 100 µM dNTPs, 20 ng DNA in a final volume of 12.5 µL.

The cycling conditions used in the amplification were from the ARMS11 programs, as follows:

12 min at 95° C., 40 seconds at 94° C., 80 seconds at 60° C. for 3 cycles; 40 seconds at 72° C., 40 seconds at 94° C., 80 seconds at 66° C. for 40 cycles, then 20 min at 4° C. and held at 15° C.

The samples were diluted 1/10 in 50% HiDi Formamide-0-0.8 ng/µL avidin -~500 pM Fluorescein Na$^+$ and then loaded in the 3100 Genetic Analyzer. Fluorescein was added as an internal reference peak.

The reactions were run and analyzed in the ABI Primer® 3100 Genetic Analyzer using the polymer POP4 and Genetic Analyzer 1× Buffer (following the manufacturer's instructions). The run module was GS_36_POP4e-tag_v02_30C_1400s (Pre-Run: 15 KV, 180 s; Injection: 3 KV, 10 s; Run: 15 KV, 1400 s; T=30 C).

The results presented in FIGS. 13A-13G. The results show that the universal e-tag primer methodology of the invention is specific, can be used to specifically discriminate between two sequences that differ by a single nucleotide, e.g., alleles for a single gene locus, when either of the sequences is independently analyzed or in the same reaction mixture.

C. Cross-Talk Between Allele Specific E-Tag Primers Under Non-Competitive and Competitive Conditions The MTHFR SNP was used in a quantiative assay to evaluate the yield of various amplification products produced by PCR with the 10MTHFRw wild type allele specific primer, the 20MTHFRm mutant allele specific primer and the cMTHFRr common reverse primer. The assay was carried out in a competitive assay format using the a156CT-eR10 and a156CF-eR20 e-tag probes (as in FIGS. 12A-12G), (A); a non-competitive assay format including only the a156CT-eR10 TET labeled e-tag probe specific for the wild type amplification product (as in FIGS. 3A and B); or a non-competitive assay format including only the a156CT-eR20 TET labeled e-tag probe specific for the mutant amplification product (as in FIGS. 13B, 13C).

Template DNA previously characterized for the MTHFR C677 SNP mutant/mutant (NA17001 DNA); wild type/wild type (NA17002 DNA); wild type/mutant (NA17003 DNA) using water as a negative control was used as the target in a universal e-tag primer amplification assay under competitive and non-competitive conditions, as set forth above. The MTHFR PCR amplication product is approximately 270 bp as indicated by an arrow the figure. The concentration of the MTHFR PCR bands (ng/μL) presented in Table 8, illustrate that PCR yields following universal e-tag primer amplification are similar for each specific PCR product in the case of a non-competitive assay format.

TABLE 8

Yields of MTHFR PCR Products (ng/μL):

| Genomic DNA Sample | Concentration of PCR Product (ng/μL) |
|---|---|
| 1 NA17001 | 13.7 |
| 2 NA17002 | 9.7 |
| 3 NA17003 | 9.2 |
| 4 Negative Control (NC) water | 0 |
| 5 NA17001 | 4.1 |
| 6 NA17002 | 13.7 |
| 7 NA17003 | 12.4 |
| 8 Negative Control (NC) water | 0 |
| 9 NA17001 | 12.4 |
| 10 NA17002 | 3.9 |
| 11 NA17003 | 15.4 |
| 12 Negative Control (NC) water | 0 |

These results indicate that: (1) under non-competitive reaction conditions, a negligible amount of cross-talk is detected; and that (2) under competitive reactions, genotype results are accurate and correspond to the expected results. FIG. 11 shows the results of (a) reactons under competitive conditions (1-4); (b) reactions done under non-competitive conditions (mutant allele primer; 6-8); and reactions done under non-competitive conditions (wild type allele primer; 9-11).

Example 3

Multiplexed Analysis Using Universal e-Tag Technology

Further analysis was carried out using a number of different e-tag probes for the detection of the MTHRF C677T SNP. In conducting this analysis, the following reagents were combined and amplification carried out using the ARMS11 cycling conditions set forth below: 3.5 mM $Cl_2Mg$, 0.05 μM MTHFR wild type and mutant specific primers, 0.2 μM e-tag probes (as described above), 0.5 μM Universal Primer, 1 U TaqGold, 1× TaqGold Buffer, 100 μM dNTPs, 20 ng DNA in a final volume of 10 μL.

The cycling conditions used in the amplification were from the ARMS11 programs, as follows: 12 min at 95° C., 40 seconds at 94° C., 80 seconds at 60° C. for 3 cycles; 40 seconds at 72° C., 40 seconds at 94° C., 80 seconds at 66° C. for 40 cycles, then 20 min at 4° C. and held at 15° C.

The samples were diluted 1/10 in 50% HiDi Formamide-0-0.8 ng/μL avidin -~1/100 RoxT8 and then loaded in the 3100 Genetic Analyzer. RoxT8 was added as an internal reference peak.

The reactions were runa nd analyzed in the ABI Primer® 3100 Genetic Analyzer using the polymer POP4 and Genetic Analyzer 1× Buffer (following the manufacturer's instructions). The run module was GS_36_POP4e-tag_V02_ 30C_1400s (Pre-Run: 15 KV, 180 s; Injection: 3 KV, 10 s; Run: 15 KV, 1400 s; T=30 C).

When the e-tag probes: a126CT-eR4 (wild type allele) and a126CF-eR18 (mutant allele); a156CT-eR10 (wild type allele) and a156CF-eR20 (mutant allele); a125CT-eR36 (wild type allele) and a125CF-eR34 (mutant allele); and a1CT-eR50 (wild type allele) and a1CF-eR47 (mutant allele) were used to analyze NA17001 (mutant/mutant); NA17002 (wild type/wild type); and NA17003 (wild type/mutant) DNA, each set of e-tag probes was able to detect and distinguish the wild type and mutant alleles.

The results indicate that genotyping using the universal e-tag primer methodology of the invention is generally applicable to a variety of e-tag labels.

In a similar multiplex analysis, NA17003 DNA, heterozygous for the MTHFR C677T SNP, was analyzed using universal e-tag primers and corresponding a126CT-eR4/a126CF-eR18; a156CT-eR10/a156CF-eR20; a125CT-eR36/a125CF-eR34 and a1CT-eR50/a1CF-eR47 e-tag probe sets.

In conducting this analysis, the following reagents were combined and amplification carried out using the ARMS11 cycling conditions set forth below: 3.5 mM $Cl_2Mg$, 0.05 μM specific wild type and mutant MTHFR primers, 0.2 μM e-tag probes, 0.5 μM Universal Primer, 1 U TaqGold, 1× TaqGold Buffer, 100 μM dNTPs, 20 ng DNA in a final volume of 10 μL.

The cycling conditions used in the amplification were from the ARMS11 program, as follows: 12 min at 95° C., 40 seconds at 94° C., 80 seconds at 60° C. for 3 cycles; 40 seconds at 72° C., 40 seconds at 94° C., 80 seconds at 66° C. for 40 cycles, then 20 min at 4° C. and held at 15° C.

The samples were diluted 1/10 in 50% HiDi Formamide-0-0.8 ng/μL avidin -~1/100 RoxT8 and then loaded in the 3100 Genetic Analyzer. RoxT8 was added as an internal reference peak.

The reactions were run and analyzed in the ABI Prism® 3100 Genetic Analyzer using the polymer POP4 and Genetic Analyzer 1× Buffer (following the manufacturer's instructions). The run module was GS_36_POP4-e-tag_,02_ 30C_1400s (Pre-Run: 15 KV, 180 s; Injection : 3 KV, 10 s; Run: 15 KV, 1400 s; T=30 C).

Figure 14:
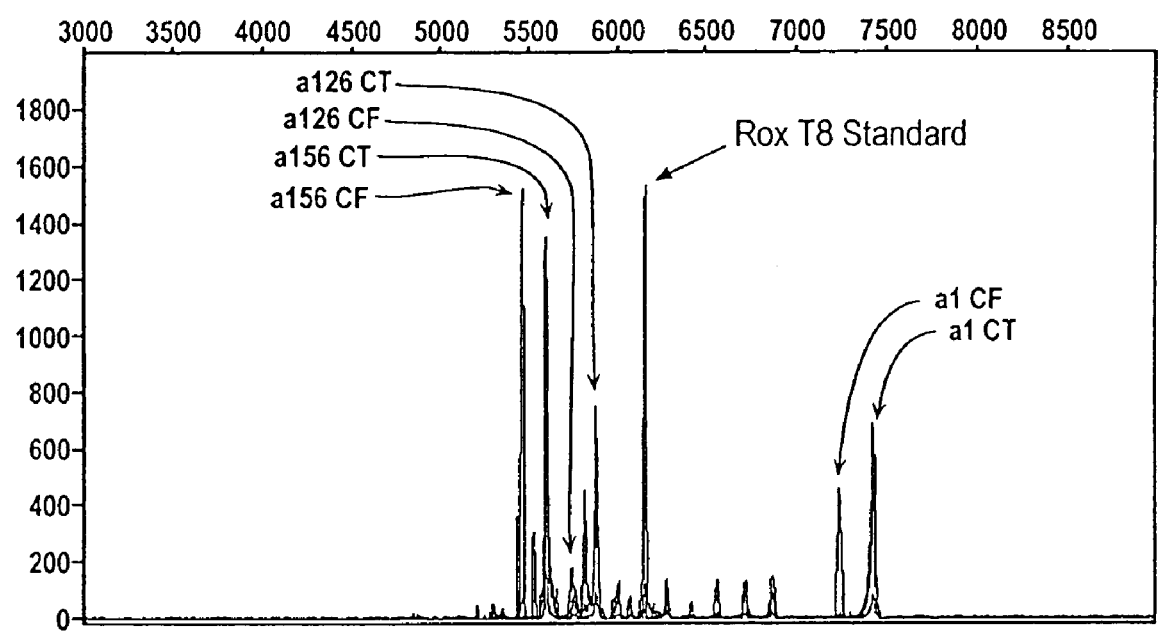
FIG. 14 is an electropherogram illustrating the results of a multiplex assay using the universal e-tag technology of the invention with e-tag-reporter detection by CE using an ABI Prism® 3100 genetic analyzer. The results reflect analysis of NA17003 DNA, heterozygous for the MTHFR C677T SNP, using universal e-tag primers and corresponding a 126CT-eR4/a126CT-eR18; a156CT-eR10/a156CF-eR20; a125CT-eR36/a125CF-eR34 and a 1CT-eR50/a1CF-eR47 e-tag probe sets.

FIG. 14 is an electropherogram illustrating the results of the multiplex assay. The results show that universal e-tag primer methodology of the invention may be used for multiplexed analysis of a nucleic acid sample that is heterozygous for a particular snp with differentiation and detection of the signal generated by 3 different e-tag reporters following CE.

Example 4

Duplex Analysis Using Universal e-Tag Technology

A. Analysis of MTHFR C677T and Factor V Leiden SNPs

A duplex assay for the MTHFR C677T and Factor V Leiden SNPs was carried out using the universal e-tag technology of the invention.

Template DNA samples designated NA17001 (Factor V wild type/wild type; MTHFR genotype mutant/mutant); NA17002 (Factor V wild type/wild type; MTHFR genotype wild type/wild type); and NA17003 (Factor V wild type/wild type; MTHFR genotype wild type/mutant) together with water as a negative control, were amplified in a competitive assay format with the MTHFR wild type and mutant specific universal e-tag primers and the Factor V wild type and mutant universal e-tag specific primers together with the corresponding e-tag probes.

In conducting this analysis, the following reagents were combined and amplification carried out using the ARMS11 cycling conditions set forth below: 2.5 mM Cl$_2$Mg, 0.05 µM MTHFR wild type and mutant specific primers, 0.05 µFactor V M wild type and mutant specific primers, 0.2 µM e-tag Factor V a126CT-eR4 and a126CF-eR18 e-tag probes, 0.2 µM MTHFR a156CT-eR10 a156CF-eR20 e-tag probes, 0.5 µM Universal Primer, 2 U TaqGold, 1× TaqGold Buffer, 100 µM dNTPs, 20 ng DNA in a final volume of 10 µL.

The cycling conditions used in the amplification were from the ARMS11 program, as follows: 12 min at 95° C., 40 seconds at 94° C., 80 seconds at 60° C. for 3 cycles; 40 seconds at 72° C., 40 seconds at 94° C., 80 seconds at 66° C. for 40 cycles, then 20 min at 4° C. and held at 15° C.

The samples were diluted 1/10 in 50% HiDi Formamide-0-0.8 ng/µL avidin -~500 pM Fluorescein Na$^+$ and then loaded in the 3100 Genetic Analyzer. Fluroescein was added as an internal reference peak.

The reactions were run and analyzed in the ABI Prism® 3100 Genetic Analyzer using the polymer POP4 and Genetic Analyzer 1× Buffer (following the manufacturer's instructions). The run module was GS_36_POP4e-tag_v02_30C_1400s (Pre-Run: 15 KV, 180 s; Injection: 3 KV, 10 s; Run: 15 KV, 1400 s; T=30 C).

B. Analysis of MTHFR C677 T and ApoE112 SNPs

A similar experiment was carried out using a competitive assay format for the analysis of previously characterized template DNA including universal e-tag primers specific for MTHFR and ApoE112 wild type and mutant alleles, respectively and corresponding e-tag probe sets.

Template DNA samples designated NA14308 (ApoE112 genotype wt/mt; MTHFR genotype wt/wt); NA14311 (ApoE genotype mt/mt; MTHFR genotype wt/wt); NA17031 (ApoE genotype wt/wt; MTHFR genotype wt/wt); NA17032 (ApoE genotype wt/wt; MTHFR genotype mt/mt) and NA17033 (ApoE genotype wt/wt; MTHFR genotype wt/mt) together with water as a negative control, were amplified in a competitive assay format with the MTHFR wild type and mutant specific universal e-tag primers and the ApoE112 wild type and mutant universal e-tag specific primers together with the corresponding e-tag probes: a156CT-eR10 (allele C677, wild type)/a156CT-eR20 (allele T677, mutant type) and ApoE112 a1CT-eR50 (allele T, wild type)/ApoE112 a1CF-eR47 (allele C, mutant type).

In conducting this analysis, the following reagents were combined and amplification carried out usng the ARMS11 cycling conditions set forth below: 2.5 mM Cl$_2$Mg, 0.05 µM MTHFR wild type and mutant specific primers, 0.25 µM ApoE112 wild type and mutant specific primers, 0.2 µM MTHFR e-tag probes, 0.4 µM e-tag ApoE112 probes, 0.5 µM Universal Primer, 2 U TaqGold, 1× TaqGold Buffer, 100 µM dNTPs, 15% glycerol, 20 ng DNA in a final volume of 10 µL.

The cycling conditions used in the amplification were from the ARMS11 program, as follows: 12 min at 95° C., 40 seconds at 94° C., 80 seconds at 60 ° C. for 3 cycles; 40 seconds at 72° C., 40 seconds at 94° C., 80 seconds at 66° C. for 40 cycles, then 20 min at 4° C. and held at 15° C.

Before the run, the samples were diluted 1/10 in 50% HiDi Formamide-0-0.8 ng/µL avidin-~1/10 RoxT8 and then loaded in the 3100 Genetic Analyzer. RoxT8 was added as an internal reference peak.

The reaction were run and analyzed in the ABI Primer® 3100 Genetic Analyzer using the polymer POP4 and Genetic Analyzer 1× Buffer (following the manufacturer's instructions). The run module was GS_36_POP4e-tag_v02_30C_1400s (Pre-Run: 15 KV, 180 s; Injection: 3 KV, 10 s; Run: 15 KV, 1400 s; T=30 C).

The results confirmed that consistent with the MTHFR C677 T/Factor V Leiden study, the universal e-tag technology of the invention can be used in multiplexed across more than one polymorphic locus in a single assay in a competitive assay format.

TABLE 9

DESCRIPTION OF SEQUENCES

Description

FactorV-leiden gs_primerFVwt TACTTCAAGGACAAAATACCTGTATTCCGC
(SEQ ID NO:4)

FactorV-leiden gs_primerFVmt TACTTCAAGGACAAAATACCTGTATTCCAT
(SEQ ID NO:5)

FactorV-leiden com_primerV: CAGGGGAAACCTATACTTATAAGTGGAACATC
(SEQ ID NO:6)

ApoE158 gs_primer158_T: ATGCCGATGACCTGCAGAATT
(SEQ ID NO:82)

ApoE158 gs_primer158_C: ATGCCGATGACCTGCAGAATC
(SEQ ID NO:83)

ApoE158 comp_158 (cv): CCTCGCGGATGGCGCTGA
(SEQ ID NO:84)

ApoE112 gs_primer112_T: CGCGGACATGGAGGACGTTT
(SEQ ID NO:7)

ApoE112 gs_primer112_C: CGCGGACATGGAGGACGTTC
(SEQ ID NO:8)

ApoE112 com_p112 (cv): GAGCATGGCCTGCACCTC
(SEQ ID NO:9)

TABLE 9-continued

DESCRIPTION OF SEQUENCES

Description

MTHFR gs_pMTHFRwt: GAAGGAGAAGGTGTCTGCGGTAGC
(SEQ ID NO:1)

MTHFR gs_pMTHFRmt: GAAGGAGAAGGTGTCTGCGGAAGT
(SEQ ID NO:2)

MTHFR com_pMTHFR: AGGACGGTGCGGTGAGAGTG
(SEQ ID NO:10)

eR1 CGCGATTGGCGTCGTCTGAGCGCCTTTAAA
(SEQ ID NO:11)

eR3 CAGCCACACAGAGCGCE-TAGTTCCAATGAC
(SEQ ID NO:13)

eR4 CGGCGTAGCCCTCTCCGTCGTCCTGTGTCC
(SEQ ID NO:14)

eR5 CGACGCTTTGCAGATGATATACTTGCGCGG
(SEQ ID NO:15)

eR6 CCGTGGATCAGCCTGCCCGATTCCGTCACA
(SEQ ID NO:16)

eR9 CCTGTTGCGCCCTGAAGACAAGAGATTTCG
(SEQ ID NO:19)

eR10 CGAGCAACCGGTCCGTCTCTACCCTAAACG
(SEQ ID NO:20)

eR11 CGAAGCGTAGGTCAACCCTGAGCGTGCGAT
(SEQ ID NO:21)

eR12 CGCGAGCGCTAGTGAACGTACCTAGATTTC
(SEQ ID NO:22)

eR18 CATCATTCTATCGCGACAACGCGGGCCGAA
(SEQ ID NO:85)

eR20 CCGTTCGCGTAGTGCCGAGGGCATCAATTA
(SEQ ID NO:30)

eR21 CCACGCCTCCTATTTGTCTTCAGCCGCGTC
(SEQ ID NO:31)

eR22 CAGGTTCGCACTCAGTCTTTCCAAGGCGCG
(SEQ ID NO:32)

eR34 CTCGGCACGGTTCTACGGAGTGCATAGCGA
(SEQ ID NO:36)

eR36 CTACTTGCCTTCGCGTAGTGGAGGAGAGTT
(SEQ ID NO:38)

eR38 CTCGACCGCCAATCCGCAATATGAGCCATG
(SEQ ID NO:40)

eR42 CTGAACAATGCCGCGACAATGGAGCTGAAG
(SEQ ID NO:44)

eR45 CTGAGACGATAGGGCCGCTTATTGCACCCT
(SEQ ID NO:47)

eR47 CTACGCACCTATGACGCGCCTAACCTTTGG
(SEQ ID NO:49)

eR50 CTCAGGAAGGGCGAAGCGTTCCCTGCCAAT
(SEQ ID NO:52)

Up_M1 universal primer sequence: AGGTCCACTGCGTCCGATGT
(SEQ ID NO:53)

Up_M1 universal primer sequence + Spacer AGGTCCACTGCGTCCGATGTTCGACT
(SEQ ID NO:54)

TABLE 9-continued

DESCRIPTION OF SEQUENCES

Description

Up_M2 universal primer sequence: TTGGCAGCTCTCGGCATCAG
(SEQ ID NO:55)

Up_M2 universal primer sequence + Spacer TTGGCAGCTCTCGGCATCAGTCGACT
(SEQ ID NO:56)

Up_M3 universal primer sequence: TGAAGACCGTCGTCGCGTAC
(SEQ ID NO:57)

Up_M3 universal primer sequence + Spacer TGAAGACCGTCGTCGCGTACTCGACT
(SEQ ID NO:58)

4FVw universal e-tag primer
AGGTCCACTGCGTCCGATGTTCGACTCGGCGTAGCCCTCTCCGTCGTCCTGTGT
CCTACTTCAAGGACAAAATACCTGTATTCCGC (SEQ ID NO:59)

18FVm universal e-tag primer
AGGTCCACTGCGTCCGATGTTCGACTCATCATTCTATCGCGACAACGCGGGCCGA
ATACTTCAAGGACAAAATACCTGTATTCCAT (SEQ ID NO:60)

CFVr universal e-tag primer
AGGTCCACTGCGTCCGATGTCAGGGGAAACCTATACTTATAAGTGGAACATC
(SEQ ID NO:61)

10MTHFRw universal e-tag primer
AGGTCCACTGCGTCCGATGTTCGACTCGAGCAACCGGTCCGTCTCTACCCTAAAC
GGAAGGAGAAGGTGTCTGCGGTAGC (SEQ ID NO:62)

20MTHFRm universal e-tag primer
AGGTCCACTGCGTCCGATGTTCGACTCCGTTCGCGTAGTGCCGAGGGCATCAAT
TAGAAGGAGAAGGTGTCTGCGGAAGT (SEQ ID NO:63)

CMTHFRr universal e-tag primer
AGGTCCACTGCGTCCGATGTAGGACGGTGCGGTGAGAGTG
(SEQ ID NO:64)

34E158T universal e-tag primer
AGGTCCACTGCGTCCGATGTTCGACTCTCGGCACGGTTCTACGGAGTGCATAGC
GAgATGCCGATGACCTGCAGAATT (SEQ ID NO:86)

36E158C universal e-tag primer
AGGTCCACTGCGTCCGATGTTCGACTCTACTTGCCTTCGCGTAGTGGAGGAGAGT
TATGCCGATGACCTGCAGAATC (SEQ ID NO:87)

cE158r universal e-tag primer
AGGTCCACTGCGTCCGATGTCCTCGCGGATGGCGCTGA
(SEQ ID NO:88)

50E112T universal e-tag primer
AGGTCCACTGCGTCCGATGTTCGACTCTCAGGAAGGGCGAAGCGTTCCCTGCCA
ATCGCGGACATGGAGGACGTTT (SEQ ID NO:65)

47E112C universal e-tag primer
AGGTCCACTGCGTCCGATGTTCGACTCTACGCACCTATGACGCGCCTAACCTTTG
GCGCGGACATGGAGGACGTTC (SEQ ID NO:66)

cE112r
AGGTCCACTGCGTCCGATGTGAGCATGGCCTGCACCTC
(SEQ ID NO:67)

a126CT-eR4
TET-(M5)2-CG*G*C*GTAGCCCTCTCCGTCGTCCTGTGTCC-biotin
(SEQ ID NO:68)

a126CF-eR18
6-FAM-(M5)2-CA*T*C*ATTCTATCGCGACAACGCGGGCCGAA-biotin
(SEQ ID NO:69)

a156CT-eR10
TET-(M2)2-CG*A*G*CAACCGGTCCGTCTCTACCCTAAACG-biotin
(SEQ ID NO:70)

TABLE 9-continued

DESCRIPTION OF SEQUENCES

Description a156CF-eR20
6-FAM-(M2)2-CC*G*T*TCGCGTAGTGCCGAGGGCATCAATTA-biotin
(SEQ ID NO:71)

a156CF-eR20
6-FAM-(M2)2-CC*G*T*TCGCGTAGTGCCGAGGGCATCAATTA-biotin
(SEQ ID NO:71)

a125CT-eR36
TET-(M5)-CT*A*C*TTGCCTTCGCGTAGTGGAGGAGAGTT-biotin
(SEQ ID NO:72)

a125CF-eR34
6-FAM-(M5)-CT*C*G*GCACGGTTCTACGGAGTGCATAGCGA-biotin
(SEQ ID NO:73)

a1CT-eR50
TET-CT*C*A*GGAAGGGCGAAGCGTTCCCTGCCAAT-biotin
(SEQ ID NO:74)

a1CF-eR47
6-FAM-CT*A*C*GCACCTATGACGCGCCTAACCTTTGG-biotin
(SEQ ID NO:75)

It is evident from the above results that the subject invention provides methods and kits for the multiplexed determination of nucleic acid targets. The methods provide for homogeneous and heterogeneous protocols. In nucleic acid determination, SNP determinations are greatly simplified where a multiplex assay that distinguishes alleles of a number of gene loci can be performed in a single reaction mixture and a large number of SNPs can be readily determined within a short period of time. It is further evident from the above results that the subject invention provides an accurate, efficient and sensitive process for multiplexed nucleic acid determinations.

All publications and patent applicatoins cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

The invention claimed is:

1. A method of detecting each or any of a plurality of known, selected nucleotide target sequences, comprising:
   (a) mixing the target sequences with (i) a set of forward universal e-tag primers, each member of the set containing (ia) a target sequence that is complementary to one of the known selected target sequences, and (ib) an extension sequence which is unique to the target sequence of that member, (ii) one or more reverse primers that are complementary to said target sequences, and (iii) enzyme and nucleotide components of a primer extension reaction, to form a target-sequence reaction mixture;
   (b) reacting the reaction mixture under primer extension reaction conditions, to form extended target sequences,
   (c) reacting, under hybridization conditions, the extended target sequences with a set of electrophoretic tag (e-tag) probes, each member of the tag probe set having (i) an oligonucleotide portion that is complementary to one of said extension sequences, (ii) an electrophoretic probe having an electrophoretic mobility that is unique to a given extension sequence, and (iii) a linker joining the oligonucleotide portion and the electrophoretic probe, said linker being cleavable under selected conditions when the oligonucleotide portion of said probe is bound to a complementary target extension sequence, (d) treating the target sequences under said selected conditions, to release an e-tag reporter from each e-tag probe bound to a target sequence, (e) separating the released reporters electrophoretically, and (f) detecting separated released reporters, thereby to identify target sequences that hybridized to said probes.

2. The method of claim 1, wherein said extension sequence includes, in a 5'-to-3' direction, a universal primer extension sequence and an e-tag-probe extension sequence, step (c) includes reacting the extended target sequences with the e-tag probes and with an upstream probe or probes capable of hybridizing to said universal primer extension sequence, and step (d) includes treating the target sequences with a cleaving agent capable of cleaving said linker only when the extension sequence has both an upstream probe and a tag probe hybridized thereto.

3. The method of claim 2, wherein the cleaving agent is a DNA polymerase having 5'-exonuclease activity, and said linker is a nucleotide linked to the 5' end of the oligonucleotide portion through a nuclease cleavable bond.

4. The method of claim 2, wherein the cleaving agent is a restriction enzyme, and said linker includes the specific sequence cleaves by said restriction enzyme.

5. The method of claim 2, wherein said cleaving agent is a sensitizer capable of generating activated oxygen under conditions of light illumnation.

6. The method of claim 1, wherein the tag probes in a set have the form $(D, M_j)$-N-$T_j$, which are cleaved to an electrophoretic tag reporter of the form $(D, M_j)$-N', where (i) D is a detection group comprising a detectable label or a catalytic group capable of catalyzing a detectable reaction;

(ii) Tj is an oligonucleotide target-binding moiety for binding an e-tag probe recognition sequence;

(iii) N is a linker joined to the 5'-end nucleotide in Tj through a cleavable bond;

(iv) N' is the residue of N remaining after cleavage;

(v) Mj is a mobility modifier having a charge/mass ratio that imparts to the corresponding electrophoretic tag, an electrophoretic mobility that is unique to a given extension sequence, and (vi) (D, Mj)-includes both D-Mj- and Mj -D-.

7. The method of claim 6, wherein N is a nucleotide, and each e-tag probe target binding moiety contains at least one modification selected from a nuclease-resistant bond joining at least the two 5'-end nucleotides of the target binding moiety, or a capture ligand contained on the '5-end nucleotide of the target binding moiety and capable of binding specifically to a capture agent.

8. The method of claim 6, wherein N is a linkage cleavable by singlet oxygen.

9. The method of claim 1, wherein the e-tag probes in a set have the form:

(D, Mj)n-B-N-Tj, which are cleaved in step (d) under said selected conditions to a branched structure (D, Mj)n-B-N', and are further cleaved to a plurality of electrophoretic tags of the form (D, Mj)-B', where (i) D is a detection group comprising a detectable label or a catalytic group capable of catalyzing a detectable reaction;

(ii) Tj is an oligonucleotide target-binding moiety for binding an e-tag probe recognition sequence;

(iii) B is a branched polymer having n electrophoretic tags probes attached thereto, each through a linkage that is cleavage under cleavage conditions different from said selected conditions employed in step (d);

(iv) B' is the residue of B remaining after cleavage of the electrophoretic probes from the branched structure;

(v) N' is the residue of N remaining after cleavage of the branched structure from said probe, (vi) Mj is a mobility modifier having a charge/mass ratio that imparts to the corresponding electrophoretic tag, an electrophoretic mobility that is unique to a given extension sequence, and (vii) (D, Mj)- includes both D-Mj- and Mj-D-, and wherein said treating step includes treating bound probe under said selected condtions to release branched structures in probes hybridized with target sequences, and further treating the released branched structures under said different cleavage condtions, to release electrophoretic probes from the branched structures.

10. The method of claim 9, wherein each of the target binding moieties contains at least one modification selected from a nuclease-resistant bond joining at least the two 5'-end nucleotides of the target binding moiety, or a capture ligand contained on the '5-end nucleotide of the target binding moiety and capable of binding specifically to a capture agent.

11. A kit for detecting each or any of a plurality of known, selected nucleotide target sequences, comprising:

(a) a set of forward oligonucleotide primers, each member of the set containing (ia) a target-sequence that is complementary to one of the known selected target sequences, and (ib) an extension sequence which is unique to the target sequence of that member, (b) one or more reverse primers that are complementary to said target sequences, said forward and reverse primers being effective, in the presence enzyme and nucleotide components of a primer extension reaction, to form amplified, extended target sequences, and (c) a set of electrophoretic tag (e-tag) probes, each member of the tag probe set having (i) an oligonucleotide portion that is complementary to one of said extension sequences, (ii) an electrophoretic probe having an electrophoretic mobility that is unique to a given extension sequence, and (iii) a linker joining the oligonucleotide portion and the electrophoretic probe, said linker being cleavable under selected conditions when the oligonucleotide portion of said probe is bound to a complementary target extension sequence.

12. The kit of claim 11, which further includes enzymes and nucleotide components of a PCR reaction.

13. The kit of claim 11, wherein said extension sequence includes in a 5'-to-3' direction, a universal primer extension sequence and an e-tag-probe extension sequence, wherein said kit further includes one or more upstream primers capable of hybridizing to said universal primer extension sequence.

14. The kit of claim 13, for use with a DNA polymerase having 5'-exonuclease activity to cleave said probe, wherein said probe linker is a nucleotide linked to the 5' end of the oligonucleotide portion through a nuclease cleavable bond.

15. The kit of claim 13, for use with a sensitizer wherein singlet oxygen is generated by photoactivation of said sensitizer, and said one or more upstream primers include a moiety capable of generating singlet oxygen in the presence of light.

16. The kit of claim 11, for use with a restriction enzyme wherein said probe linker includes or is the specific sequence cleaved by said restriction enzyme.

17. The kit of claim 11, wherein the tag probes in a set have the form (D, Mj)-N-Tj, which are cleaved to an electrophoretic tag of the form (D, Mj)-N', where
(i) D is a detection group comprising a detectable label or a catalytic group capable of catalyzing a detectable reaction;
(ii) Tj is an oligonucleotide target-binding moiety for binding an e-tag probe recognition sequence;
(iii) N is a linker joined to the 5'-end nucleotide in Tj through a cleavable bond;
(iv) N' is the residue of N remaining in after cleavage;
(v) Mj is a mobility modifier having a charge/mass ratio that imparts to the corresponding electrophoretic tag, an electrophoretic mobility that is unique to a given extension sequence; and
(vi) (D, Mj)- includes D-Mj- and Mj-D-.

18. The kit of claim 17, wherein N is a nucleotide and each of the e-tag probe recognition sequence-binding moieties contains at least one modification selected from a nuclease-resistant bond joining at least the two 5'-end nucleotides of the recognition sequence, or a capture ligand contained on the '5-end nucleotide of the recognition sequence and capable of binding specifically to a capture agent.

19. The kit of claim 11, wherein the tag probes in a set have the form:
(D, Mj)n-B-N-Tj, which are cleaved in step (d) under said selected conditions to a branched structure (D, Mj)n-B-N', and are further cleaved to a plurality of electrophoretic tags of the form (D, Mj)-B', where
(i) D is a detection group comprising a detectable label or a catalytic group capable of catalyzing a detectable reaction;
(ii) Tj is an oligonucleotide target-binding moeity;
(iii) B is a branched polymer having n electrophoretic tags probes attached thereto, each through a linkage that is cleavage under cleavage conditions different from said selected conditions employed in step (d);
(iv) B' is the residue of B remaining after cleavage of the electrophoretic probes from the branched structure;
(v) N is a linker joined to the 5'-end nucleotide in Tj through a cleavable bond; and N' is the residue of N remaining after cleavage of the branched structure from said probe;
(vi) Mj is a mobility modifier having a charge/mass ratio that imparts to the corresponding electrophoretic tag, an electrophoretic mobility that is unique to a given extension sequence; and
(vii) (D, Mj)- includes both D-Mj- and Mj-D-.

20. The kit of claim 19, wherein N is a nucelotide and each e-tag probe target binding moiety contains at least one modification selected from a nuclease-resistant bond joining at least the 5'-end nucleotides of the recognition sequence, or a capture ligand contained on the '5-end of the target binding moiety and capable of binding specifically to a capture agent.

21. The kit of claim 20, further comprising a cleaving moiety selected from the group consisting of a 5' exonuclease, a restriction enzyme, an RNase, a protease and an esterase.

* * * * *

SEQUENCE LISTING

<160> NUMBER OF SEQ ID NOS: 88

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
gaaggagaag gtgtctgcgg tagc                                    24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
gaaggagaag gtgtctgcgg aagt                                    24

```
<210> SEQ ID NO 3
<211> LENGTH: 24
<212> TYPE: DNA
<213> ORGANISM: Artificial Sequence
<220> FEATURE:
<223> OTHER INFORMATION: template
<220> FEATURE:
<221> NAME/KEY: misc_feature
<222> LOCATION: (1)...(24)
<223> OTHER INFORMATION: n = A,T,C or G

<400> SEQUENCE: 3
gaaggagaag gtgtctgcgg gagn                                           24

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
tacttcaagg acaaaatacc tgtattccgc                                     30

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
tacttcaagg acaaaatacc tgtattccat                                     30

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
caggggaaac ctatacttat aagtggaaca tc                                  32

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cgcggacatg gaggacgttt                                                20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgcggacatg gaggacgttc                                                20

<210> SEQ ID NO 9
<211> LENGTH: 18
<212> TYPE: DNA
```

```
<213> ORGANISM: Artificial Sequence
<220> FEATURE:
<223> OTHER INFORMATION: primer

<400> SEQUENCE: 9
gagcatggcc tgcacctc                                                 18

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aggacggtgc ggtgagagtg                                               20

<210> SEQ ID NO 11
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 11
cgcgattggc gtcgtctgag cgcctttaaa                                    30

<210> SEQ ID NO 12
<211> LENGTH: 26
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (13)...(14)
<223> OTHER INFORMATION: e-tag modification

<400> SEQUENCE: 12
ccatgccaac tacctgccgt gaacaa                                        26

<210> SEQ ID NO 13
<211> LENGTH: 26
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (16)...(17)
<223> OTHER INFORMATION: e-tag modification

<400> SEQUENCE: 13
cagccacaca gagcgcttcc aatgac                                        26

<210> SEQ ID NO 14
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 14
cggcgtagcc ctctccgtcg tcctgtgtcc                                    30

<210> SEQ ID NO 15
<211> LENGTH: 30
```

<212> TYPE: DNA
<213> ORGANISM: Artificial Sequence
<220> FEATURE:
<223> OTHER INFORMATION: e-tag reporter sequence

<400> SEQUENCE: 15
cgacgctttg cagatgatat acttgcgcgg          30

<210> SEQ ID NO 16
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 16
ccgtggatca gcctgcccga ttccgtcaca          30

<210> SEQ ID NO 17
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 17
cggccttcat agcgaagtta cccggcttta          30

<210> SEQ ID NO 18
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 18
catccgcagg tagaatgacg ggaagccgat          30

<210> SEQ ID NO 19
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 19
cctgttgcgc cctgaagaca agagatttcg          30

<210> SEQ ID NO 20
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 20
cgagcaaccg gtccgtctct accctaaacg          30

<210> SEQ ID NO 21
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 21
cgaagcgtag gtcaaccctg agcgtgcgat         30

<210> SEQ ID NO 22
<211> LENGTH: 22
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (8)...(9)
<223> OTHER INFORMATION: e-tag modification
<220> FEATURE:
<221> NAME/KEY: misc_feature
<222> LOCATION: (17)...(18)
<223> OTHER INFORMATION: e-tag modification

<400> SEQUENCE: 22
cgcgagcgtg aacgtacatt tc         22

<210> SEQ ID NO 23
<211> LENGTH: 26
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (14)...(15)
<223> OTHER INFORMATION: e-tag modification

<400> SEQUENCE: 23
ctgagatgtg tggtgcggca ggcgaa         26

<210> SEQ ID NO 24
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 24
caactgtcgg gacattaacg gtgggcagca         30

<210> SEQ ID NO 25
<211> LENGTH: 26
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (1)...(1)
<223> OTHER INFORMATION: e-tag modification to 5' end

<400> SEQUENCE: 25
tcgaacaagg cggtaaacgc caaagc         26

<210> SEQ ID NO 26
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 26
cccagtgcta tagcaccggc tcgcatggat         30

```
<210> SEQ ID NO 27
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 27
cccacccgtt gttgtttcga gactcgcaca                                    30

<210> SEQ ID NO 28
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 28
catcattcta tcgcgacaac gcgggccgaa                                    30

<210> SEQ ID NO 29
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 29
cctcgagtac ctttgcacga acctcctacg                                    30

<210> SEQ ID NO 30
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 30
ccgttcgcgt agtgccgagg gcatcaatta                                    30

<210> SEQ ID NO 31
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 31
ccacgcctcc tatttgtctt cagccgcgtc                                    30

<210> SEQ ID NO 32
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 32
caggttcgca ctcagtcttt ccaaggcgcg                                    30

<210> SEQ ID NO 33
<211> LENGTH: 26
<212> TYPE: DNA
<213> ORGANISM: Artificial Sequence
<220> FEATURE:
<223> OTHER INFORMATION: e-tag reporter sequence
<220> FEATURE:
```

```
<221> NAME/KEY: misc_feature
<222> LOCATION: (1)...(1)
<223> OTHER INFORMATION: e-tag modification to 5' end

<400> SEQUENCE: 33
taccaaggtg gcgaacgaga ccaggc                                          26

<210> SEQ ID NO 34
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 34
ctttggcctt gagaatgagc agatgacggg                                      30

<210> SEQ ID NO 35
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 35
ctcaggctca gccaatggta agactgcggg                                      30

<210> SEQ ID NO 36
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 36
ctcggcacgg ttctacggag tgcatagcga                                      30

<210> SEQ ID NO 37
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 37
ctgtatcatc attcacggct gcagggccct                                      30

<210> SEQ ID NO 38
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 38
ctacttgcct tcgcgtagtg gaggagagtt                                      30

<210> SEQ ID NO 39
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 39
ctcggtcggg ctacacttcc tgttaaggca                                      30
```

<210> SEQ ID NO 40
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 40
ctcgaccgcc aatccgcaat atgagccatg           30

<210> SEQ ID NO 41
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 41 ctccccggagc gtgcagacta tccaggtgta           30

<210> SEQ ID NO 42
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 42
ctgcattgtg gcagcttacc atgcaggttg           30

<210> SEQ ID NO 43
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 43
ctcgctggag tctgaaaggc cagagataca           30

<210> SEQ ID NO 44
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 44
ctgaacaatg ccgcgacaat ggagctgaag           30

<210> SEQ ID NO 45
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 45
ctcagatcca cgtaaatggg cagcttgcgt           30

<210> SEQ ID NO 46
<211> LENGTH: 30
<212> TYPE: DNA
<213> ORGANISM: Artificial Sequence
<220> FEATURE:

<223> OTHER INFORMATION: e-tag reporter sequence

<400> SEQUENCE: 46
ctaccagata ggcttcctgc gtcaatccgg            30

<210> SEQ ID NO 47
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 47
ctgagacgat agggccgctt attgcaccct            30

<210> SEQ ID NO 48
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 48
ctttgggtga gagccaacag tggactggca            30

<210> SEQ ID NO 49
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 49
ctacgcacct atgacgcgcc taacctttgg            30

<210> SEQ ID NO 50
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 50
ctgagctggc tacagccacc gggttagagt            30

<210> SEQ ID NO 51
<211> LENGTH: 26
<212> TYPE: DNA
<213> ORGANISM: Artificial Sequence
<220> FEATURE:
<223> OTHER INFORMATION: e-tag reporter sequence
<220> FEATURE:
<221> NAME/KEY: misc_feature
<222> LOCATION: (1)...(1)
<223> OTHER INFORMATION: e-tag modification to 5' end

<400> SEQUENCE: 51
atcttacaga atccgccgcg caattg            26

<210> SEQ ID NO 52
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 52

```
ctcaggaagg gcgaagcgtt ccctgccaat                                              30
```

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53

```
aggtccactg cgtccgatgt                                                         20
```

<210> SEQ ID NO 54
<211> LENGTH: 26
<212> TYPE: DNA
<213> ORGANISM: Artificial Sequence
<220> FEATURE:
<223> OTHER INFORMATION: primer

<400> SEQUENCE: 54

```
aggtccactg cgtccgatgt tcgact                                                  26
```

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55

```
ttggcagctc tcggcatcag                                                         20
```

<210> SEQ ID NO 56
<211> LENGTH: 26
<212> TYPE: DNA
<213> ORGANISM: Artificial Sequence
<220> FEATURE:
<223> OTHER INFORMATION: primer

<400> SEQUENCE: 56

```
ttggcagctc tcggcatcag tcgact                                                  26
```

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57

```
tgaagaccgt cgtcgcgtac                                                         20
```

<210> SEQ ID NO 58
<211> LENGTH: 26
<212> TYPE: DNA
<213> ORGANISM: Artificial Sequence
<220> FEATURE:
<223> OTHER INFORMATION: primer

<400> SEQUENCE: 58

```
tgaagaccgt cgtcgcgtac tcgact                                                  26
```

<210> SEQ ID NO 59
<211> LENGTH: 86
<212> TYPE: DNA

<213> ORGANISM: Artificial Sequence
<220> FEATURE:
<223> OTHER INFORMATION: primer

<400> SEQUENCE: 59
aggtccactg cgtccgatgt tcgactcggc gtagccctct ccgtcgtcct gtgtcctact    60
tcaaggacaa aatacctgta ttccgc    86

<210> SEQ ID NO 60
<211> LENGTH: 86
<212> TYPE: DNA
<213> ORGANISM: Artificial Sequence
<220> FEATURE:
<223> OTHER INFORMATION: primer

<400> SEQUENCE: 60
aggtccactg cgtccgatgt tcgactcatc attctatcgc gacaacgcgg gccgaatact    60
tcaaggacaa aatacctgta ttccat    86

<210> SEQ ID NO 61
<211> LENGTH: 52
<212> TYPE: DNA
<213> ORGANISM: Artificial Sequence
<220> FEATURE:
<223> OTHER INFORMATION: primer

<400> SEQUENCE: 61
aggtccactg cgtccgatgt caggggaaac ctatacttat aagtggaaca tc    52

<210> SEQ ID NO 62
<211> LENGTH: 80
<212> TYPE: DNA
<213> ORGANISM: Artificial Sequence
<220> FEATURE:
<223> OTHER INFORMATION: primer

<400> SEQUENCE: 62
aggtccactg cgtccgatgt tcgactcgag caaccggtcc gtctctaccc taaacggaag    60
gagaaggtgt ctgcggtagc    80

<210> SEQ ID NO 63
<211> LENGTH: 80
<212> TYPE: DNA
<213> ORGANISM: Artificial Sequence
<220> FEATURE:
<223> OTHER INFORMATION: primer

<400> SEQUENCE: 63
aggtccactg cgtccgatgt tcgactccgt tcgcgtagtg ccgagggcat caattagaag    60
gagaaggtgt ctgcggaagt    80

<210> SEQ ID NO 64
<211> LENGTH: 40
<212> TYPE: DNA
<213> ORGANISM: Artificial Sequence
<220> FEATURE:
<223> OTHER INFORMATION: primer

<400> SEQUENCE: 64
aggtccactg cgtccgatgt aggacggtgc ggtgagagtg    40

<210> SEQ ID NO 65
<211> LENGTH: 76

```
<212> TYPE: DNA
<213> ORGANISM: Artificial Sequence
<220> FEATURE:
<223> OTHER INFORMATION: primer

<400> SEQUENCE: 65
aggtccactg cgtccgatgt tcgactctca ggaagggcga agcgttccct gccaatcgcg      60
gacatggagg acgttt                                                      76

<210> SEQ ID NO 66
<211> LENGTH: 76
<212> TYPE: DNA
<213> ORGANISM: Artificial Sequence
<220> FEATURE:
<223> OTHER INFORMATION: primer

<400> SEQUENCE: 66
aggtccactg cgtccgatgt tcgactctac gcacctatga cgcgcctaac ctttggcgcg      60
gacatggagg acgttc                                                      76

<210> SEQ ID NO 67
<211> LENGTH: 38
<212> TYPE: DNA
<213> ORGANISM: Artificial Sequence
<220> FEATURE:
<223> OTHER INFORMATION: primer

<400> SEQUENCE: 67
aggtccactg cgtccgatgt gagcatggcc tgcacctc                              38

<210> SEQ ID NO 68
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET

<400> SEQUENCE: 68
cggcgtagcc ctctccgtcg tcctgtgtcc                                       30

<210> SEQ ID NO 69
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
```

-continued

<223> OTHER INFORMATION: 5' nucleotide linked to 6-FAM

<400> SEQUENCE: 69
catcattcta tcgcgacaac gcgggccgaa                                30

<210> SEQ ID NO 70
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET

<400> SEQUENCE: 70
cgagcaaccg gtccgtctct accctaaacg                                30

<210> SEQ ID NO 71
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to 6-FAM

<400> SEQUENCE: 71
ccgttcgcgt agtgccgagg gcatcaatta                                30

<210> SEQ ID NO 72
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET

<400> SEQUENCE: 72
ctacttgcct tcgcgtagtg gaggagagtt                                30

<210> SEQ ID NO 73
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to 6-FAM

<400> SEQUENCE: 73
ctcggcacgg ttctacggag tgcatagcga                               30

<210> SEQ ID NO 74
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET

<400> SEQUENCE: 74
ctcaggaagg gcgaagcgtt ccctgccaat                               30

<210> SEQ ID NO 75
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to 6-FAM

<400> SEQUENCE: 75
ctacgcacct atgacgcgcc taacctttgg                               30

<210> SEQ ID NO 76
<211> LENGTH: 30
<212> TYPE: DNA
<213> ORGANISM: Artificial Sequence
<220> FEATURE:
<223> OTHER INFORMATION: probe
<220> FEATURE:

<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET(M5)2

<400> SEQUENCE: 76
cggcgtagcc ctctccgtcg tcctgtgtcc                     30

<210> SEQ ID NO 77
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to 6-FAM(M5)2

<400> SEQUENCE: 77
catcattcta tcgcgacaac gcgggccgaa                     30

<210> SEQ ID NO 78
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET(M2)2

<400> SEQUENCE: 78
cgagcaaccg gtccgtctct accctaaacg                     30

<210> SEQ ID NO 79
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin

```
<220> FEATURE:
<221> NAME/KEY: misc_feature
<222> LOCATION: 1
<223> OTHER INFORMATION: 5' nucleotide linked to 6-FAM((M2)2

<400> SEQUENCE: 79
ccgttcgcgt agtgccgagg gcatcaatta                                    30

<210> SEQ ID NO 80
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to TET(M5)

<400> SEQUENCE: 80
ctacttgcct tcgcgtagtg gaggagagtt                                    30

<210> SEQ ID NO 81
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (2)...(5)
<223> OTHER INFORMATION: chimeric phosphorothioate modification
<220> FEATURE:
<221> NAME/KEY: misc_feature
<222> LOCATION: 30
<223> OTHER INFORMATION: 3' nucleotide linked to biotin
<220> FEATURE:
<221> NAME/KEY: misc_feature
<222> LOCATION: 1
<223> OTHER INFORMATION: 5' nucleotide linked to 6-FAM(M5)

<400> SEQUENCE: 81
ctcggcacgg ttctacggag tgcatagcga                                    30

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
atgccgatga cctgcagaat t                                             21

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
```

```
atgccgatga cctgcagaat c                                              21

<210> SEQ ID NO 84
<211> LENGTH: 18
<212> TYPE: DNA
<213> ORGANISM: Artificial Sequence
<220> FEATURE:
<223> OTHER INFORMATION: primer

<400> SEQUENCE: 84
cctcgcggat ggcgctga                                                  18

<210> SEQ ID NO 85
<211> LENGTH: 30
<212> TYPE: DNA
<213> ORGANISM: Artificial Sequence
<220> FEATURE:
<223> OTHER INFORMATION: e-tag reporter sequence

<400> SEQUENCE: 85
catcattcta tcgcgacaac gcgggccgaa                                     30

<210> SEQ ID NO 86
<211> LENGTH: 78
<212> TYPE: DNA
<213> ORGANISM: Artificial Sequence
<220> FEATURE:
<223> OTHER INFORMATION: primer

<400> SEQUENCE: 86
aggtccactg cgtccgatgt tcgactctcg gcacggttct acggagtgca tagcgagatg    60
ccgatgacct gcagaatt                                                  78

<210> SEQ ID NO 87
<211> LENGTH: 77
<212> TYPE: DNA
<213> ORGANISM: Artificial Sequence
<220> FEATURE:
<223> OTHER INFORMATION: primer

<400> SEQUENCE: 87
aggtccactg cgtccgatgt tcgactctac ttgccttcgc gtagtggagg agagttatgc    60
cgatgacctg cagaatc                                                   77

<210> SEQ ID NO 88
<211> LENGTH: 38
<212> TYPE: DNA
<213> ORGANISM: Artificial Sequence
<220> FEATURE:
<223> OTHER INFORMATION: primer

<400> SEQUENCE: 88
aggtccactg cgtccgatgt cctcgcggat ggcgctga                            38
```